United States Patent [19]
Nicolaou et al.

[11] Patent Number: 5,965,718
[45] Date of Patent: Oct. 12, 1999

[54] ANALOGS OF SARCODICTYIN AND ELEUTHEROBIN

[75] Inventors: Kyriacos C. Nicolaou, La Jolla, Calif.; Floris VanDelft, Leiden, Netherlands; Seijiro Hosokawa, Tokyo, Japan; Sanghee Kim, Waukegan, Ill.; Tianhu Li, San Diego, Calif.; Takashi Ohshima, San Diego, Calif.; Jeff Pfefferkorn, San Diego, Calif.; Dionisios Vourloumis, San Diego, Calif.; Jin-You Xu; Nicolas Winssinger, both of La Jolla, Calif.

[73] Assignee: The Scripps Research Institute, La Jolla, Calif.

[21] Appl. No.: 09/145,376

[22] Filed: Sep. 1, 1998

Related U.S. Application Data
[60] Provisional application No. 60/063,125, Oct. 24, 1997.

[51] Int. Cl.$^6$ .......................... C07H 15/24; A61K 31/70; A61K 31/34; C07D 307/77
[52] U.S. Cl. .............................. 536/18.1; 514/28; 514/63; 514/277; 514/365; 514/374; 514/385; 514/396; 514/406; 514/461; 514/469; 514/691; 514/703; 536/17.4; 548/146; 548/215; 548/300.1; 549/456; 549/462; 549/463
[58] Field of Search .............................. 514/23, 63, 277, 514/365, 374, 385, 396, 406, 461, 469, 691, 703, 28; 536/4.1, 17.4, 18.1; 548/146, 215, 300.1; 549/456, 462, 463

[56] References Cited

FOREIGN PATENT DOCUMENTS
96/36335  11/1996  WIPO .

OTHER PUBLICATIONS
Lindel, et al., "Eleutherobin, a New Cytotoxin that Mimics Paclltaxel (Taxel) by Stabilizing Microtubules", *J. Am. Chem. Soc.*, 119:8744–8745 (1997).

Long, et al., "Eleutherobin, a Novel Cytotoxic Agent That Induces Tubulin Polymerization, Is Similar to Paclitaxel (Taxol)", *Cancer Research*, 58:1111–1115 (1998).

(List continued on next page.)

*Primary Examiner*—Howard C. Lee
*Attorney, Agent, or Firm*—Donald G. Lewis

[57] ABSTRACT

Sarcodictyin A and B, eleutherobin, and bioactive analogs thereof synthesized using solid phase and solution phase chemistries. The synthetic method employs an attachment of common precursors, e.g., compounds 1880 or 200, on a solid support for generating conjugates 230 and 240, followed by standard chemical manipulations. A combinatorial library of sarcodictyins and eletherobin analogs was constructed with modified C-8 ester, C-15 ester and C-4 ketal functionalities and was screened for activity with respect to tubulin polymerization and cytotoxic activity against tumor cells, including Taxol-resistant lines. Compounds 600, 610, 630, 660–700, 730, 760, 850, and 920 were identified to be of equal or superior biological activities as compared to their corresponding natural product.

8 Claims, 39 Drawing Sheets

OTHER PUBLICATIONS

D'Ambrosio et al., 105. Isolation from the Mediterranean Stoloniferan Coral Sarcodictyon roseum of Sarcodictyin C. D. E, and F, Novel Diterpenoidic Alcohols Esterified by (E)–or (Z)–N(1)–Methylurocanic Acid. Failure of the Carbon–Skeleton Type as Clas, 1988.

D'Ambrosio et al., "189. Sarcodictyin A and Sarcodictyin B, Novel Diterpenoidic Alcohols Esterfied by (E)–N(1)–Methylurocanic Acid. Isolation from the Mediterrranean Stolonifer Sarcodictyon roseum", Helvetica Chimica Acta, vol. 70: 2019–2027, 1987.

Ketzinel et al., "Sarcodictyin A and Two Novel Diterpeniod Glycosides, Eleuthosides A and B, from the Soft Coral Eleutherobia aurea", J. Nat. PRod., vol. 59: 873–875, 1996.

Lin et al., "The Valdivones, Anti–Inflammatory Diterpene Esters from the South African Soft Coral Alcyonium valdivae", Tetrahedron, vol. 49(36): 7977–7984, 1993.

Nicolaou et al., "Total Synthesis of Eleutherobin", Angew. Chem. Int. Ed. Engl., vol. 36(22): 2520–2524, 1997.

Nicolaou et al., "Synthesis of the Tricyclic Core of Eleutherobin and Sarcodictyins and Total Synthesis of Sarcodictyin A", JACS, vol. 119: 11353–11354, 1997.

Nicolaou et al., "Synthesis and Biological Activity of Sarcodiuctyins", Angew. Chem. Int. Ed., vol. 37(10): 1418–1421, 1998.

Nicolaou et al., "Total Synthesis of Sarcodictyins A and B", JACS, vol. 120: 8661–8673, 1998.

Nicolaou et al., "Total Synthesis of Eleutherobin and Eleuthosides A and B", JACS, vol. 120: 8674–8680, 1998.

Nicolaou et al., "Solid and Solution Phase Synthesis and Biological Evaluation of Combinatorial Sarcodictyin Libraries", JACS, vol. 120: 10814–10826, 1998.

Nicolaou, K.C. "Taxol (Chapter 34)" from Classics in Total Synthesis (edited by Nicolaou and Sorensen), published by VCH, pp. 655–672, 1996.

Ciomei et al., "Sarcodictyins: A new class of marine derivatives with mode of action similar to Taxol", Proc. Amer. Assoc. Cancer Res., vol. 38: p. 5 (abstract #30), 1997.

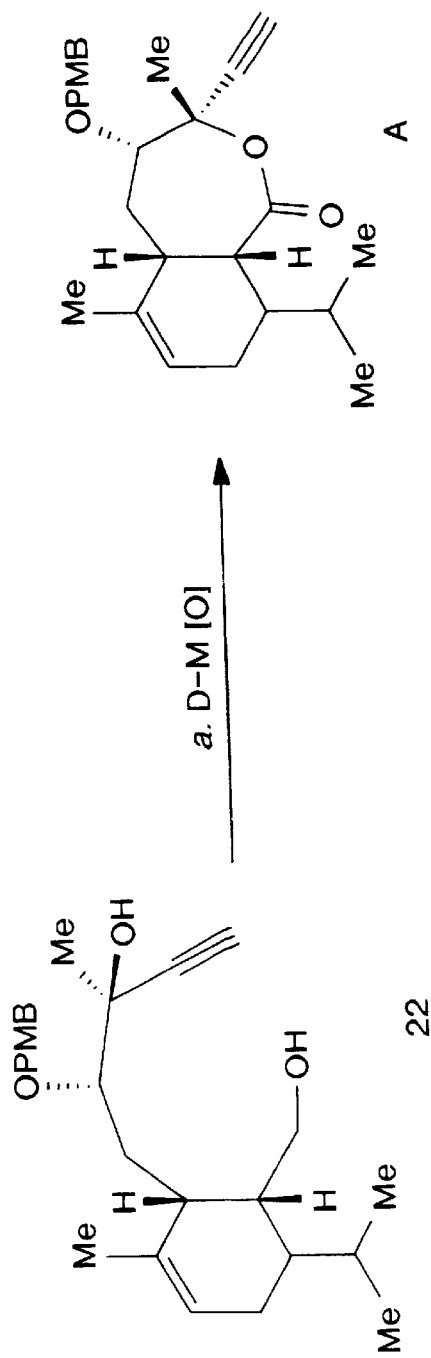
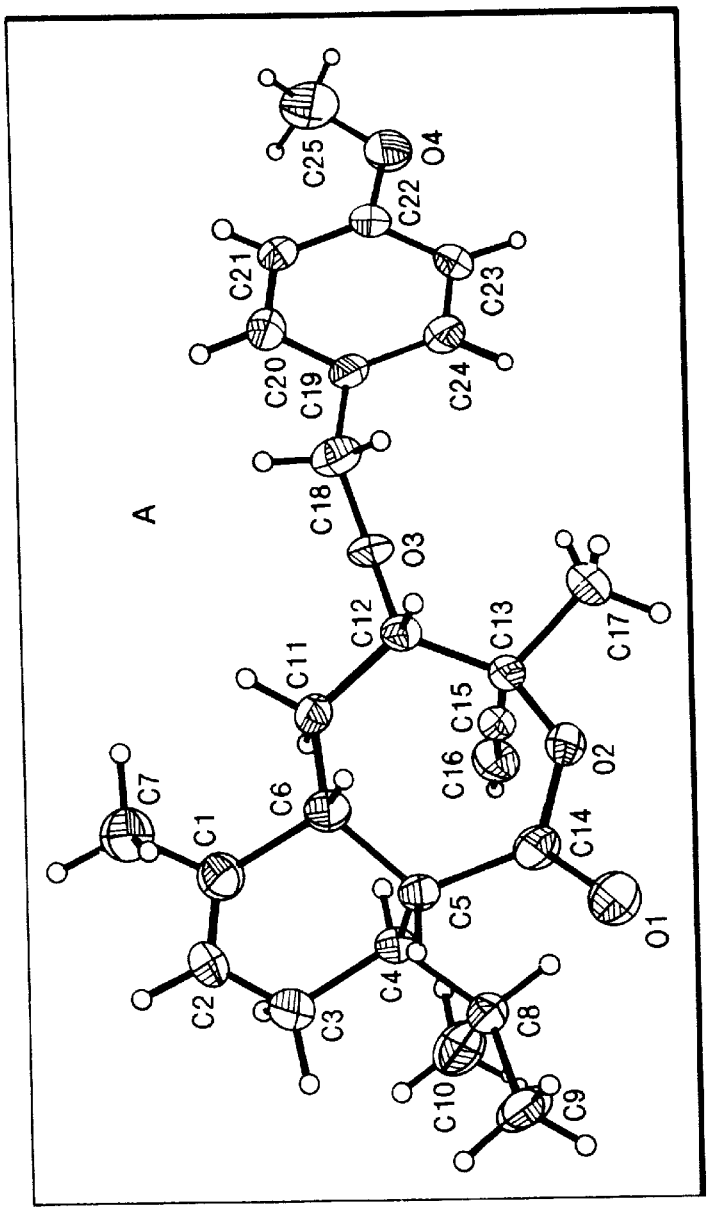
FIG. 5

| substrate | conditions | products (ratio) | yield (%) |
|---|---|---|---|
| 38: R = PMB, R² = H | Lindlar's cat., MeOH | 40:49 (ca. 2 : 1) | 50 (of 40) |
| 38: R = PMB, R² = H | Lindlar's cat., CH₂Cl₂ | 40:49 (ca. 3 : 1) | 60 (of 40) |
| 38: R = PMB, R² = H | Lindlar's cat., EtOAc | 40:49 (ca. 3 : 1) | 60 (of 40) |
| 38: R = PMB, R² = H | Lindlar's cat., toluene; then PPTS, MeOH | 41:49 (ca. 5 : 1) | 75 (of 41, two steps) |
| 38: R = PMB, R² = H | Pd / BaSO₄, pyridine | 40:49 (ca. 3-5 : 1) | 74 (of 40) |
| 45: R = H, R² = H | Lindlar's cat., toluene; then PPTS, MeOH | 42:49 (ca. 2-3 : 1) | 52 (of 42, two steps) |
| 45: R = H, R² = H | [Rh(nbd)(dppb)]BF₄, acetone; then PPTS, MeOH | 42:49 (ca. >10 : 1) | 80 (of 42, two steps) |

| Structure | %Tubulin polymerization [a] | Ref. Structure | %Tubulin polymerization [a] | Ref. Structure | %Tubulin polymerization [a] |
|---|---|---|---|---|---|
| 7: R = Me | 67 | 780: R = OH | 2 | 940: R = CO₂Bn | 1 |
| 8: R = Et | 71 | 540: R = OAc | 34 | 950: R = CONHMe | 3 |
| | | | | 960: R = CONHBn | 2 |
| | | | | 970: R = CH₂NHAc | 6 |
| | | | | 980: R = CH₂NHBz | 5 |
| | | | | 990: R = CO₂Me | 6 |
| | | | | 1000: R = p-MeOBnNH | 3 |
| 510: R = OH | 37 | 790: R = (CH₂)₂CH₂Cl | 22 | 1010: R = CO₂Me | 4 |
| 520: R = F | 27 | 800: R = CH₂CH₂Cl | 21 | 1020: R = CONHMe | 2 |
| 530: R = OAc | 37 | 810: R = ⁿBu | 23 | 1030: R = CONHBn | 2 |
| 550: R = OBz | 12 | 820: R = CH₂Ph | 38 | 1040: R = CO₂Bn | 1 |
| 560: R = N₃ | 24 | 830: R = (CH₂)₃CH₂Ph | 1 | 1050: R = CH₂NHAc | 1 |
| 570: R = OCONHPh | 24 | 840: R = Pr | 21 | 1060: R = CH₂NHBz | 2 |
| 580: R = NHAc | 30 | | | | |
| 590: R = NHBz | 5 | | | | |

FIG. 20B

| Structure | % Tubulin polymerization [a] | Ref. Structure | % Tubulin polymerization [a] | Ref. Structure | % Tubulin polymerization [a] |
|---|---|---|---|---|---|
| (imidazole epothilone core, OMe, CO₂R) 600: R = Me | 72 | (imidazole epothilone core, OEt, CO₂R) 850: R = Me | 85 | (pyridine epothilone core, OMe, CO₂Me) 480 | 18 |
| 610: R = Et | 46 | 860: R = CH₂CH₂OBn | 28 | | |
| 620: R = Bn | 61 | 870: R = (CH₂)₂CH(CH₃)₂ | 20 | | |
| 630: R = CH₂CH₂Cl | 40 | | | | |
| 640: R = (CH₂)₂CH₂Cl | 30 | | | | |
| 650: R = CH₂CF₃ | 31 | (imidazole epothilone core, OMe, PMB ester) 880 | 22 | (thiazole epothilone core, OMe, CH₂OH) 430 | 5 |
| 660: R = (CH₂)₃CH₂Ph | 38 | | | | |
| 670: R = ⁿBu | 52 | | | | |
| 680: R = ⁿPr | 69 | | | | |
| 690: R = CH₂CH₂OBn | 54 | 890: R = Me | 26 | (thiazole epothilone core, OMe, CO₂Me) 490 | 42 |
| 700: R = CH₂CH=CH₂ | 51 | 900: R = Et | 18 | | |
| 710: R = (CH₂)₂CH(CH₃)₂ | 10 | | | | |
| (imidazole epothilone core, OMe, R) 720: R = CHO | 4 | | | | |
| 730: R = CH(OMe)₂ | 74 | | | | |

| Cmpd# | Induction of tubulin polymerization %Tubulin Polymerization[a] | Inhibition of carcinoma cell growth[b] | | |
|---|---|---|---|---|
| | | 1A9 | 1A9PTX10 | 1A9PTX22 |
| | | IC$_{50}$ (nM) | | |
| 1 taxol | 65 | 2 | 50 | 40 |
| 2 epothilone A | 73 | 2 | 19 | 4 |
| 3 epothilone B | 97 | 0.04 | 0.035 | 0.04 |
| 7 sarcodictyin A | 67 | 240 | 140 | 360 |
| 8 sarcodictyin B | 71 | 2 | 160 | 80 |
| 480 | 18 | 430 | 1800 | >2000 |
| 490 | 42 | 300 | 244 | 180 |
| 500 | 4 | >2000 | 800 | 385 |
| 510 | 37 | 800 | >2000 | >2000 |
| 520 | 27 | 1850 | >2000 | >2000 |
| 530 | 37 | 1050 | >2000 | 1620 |
| 540 | 34 | 1400 | >2000 | >2000 |
| 560 | 47 | >2000 | >2000 | 1800 |
| 580 | 30 | 800 | 1600 | 1200 |
| 600 | 72 | 70 | 4 | 84 |
| 610 | 46 | 2 | 1 | 60 |
| 620 | 61 | 360 | 1210 | 540 |
| 630 | 40 | 95 | 85 | 100 |
| 640 | 30 | 200 | 350 | 290 |
| 660 | 38 | 110 | 90 | 120 |
| 670 | 52 | 25 | 35 | 31 |
| 680 | 69 | 3 | 4 | 5 |
| 690 | 54 | 80 | 91 | 85 |
| 700 | 51 | 9 | 12 | 10 |
| 720 | 4 | 600 | 400 | 600 |
| 730 | 74 | 30 | 45 | 60 |
| 740 | 47 | >2000 | >2000 | 1800 |
| 750 | 75 | 500 | 1400 | 700 |
| 760 | 52 | 45 | 65 | 60 |
| 850 | 85 | 110 | 13 | 160 |
| 860 | 28 | 110 | 400 | 440 |
| 870 | 20 | 500 | 1240 | 1000 |
| 880 | 22 | 1400 | 1300 | 1400 |
| 890 | 26 | 640 | 1300 | 900 |
| 920 | 48 | 110 | 90 | 130 |

FIG. 21

| conditions | | products (ratio 25:26)[c] | yield (%) |
|---|---|---|---|
| CH$_2$Cl$_2$, | −78 °C[a] | 1 : 3 | 52 (mixture of 2500 and 2600) |
| hexane, | −78 °C[a] | 1 : 8 | 34 (mixture of 2500 and 2600) |
| MeCN, | −35 °C[a] | 1 : 4 | 62 (mixture of 2500 and 2600) |
| Et$_2$O, | −80 °C[a] | 2 : 1 | 65 (mixture of 2500 and 2600) |
| Et$_2$O, | 0 °C[a] | 2.5 : 1 | 54 (of 2500) |
| Et$_2$O, | 25 °C[a] | 3 : 1 | 60 (mixture of 2500 and 2600) |
| dioxane:toluene (1:1), 0 °C[b] | | 7 : 1 | 67 (of 2500) |
| dioxane:toluene (2:1), 0 °C[b] | | 8 : 1 | 75 (of 2500) |
| dioxane:toluene (3:1), 0 °C[b] | | 7 : 1 | 70 (of 2500) |

ANALOGS OF SARCODICTYIN AND ELEUTHEROBIN

This application claims benefit of Provisional Appl. 06/063,125, filed Oct. 24, 1997.

GOVERNMENT RIGHTS

This invention was made with government support under Grant No. CA 46446 awarded by the National Institutes of Health. The U.S. government has certain rights in the invention.

SPECIFICATION

TECHNICAL FIELD

The present invention relates to sarcodictyin A and B, eleutherobin. More particularly, the present application relates to analogs of sarcodictyin and eleutherobin and to their synthesis and use.

BACKGROUND

The Sarcodictyins A (7) and B (8) (FIG. 1) were discovered by Pietra et al. in the Mediterranean stoloniferan coral *Sarcodictyon roseum* and first reported in 1987 (D'Ambrosio et al. *Helv. Chim. Acta* 1987, 70, 2019–2027; D'Ambrosio et al. *Helv. Chim. Acta* 1988, 71, 964–976). Sarcodictyins C–F were subsequently disclosed by the same group (D'Ambrosio et al. *Helv. Chim. Acta* 1988, 71, 964–976).

Eleutherobin was isolated from an Eleutherobia species of soft coral (possibly *E. albiflora Alcynacea*, Alcyoniidea collected from the Indian Ocean near Bennett's Shoal in Western Australia) by Fenical et al. and first reported in 1995 (Fenical et al. U.S. Pat. No. 5,473,057, Dec. 5, 1995).

Eleuthosides A (5) and B (6) were isolated from an *Eleutherobia aurea* species of soft coral (collected near the Kwazula-Natal coast of South Africa) and reported by Kashman et al. (Ketzinel et al. *J. Nat. Prod.* 1996, 59, 873–875). These substances are closely related to eleutherobin (4).

Valdivone (6) was first reported by Kennart and Watson (Lin et al. *Tetrahedron* 1993, 49, 7977–7984). These substances are also related, both structurally and with regards to their biological action, to eleutherobin (4) and to eleuthosides A (5) and B (6) (FIG. 1).

All four of the above marine-derived natural products (4–8) share the same mechanism of action with the soil-derived (myxobacteria) epothilones A (2) and B (3) (FIG. 1) and the forest-residing Taxol™ (1) (FIG. 1). (Lindel et al. *J. Am. Chem. Soc.* 1997, 119, 8744–8745; Long et al. *Cancer Res.* 1998, 58, 1111–1115). This mechanism involves tubulin polymerization and microtubule stabilization.

What is needed are synthetic analogs of sarcodictyin A and B, eleutherobin having enhanced bioactivity, and synthetic methods for producing these natural products and their bioactive analogs.

SUMMARY OF THE INVENTION

The invention is directed to bioactive analogs of eleutherobin, eleuthosides A and B, and sarcodictyin A and B, and to their synthesis and use for promoting tubulin assembly and/or stabilizing microtubules.

More particularly, an important aspect of the invention is directed to analogs of eleutherobin, eleuthosides A and B, sarcodictyin A and B. Preferred analogs are represented by the following structure:

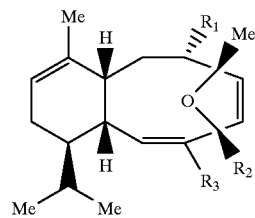

Preferred $R_1$ radicals in the above structure include the radicals —OH and —OAc or any radical represented by the following structures:

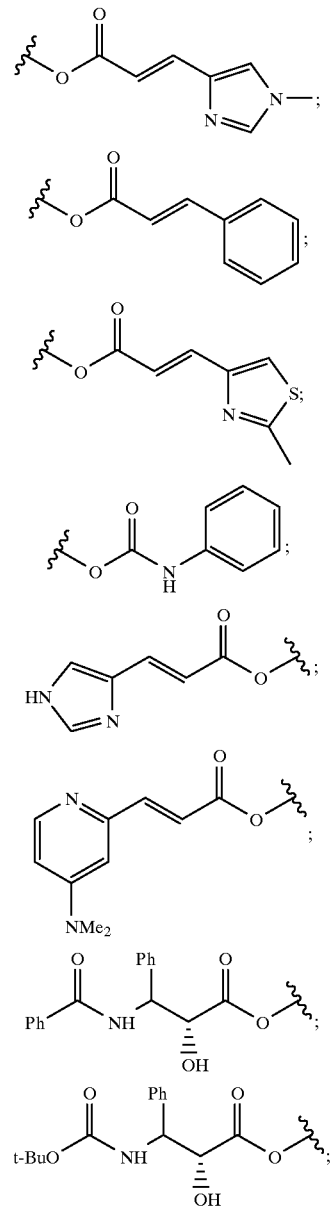

-continued

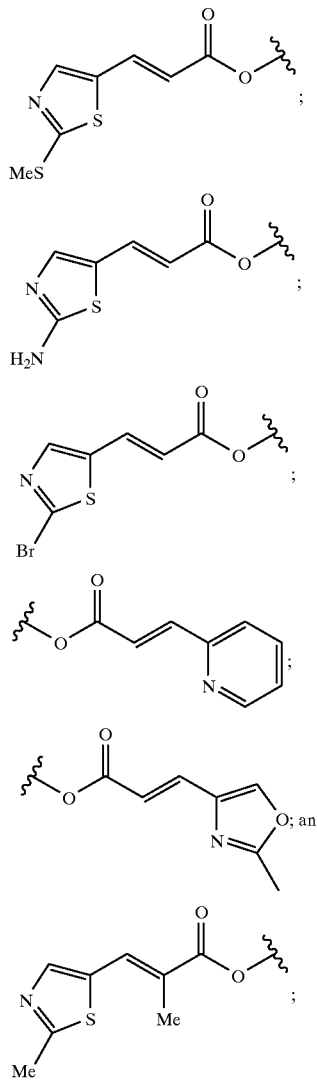

Preferred R₂ radicals include following: —OH, —O(C₁-C₆ alkyl), —OCH₂CF₃, —O-iso-propyl, —O-tert-butyl, —O-benzyl, —OCH₂CH=CH₂, —OCH₂CCH, —O(CH₂)₂—OH, —NHMe, —NMe₂, —NHEt, —NEt₂, —NH-n-propyl, —N-(propyl)₂, —NH-iso-propyl, —N-butyl₂, —NH-benzyl, —N-benzyl₂, —SH, —SMe, —SEt, —S-n-propyl, —S-iso-propyl, —S-n-butyl, —S-benzyl, and —S-phenyl. Preferred R₃ radicals include the following: —CH₂OC(O)CH₃, —CH₂OC(O)-phenyl, —CH₂—OC(O)O—CH₃, —CH₂OC(O)NH-phenyl, —CH₂—OH, —CH(O), —CH₂—O-tri-isopropylsilyl, —CH₂O—Ac, —CH₂—F, —CH₂N₃, —CH₂NAc, —CH₂NBz, C(O)—O(C₁-C₆ alkyl), —C(O)—CH₂CF₃, —C(O)—CH₂CHCH₂, —C(O)—O—CH₂CH₂Cl, —C(O)O (CH₂)₂CH₂Cl, —C(O)O(CH₂)₂CH(CH₃), —C(O)CH₂Ph, —C(O)CH₂-phenyl-OMe, —CH₂—O-tetrahydropyran, —CH₂—O—C(O)CHCl₂, —CH₂—O—C(O)—CCl₃, —CH₂—O—C(O)CHBr₂, —CH₂—O—C(O)—CF₃, —CH₂—O—C(O)CHPh₂, EtC(O)—O—CH₂—, CH₂=CHC(O)—O—CH₂—, HC—CC(O)—O—CH₂—, n-propyl-C(O)—O—CH₂—, i-PrC(O)—O—CH₂—, cyclopropyl-C(O)—O—CH₂—, n-BuC(O)—O—CH₂—, i-BuC(O)—O—CH₂—, t-BuC(O)—O—CH₂—, cyclo-C₆H₁₁C(O)—O—CH₂—, phenyl-O—CH₂—, 2-furyl-C(O)—O—CH₂—, PhCH=CHC(O)—O—CH₂—, 2-thiophene-C(O)—O—CH₂—, (C₁-C₆ alkyl)-O—CH₂—, i-propyl-O—CH₂—, allyl-O—CH₂—, benzyl-O—CH₂—, AcOCH₂CH₂—O—CH₂—, —COOH, —COO—(C₁-C₆ alkyl), —COO-i-propyl, —COO-t-butyl, —COO-benzyl, —COOCH₂CH=CH₂, —COO—CH₂C—CH, —COO-cyclo-C₆H₁₁, —CONHBn, —CONH(C₁-C₆ alkyl), —CONH-propyl, and —COO—C₈H₁₇ and a radical selected from the group represented by the following structures:

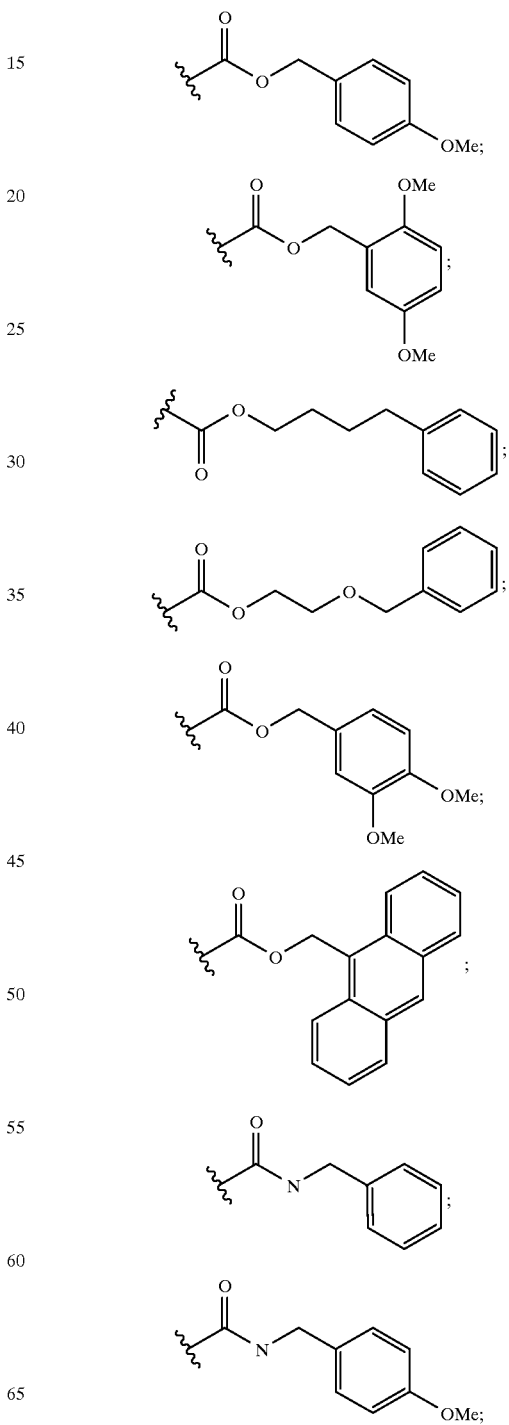

-continued

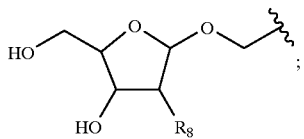

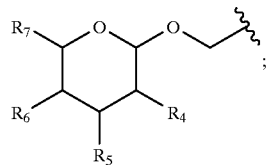

Preferred R₄ radicals include the following: —OH, —OAc, 2-Cl—AcO—, CCl₃C(O)O—, 2-Br—AcO—, CF₃C(O)O—, 2-phenyl-AcO—, (C₁-C₆ alkyl) —C(O)O—, CH₂=CHC (O)O—, HC≡—CC(O)O—, i-propyl-C(O)O—, cyclo-propyl-C(O)O—, i-butyl-C(O)O—, t-butyl-C(O)O—, cyclo-C₆H₁₁C(O)O—, phenyl-O—, 2-furylC(O)O—, PhCH=CHC(O)O—, and 2-thiophene-C(O)O—. Preferred R₅ radicals include —O—Ac and —OH. Preferred R₆ radicals include —O-acyl and —OH. Preferred R₇ radicals include —H and -methyl. Preferred R₈ radicals include —OAc, 2-Cl—AcO—, CCl₃C(O)O—, 2-Br—AcO—, CF₃C(O)O—, 2-phenyl-AcO—, (C₁-C₆ alkyl)-C(O)O—, CH₂=CHC(O)O—, HCCC(O)O—, i-propyl-C(O)O—, cyclo-propyl-C(O)O—, i-butyl-C(O)O—, t-butyl-C(O)O—, cyclo-C₆H₁₁C(O)O—, phenyl-O—, 2-furylC(O)O—, PhCH=CHC(O)O—, and ²-thiophene-C(O)O—. However, the following provisos pertain:

a. if R₁ is

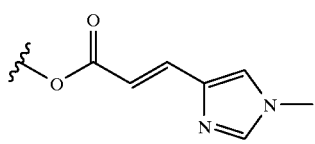

and R₂ is —OH, then R₃ cannot be simultaneously —CO₂-methyl or —CO₂-ethyl;

b. if R₁ is

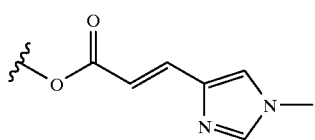

and R₂ is —O-methyl, then R₃ cannot be

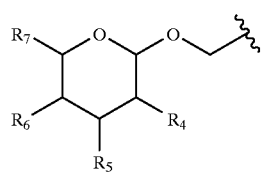

wherein R₄ is —OAc, R₅ is hydroxy, R₆ is hydroxy, and R₇ is hydrogen;

c. if R₁ is

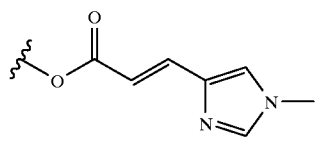

and R₂ is —OH, then R₃ cannot be

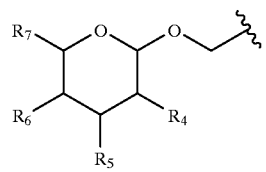

wherein R₄ is —OAc, R₅ is hydroxy, R₆ is —OAc and R₇ is hydrogen; and, d. if R₁ is

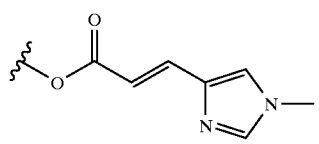

and R₂ is —OH, then R₃ cannot be

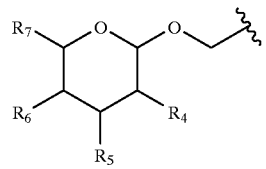

wherein R₄ and R₅ are —OAc, R₆ is —OH, and R₇ is hydrogen.

Another aspect of the invention is directed to a first advanced intermediate (compound III, FIG. 2) represented by the following structure:

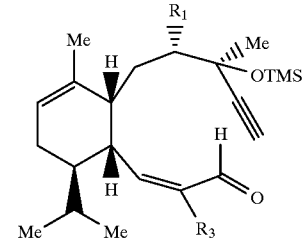

Preferred R₁ and R₃ radicals are the same as described above for the analogs of sarcodictyin A and B eleutherobin above, except that none of the provisos pertain.

Another aspect of the invention is directed to a second advanced intermediate (compound II, FIG. 2) represented by the following structure:

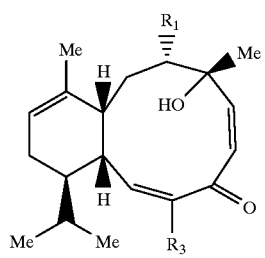

Preferred $R_1$ and $R_3$ radicals are the same as described above for the analogs of sarcodictyin A and B eleutherobin above, except that none of the provisos pertain.

Another aspect of the invention is directed to a method for cyclizing the above described first advanced intermediate (compound III, FIG. 2) for producing the above described second advanced intermediate (compound II, FIG. 2). The method employs the step of cyclizing the first advance intermediate for producing the second second intermediate.

Another aspect of the invention is directed to a method for cyclizing the above described second advanced intermediate (compound II, FIG. 2) for producing a third advanced intermediate (compound I, FIG. 2). The third advanced intermediate may be represented by the following structure:

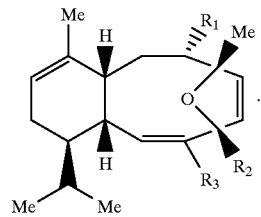

Preferred $R_1$ and $R_3$ radicals are the same as described above for the analogs of sarcodictyin A and B eleutherobin above, except that none of the provisos pertain. The method employs the step of cyclizing the second advanced intermediate for producing the third advanced intermediate. Preferred analogs of eleutherobin, eleuthosides A and B, sarcodictyin A and B may then be produced by substitution of $R_2$ onto the third advanced intermediate.

DESCRIPTION OF FIGURES

FIG. 5 illustrates the synthesis and crystal structure of A providing evidence of the abolute stereochemistry of advanced intermediate 22. a. 3.0 equivalents of Dess-Martin preiodinane, 20 equivalents of sodium bicarbonate, methylene chloride 0 to 25° C., 12 h, 70%, D-M [O]=Dess Martin oxidation.

Figure 7:
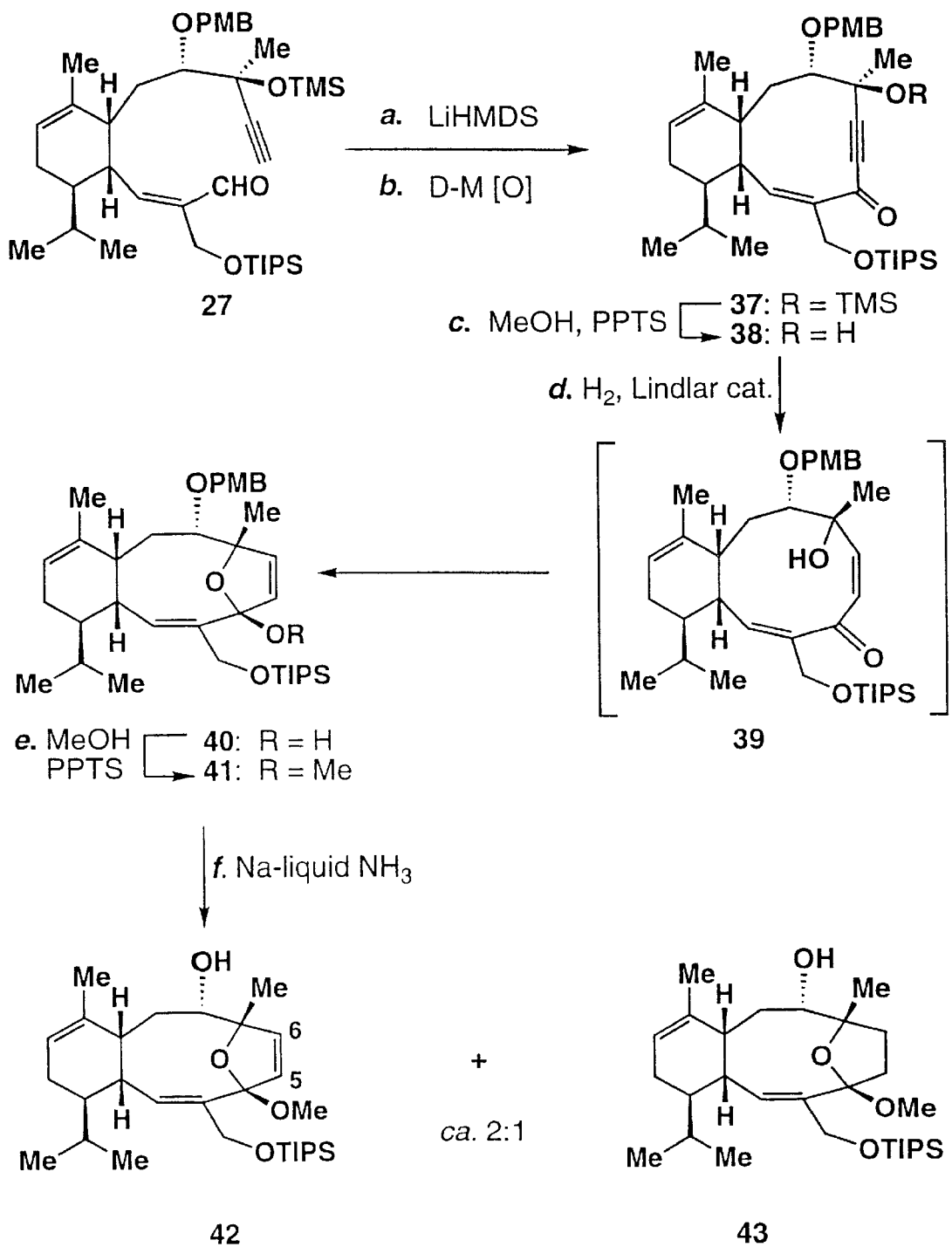

FIG. 7 illustrates the first generation synthesis of the sarcodictyin tricyclic core structure 42. Reagents and conditions. a. 1.5 equivalents of LiHMDS, THF, 25° C., 10 min; b. 2.5 equivalents of Dess-Martin periodinane, 20 equivalents of NaHCO$_3$, CH$_2$Cl$_2$, 0 to 25° C., 4.5 hours, 85% for two steps; c. 1.0 equivalent of PPTS, MeOH, 25° C., 30 min, 94%; d. 0.3 equivalents of Lindlar's cat., H$_2$I toluene, 25° C., 20 min, 75% for 40, plus 15% for 5,6-dihydro analog; e. 1.0 equivalent of PPTS, MeOH, 25° C., 10 min, 100%; f. 10 equivalents of Na—liq NH3, −78° C.; then add 41 in THF-EtOH, 5 min, 95% yield, ca. 2:1 mixture of 42 and 5,6-dihydro-analog 43. THF=tetrahydrofuran; LiHMDS=lithium bis(trimethylsilyl)amide; PPTS=pyridinium p-toluenesulfonate; Lindlar cat.=Pd/CaCO$_3$/Pb; D-M [O]=Dess-Martin oxidation.

FIG. 8 shows the selective hydrogenation studies for the construction of the sarcodictyin tricyclic core. Reagents and conditions. a. 1.0 equivalent of PPTS, MeOH, 25° C., 30 min, 94%. Lindlar's cat.=Pd/CaCO$_3$/Pb; PPTS=pyridinium p-toluenesulfonate; nbd=2,5-norbornadiene; dppb=1,4-bis(diphenylphosphino)butane.

Figure 9:
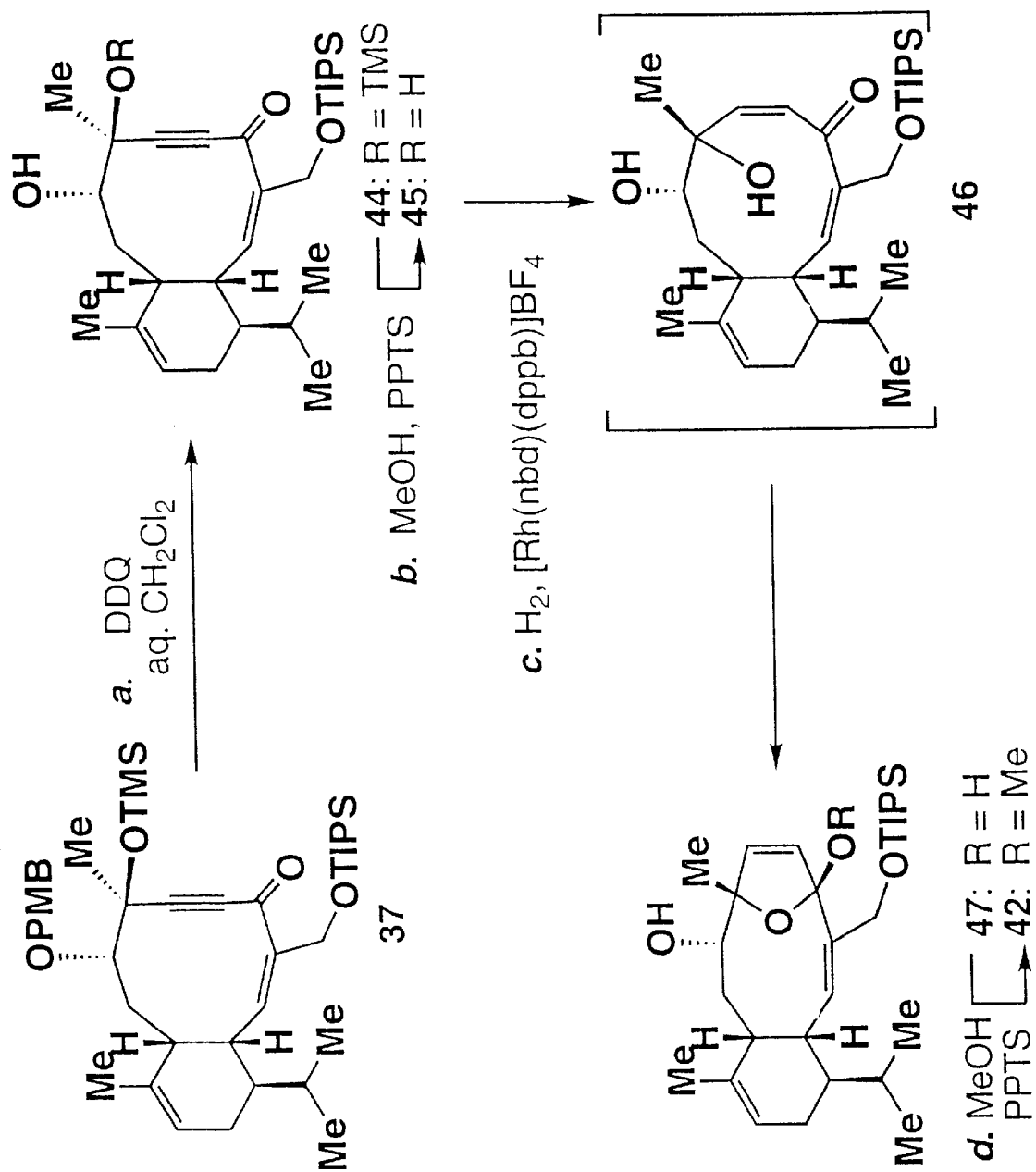

FIG. 9 shows an alternative route to tricyclic core 42. Reagents and conditions: a. 2.0 equivalents of DDQ, CH$_2$Cl$_2$:H$_2$O (18:1), 25° C., 0.5 hours, 80%; b. 1.0 equivalent of PPTS, MeOH, 25° C., 1 hour, 80%; c. 0.05 equivalents of [Rh(nbd)(dppb)]BF$_4$, H$_2$, acetone, 25° C., 10 min; d. 0.5 equivalents of PPTS, MeOH, 25° C., 10 min, 80% for two steps. DDQ=2,3-dichloro-5,6-dicyano-1,4-benzoquinone; PPTS=pyridinium p-toluenesulfonate; nbd=2,5-norbornadiene, dppb=1,4-bis(diphenylphosphino)butane.

Figure 10:
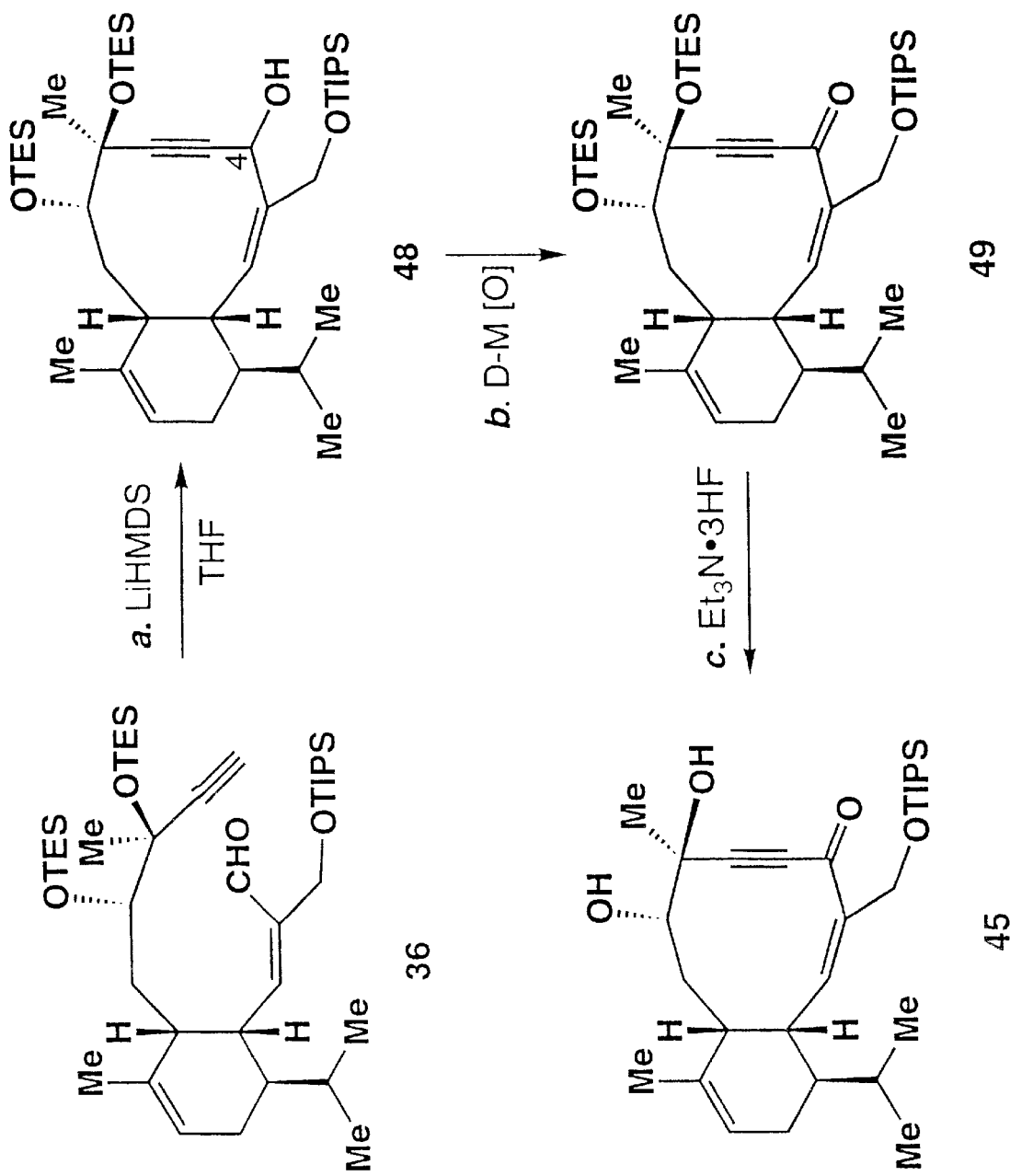

FIG. 10 shows second generation synthesis of alkynone 45. Reagents and conditions. a. 2.0 equivalents of LiHMDS, THF, −20° C., 20 min; b. 2.0 equivalents of Dess-Martin periodinane, 6.0 equivalents of NaHCO3, 6.0 equivalents of pyridine, CH2Cl2, 0° C., 1 hour, 89% for two steps; c. 5.0 equivalents of Et3N.3HF, THF (1:5), 25° C., 1.5 hours, 78%. LiHMDS=lithium bis(trimethylsilyl)amide; THF=tetrahydrofuran, D-M [O]=Dess-Martin oxidation.

Figure 11:
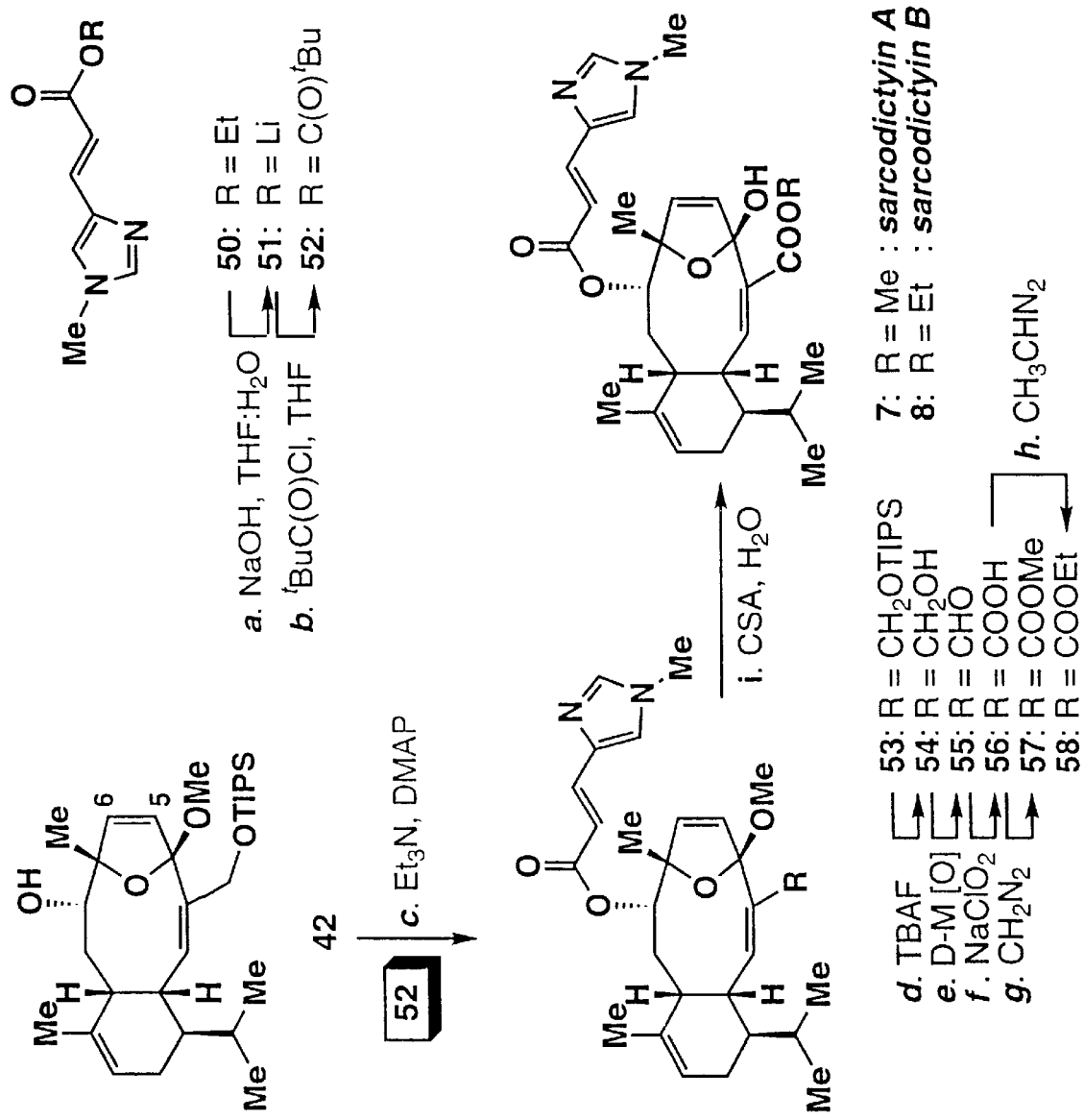

FIG. 11 shows the total synthesis of sarcodictyins A (7) and B (8); a. 1.05 equivalents LiOH.H$_2$O, THF:H$_2$O, 1:1, 25° C., 12 hours, 100%; b. 1.1 equivalents tBuC(O)Cl, THF, 25° C., 12 hours, 75%; c. 2.0 equivalents of 52, 20 equivalents of Et$_3$N, 1.0 equivalent of 4-DMAP, CH$_2$Cl$_2$, 25° C., 48 hours, 83%; d. 2.0 equivalents of TBAF, THF, 25° C., 2 hours, 100%; e. 2.0 equivalents of Dess-Martin periodinane, 10 equivalents of NaHCO$_3$, CH$_2$Cl$_2$, 25° C., 0.5 hours, 100%; f. 6.0 equivalents of NaClO$_2$, 3.0 equivalents of NaH$_2$PO$_4$, 50 equivalents of 2-methyl-2-butene, THF, tBuOH, H$_2$O, 2 hours; g. excess CH$_2$N$_2$, Et$_2$O, 10 min, 88% for two steps; h. excess CH$_3$CH$_2$N$_2$, Et$_2$O, 0.5 hours, 89% for two steps; i. 2.0 equivalents of CSA, CH$_2$Cl$_2$:H$_2$O (10:1), 25° C., 48 hours, 80% for 7, 86% for 8. THF=tetrahydrofuran; 4-DMAP=4-(N,N'-dimethylamino)pyridine; TBAF=tetra-n-butylammonium fluoride; D-M [O]=Dess-Martin oxidation; CSA=10-camphorsulfonic acid.

Figure 12:
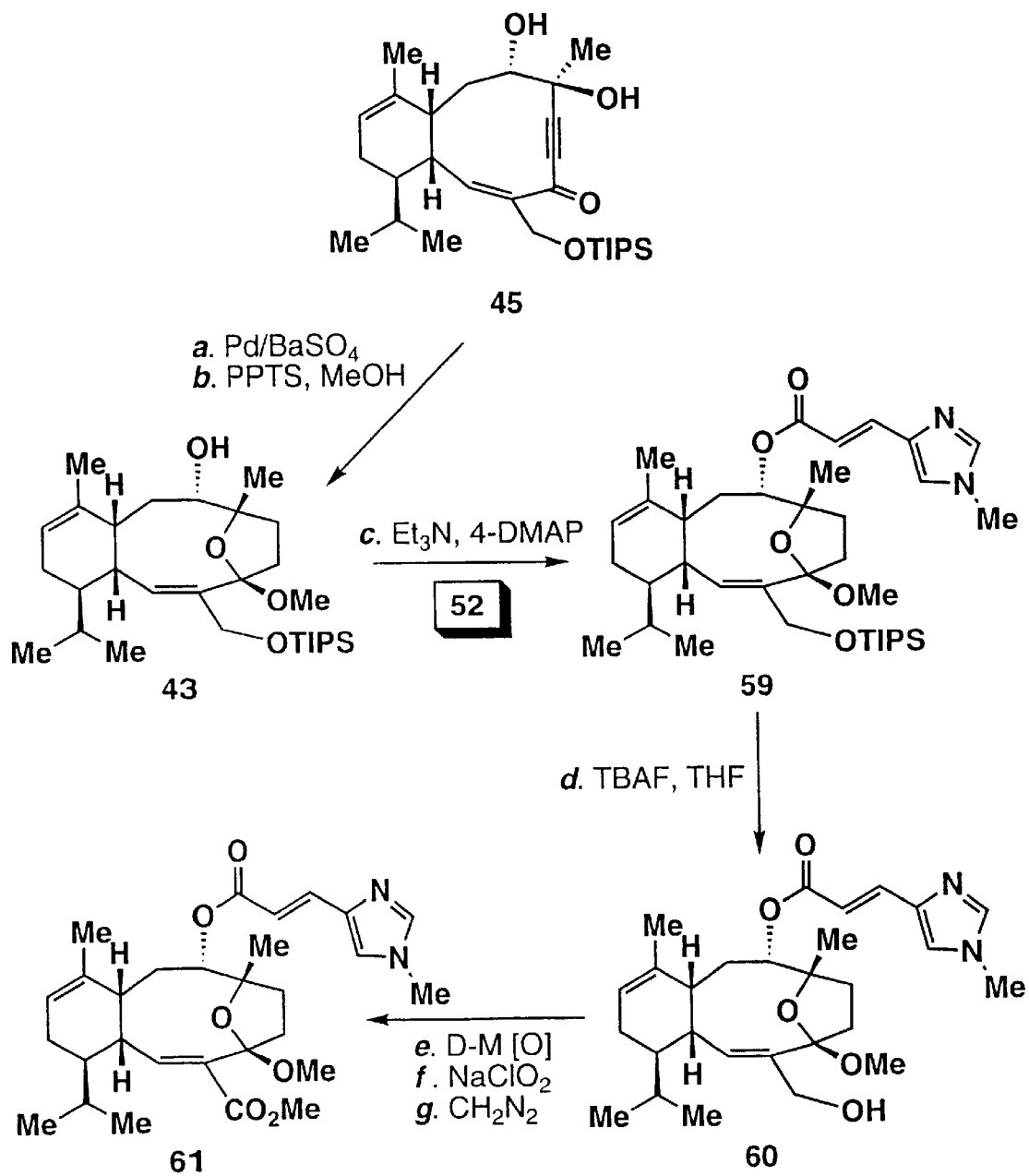

FIG. 12 shows the synthesis of C5,C6-dihydro-sarcodictyin A 61. Reagents and conditions. a. 1.0 equivalent of 5% Pd/BaSO$_4$, EtOAc, 25° C., 1 h; b. 2.0 equivalents of PPTS, MeOH, 25° C., 6 hours, 64% for two steps; c. 5.0 equivalents of 52, 20 equivalents of Et$_3$N, 2.0 equivalents of 4-DMAP, CH$_2$Cl$_2$, 25° C., 48 hours, 83%; d. 2.0 equivalents of TBAF, THF, 25° C., 2 hours, 100%; e. 2.5 equivalents of Dess-Martin periodinane, 10 equivalents of NaHCO$_3$, CH$_2$Cl$_2$, 25° C., 0.5 hours; f. 6.0 equivalents of NaClO$_2$, 3.0 equivalents of NaH$_2$PO$_4$, 50 equivalents of 2-methyl-2-butene, THF, tBuOH, H$_2$O; g. excess of CH$_2$N$_2$, Et$_2$O, 88% for three steps. PPTS=pyridinium p-toluenesulfonate, 4-DMAP=4-(N,N'-dimethylamino)pyridine, TBAF=tetra-n-butylammonium fluoride, D-M [O]=Dess-Martin oxidation.

Figure 13:
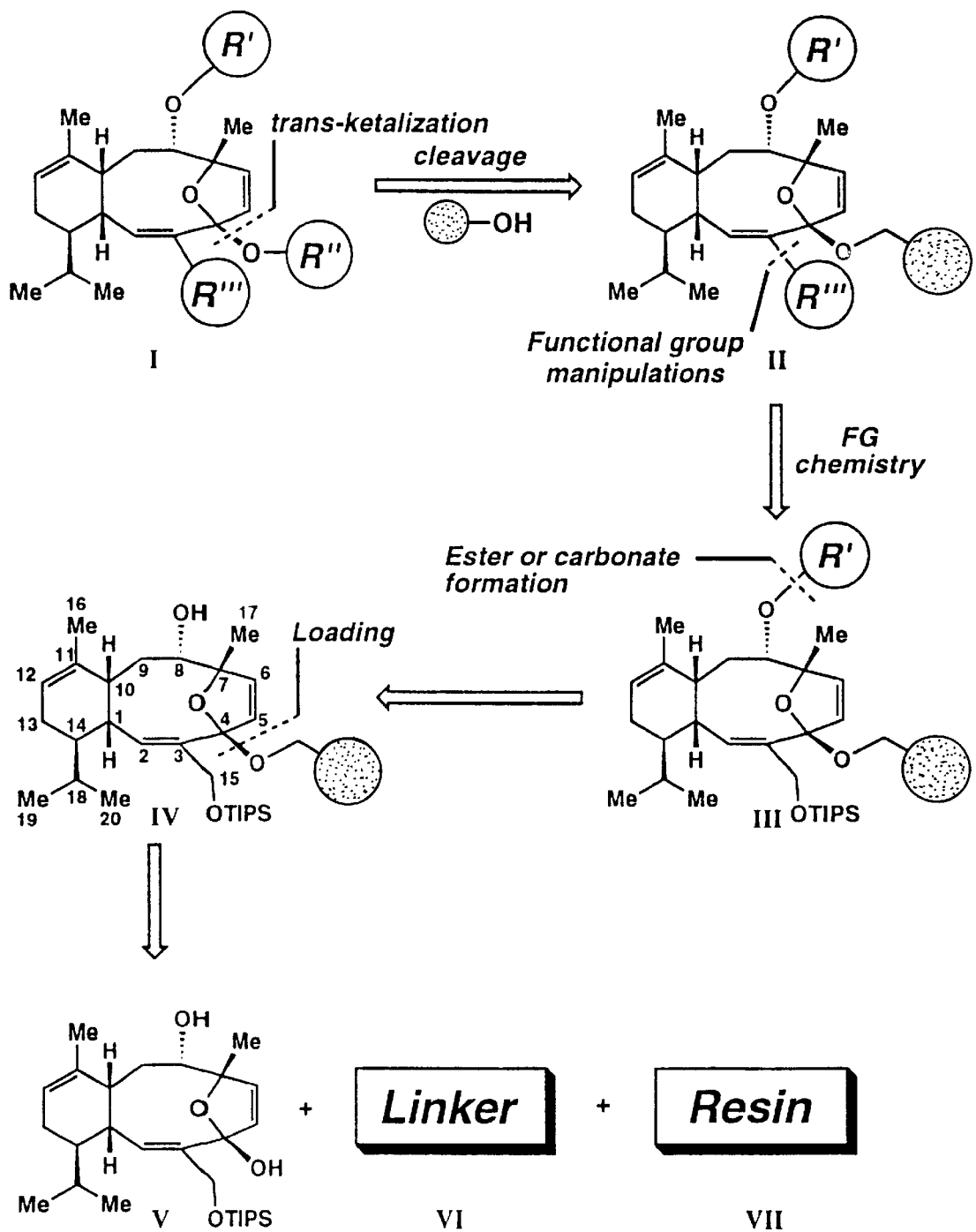

FIG. 13 illustrates the retrosynthetic analysis of a sarcodictyin library (I).

Figure 14:
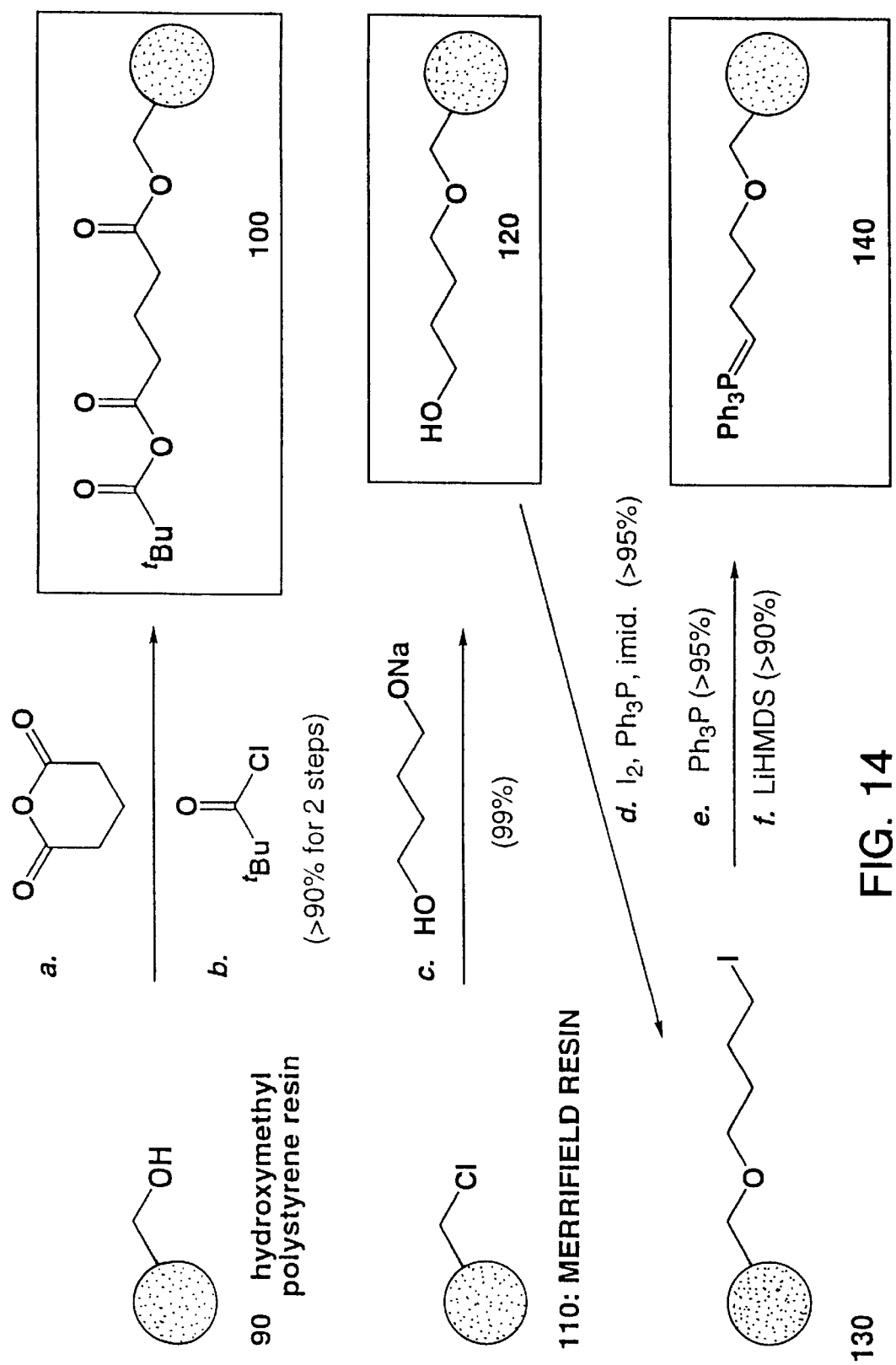

FIG. 14 shows the synthesis of resins 100, 120, and 140 for the loading of the sarcodictyin core on solid phase. Reagents and conditions. a. glutaric anhydride (4.0 equivalents), Et$_3$N (5.0 equivalents), CH$_2$Cl$_2$, 25° C., 8 hours; b. tBuCOCl (3.0 equivalents), Et$_3$N (5.0 equivalents), CH$_2$Cl$_2$, 25° C., 6 hours, >90% for two steps; c. 1,4-butanediol (4.0 equivalents), NaH (4.0 equivalents), nBuNI (0.1 equivalents), DMF, 25° C., 15 hours, 99%; d. 12 (4.0 equivalents), Ph$_3$P (4.0 equivalents), imidazole (4.0 equivalents), CH$_2$Cl$_2$, 0° C., 4 hours, >95%; e. Ph$_3$P (10.0 equivalents), 100° C., 15 hours, >95%; f. LiHMDS (1.3 equivalents), THF, 25° C., 2 hours, >90%. LiHMDS=lithium bis(trimethylsilyl)amide; THF=tetrahydrofuran; =polystyrene.

Figure 15:
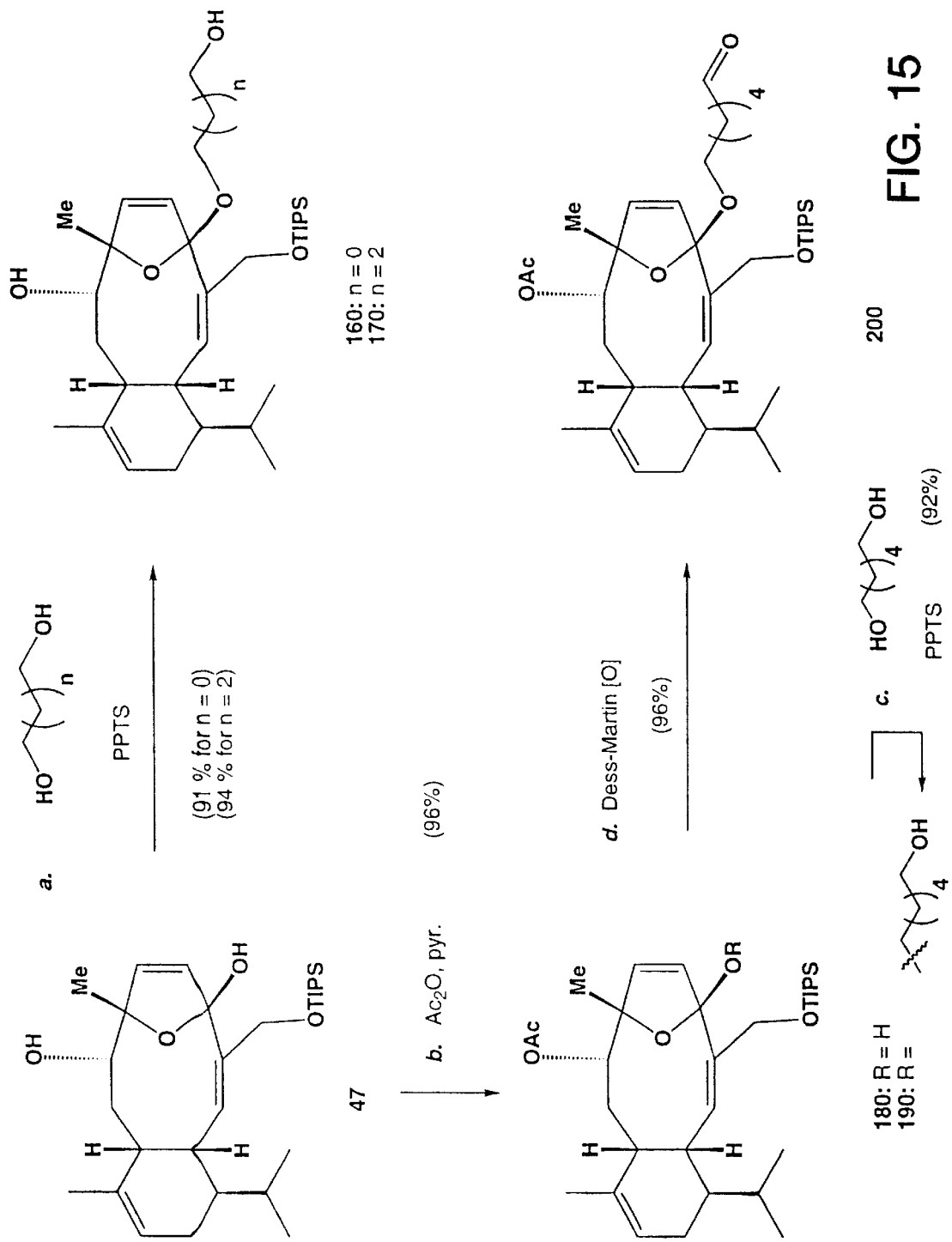

FIG. 15 illustrates the synthesis of tethered sarcodctyin cores 160, 170, 180 and 200 from 47. Reagents and conditions. a. PPTS (1.0 equivalent), diol:CH$_2$Cl$_2$ (2:1), 25° C., 2 hours, 91% for 1,2-ethanediol, 94% for 1,4-butanediol; b. Ac$_2$O (3.0 equivalents), pyridine (5.0 equivalents), CH$_2$Cl$_2$, 25° C., 1 hour, 96%; c. PPTS (1.0 equivalent), 1,6-hexanediol (10 equivalents), CH$_2$Cl$_2$, 92%; d. Dess-Martin periodinane (2.0 equivalents), pyridine (5.0 equivalents), NaHCO$_3$ (10 equivalents), CH$_2$Cl$_2$, 2 hours, 96%. PPTS=pyridinium-p-toluene sulfonate.

Figure 16:
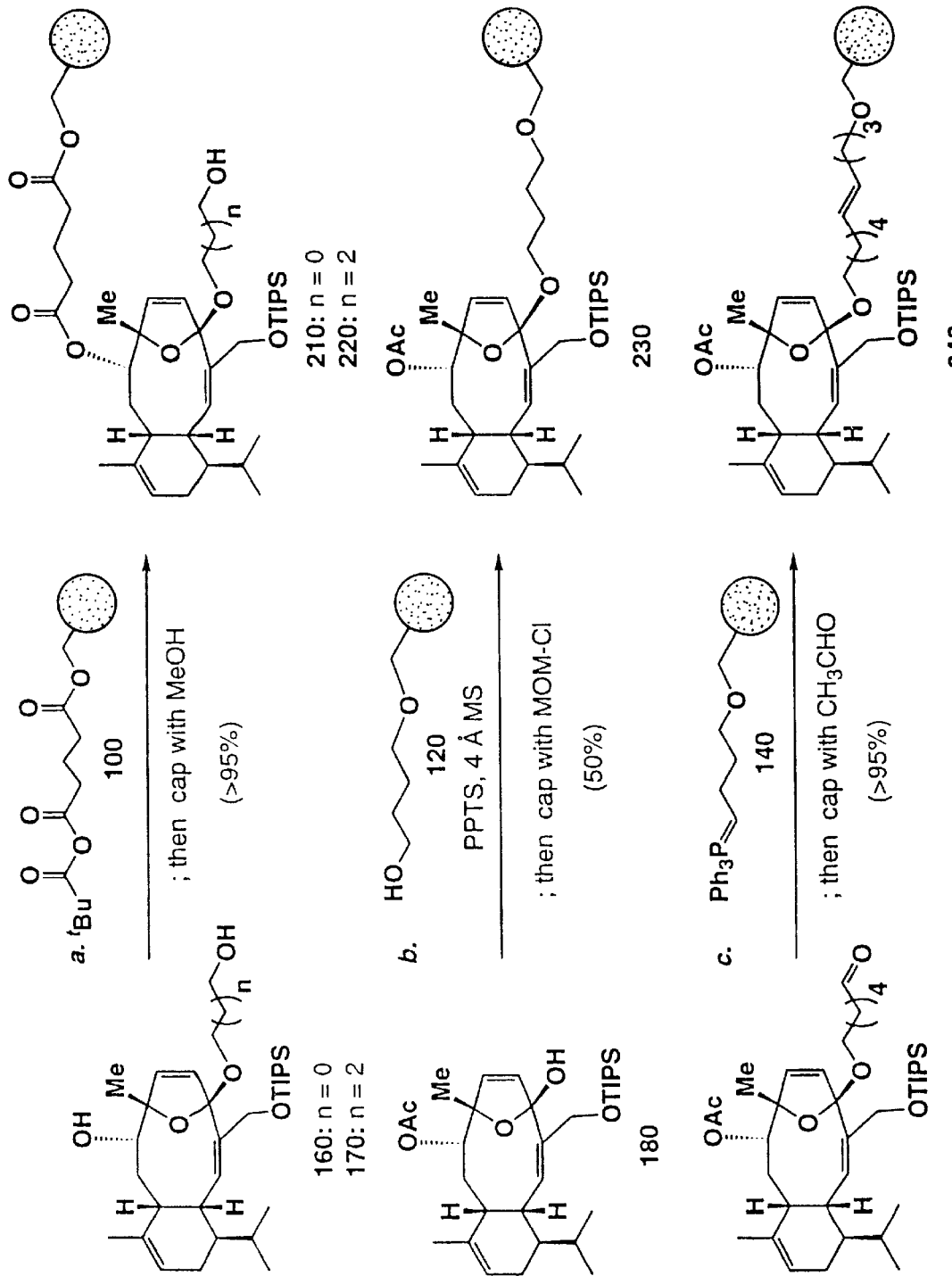

FIG. 16 shows the loading of sarcodictyin cores to solid supports. Reagents and conditions. a. 100 (5.0 equivalents), Et$_3$N (10.0 equivalents), 4-DMAP (0.5 equivalents), CH$_2$Cl$_2$, 25° C., 8 hours, >95%; then MeOH (20 equivalents) b. 120 (10 equivalents), PPTS (1.0 equivalent), 4 Å MS, CH$_2$Cl$_2$, 25° C., 48 hours, 50%; then MOM—Cl (20 equivalents), iPr$_2$NEt (20 equivalents), DMF, 25° C., 24 hours; c. 140 (5.0 equivalents), THF, −78 to 25° C., 4 hours, >95%; then CH3CHO (20 equivalents). 4-DMAP=4-(dimethylamino)pyridine; PPTS=pyridinium-p-toluene sulfonate, MOM—Cl=methoxymethyl chloride; DMF=dimethylformamide; THF=tetrahydrofuran; dark circle=polystyrene.

Figure 17:
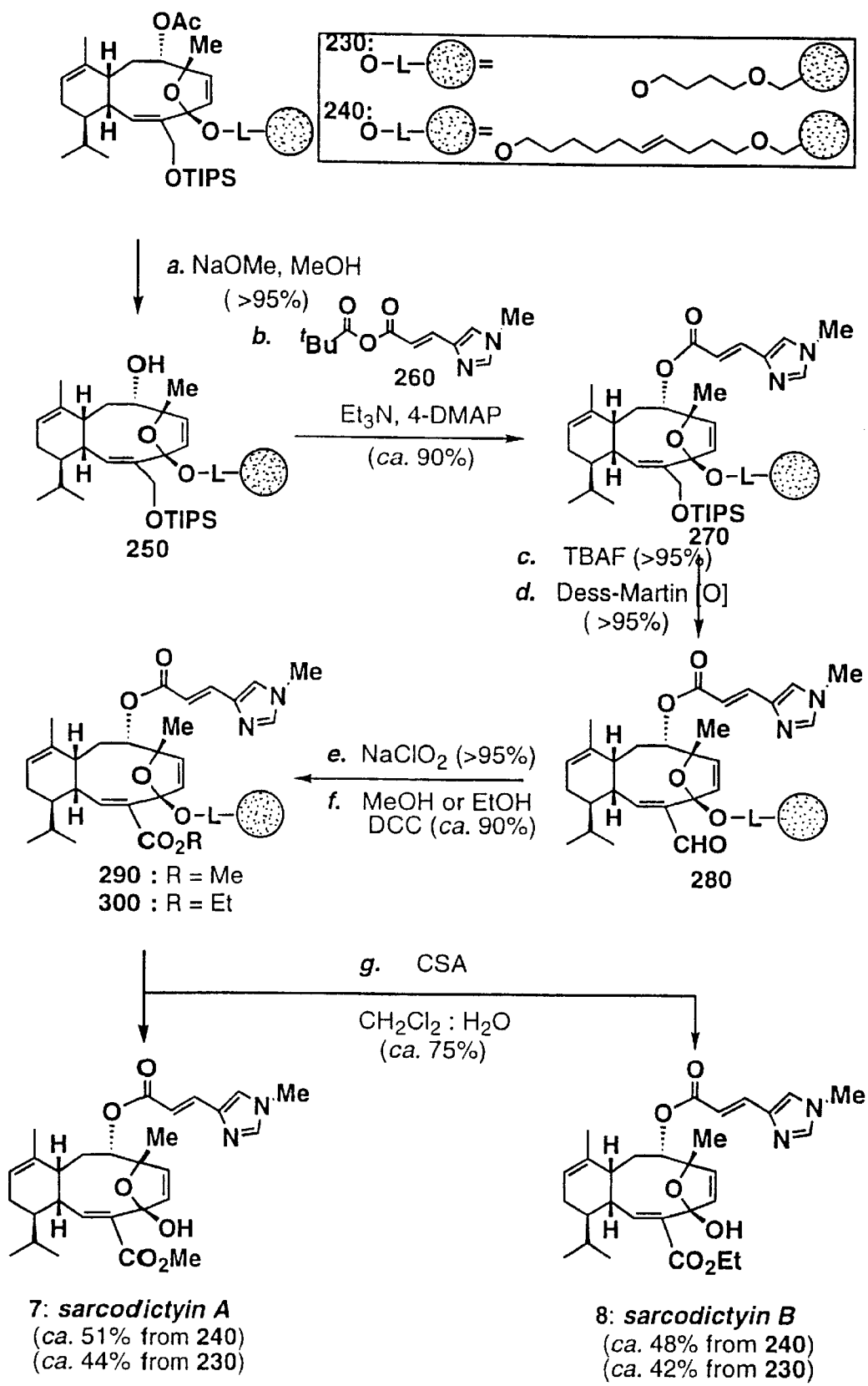

FIG. 17 shows the solid phase synthesis of sarcodictyins A (7) and B (8). a. NaOMe (5.0 equivalents), MeOH:THF (1:3), 25° C., 12 hours, >95%; b. 260 (5.0 equivalents), Et$_3$N (10 equivalents), 4-DMAP (2.0 equivalents), CH2Cl2, 25° C., 48 hours, ca. 90%; c. TBAF (10 equivalents), THF, 25° C., 8 hours, >95%; d. Dess-Martin periodinane (5.0 equivalents), NaHCO$_3$ (15 equivalents), pyridine (15 equivalents), CH$_2$Cl$_2$, 25° C., 2 hours, 95%; e. NaClO$_2$ (12 equivalents), NaH$_2$PO$_4$ (12 equivalents), 2-methyl-2-butene (50 equivalents), THF:tBuOH:H$_2$O (5:5:1) 25° C., 48 hours, >95%; f. MeOH (10 equivalents), DCC (10 equivalents), 4-DMAP (5.0 equivalents), DMF, 25° C., 48 hours, ca. 90%; g. CSA (3.0 equivalents), CH$_2$Cl$_2$:H$_2$O (2:1), 25° C., 40 hours, ca. 75%. Overall yield for sarcodictyin A: ca. 51% from 240 and ca. 44% from 230. Overall yield of sarcodictyin B: ca. 48% from 240 and ca. 42% from 230. 4-DMAP=4-(dimethylamino)pyridine; TBAF=tetra-n-butylammonium fluoride; DCC=dicyclohexylcarbodiimide; THF=tetrahydrofuran; dark circle=polystyrene.

Figure 18A:
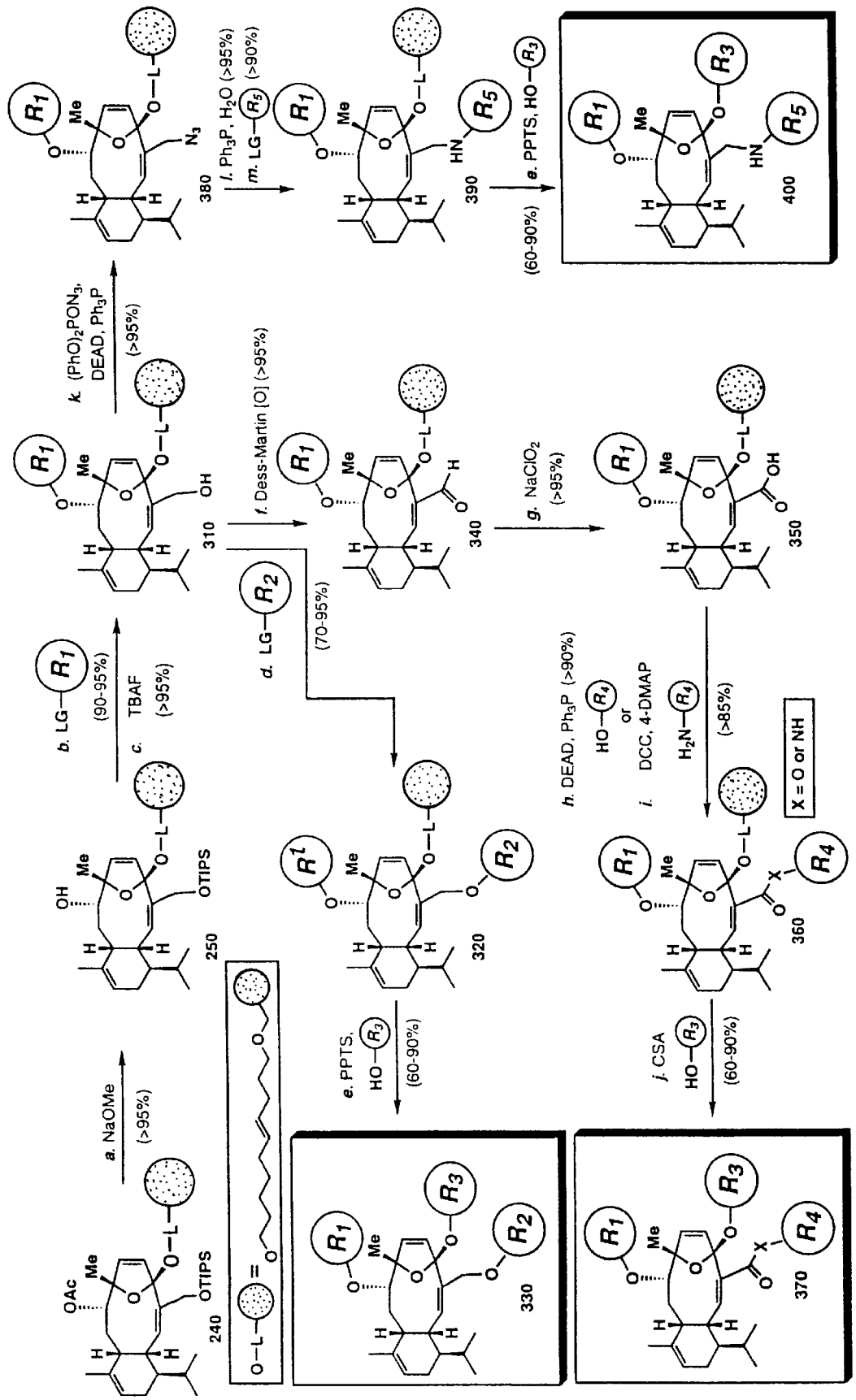
Figure 18B:
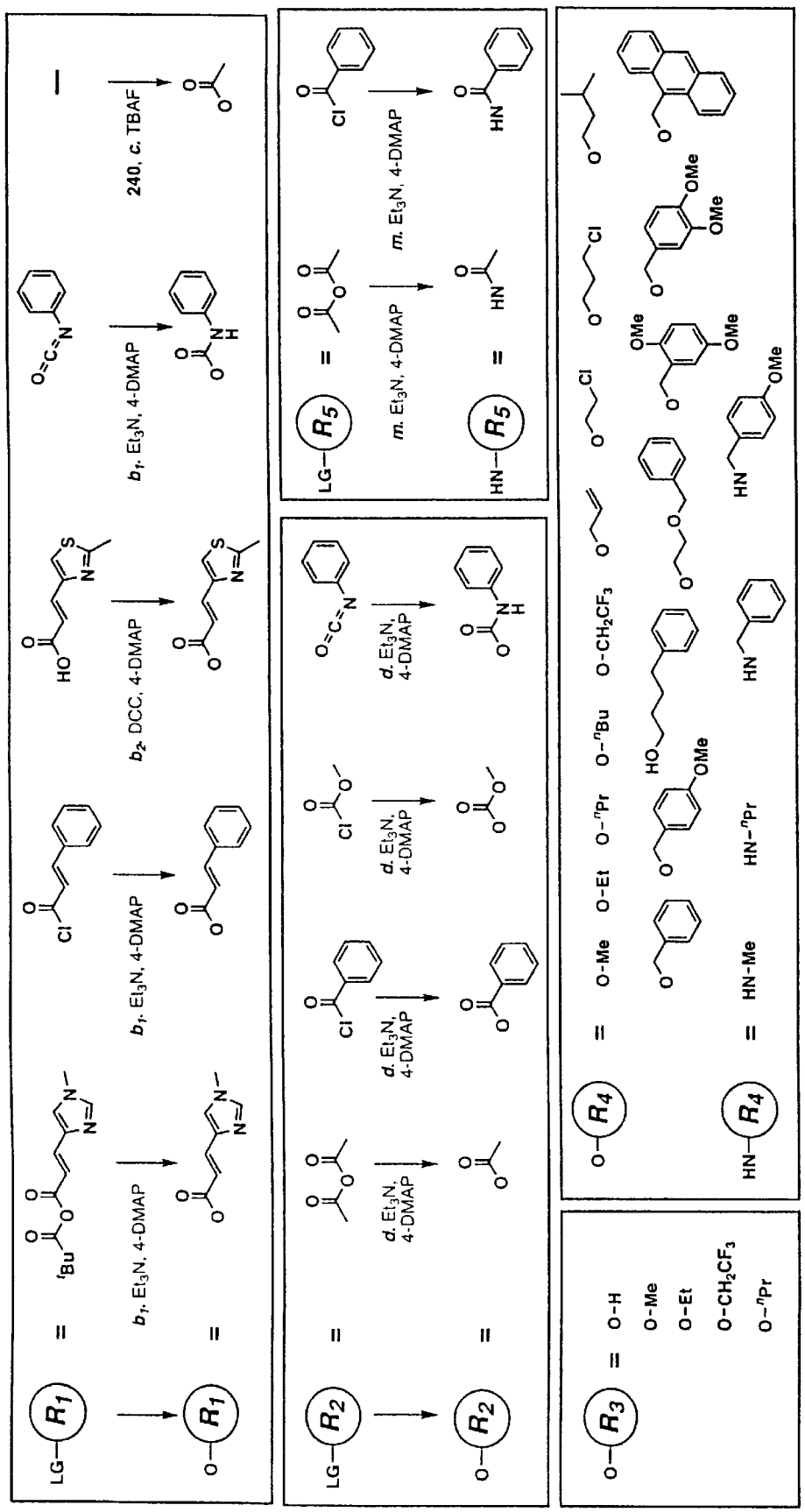

FIG. 18 illustrates the synthesis of a sarcodictyin library on solid phase. Reagents and conditions. a. NaOMe (5.0 equivalents), MeOH:THF (1:3), 25° C., 12 hours, >95%; b1. LG- R1 (5.0 equivalents), Et$_3$N (10 equivalents), 4-DMAP (2.0 equivalents), DMF, 50° C., 48 hours, 90–95%; b2. LG-R1 (10 equivalents), DCC (10 equivalents), 4-DMAP (2.0 equivalents), DMF, 50° C., 48 hours, 90–95%; c. TBAF (10 equivalents), THF, 25° C., 8 hours, >95%; d. LG-R2 (10 equivalents), Et3N (10 equivalents), 4-DMAP (2.0 equivalents), CH2Cl2, 25° C., 20 hours, 70–95%; e. PPTS (3.0 equivalents), MeOH, 25° C., 24 hours, 60–90%; f. Dess-Martin periodinane (5.0 equivalents), NaHCO$_3$ (15 equivalents), pyridine (15 equivalents), CH$_2$Cl$_2$, 25° C., 2 hours, 95%; g. NaClO$_2$ (25 equivalents), KH$_2$PO$_4$ (25 equivalents), 2-methyl-2-butene (50 equivalents), THF:tBuOH:H$_2$O (5:5:1) 25° C., 48 hours, >95%; h. HO-R4 (10 equivalents), DEAD (10 equivalents), Ph$_3$P (10 equivalents), THF, 0 to 25° C., 12 hours, >95%; i. H$_2$N-R4 (10 equivalents), DCC (10 equivalents), 4-DMAP (5 equivalents), DMF, 25° C., 20 hours, >95%; j. CSA (3.0 equivalents), HO-R3, 25° C., 15 hours, 60–90%; k. (PhO)$_2$PON$_3$ (10 equivalents), DEAD (10 equivalents), Ph$_3$P (10 equivalents), THF, 0 to 25° C., 4 hours, >95%; l. Ph$_3$P (10 equivalents), H$_2$O (30 equivalents), THF, 25° C., 8 hours, >95%; m. LG-R5 (10 equivalents), Et$_3$N (15 equivalents), CH$_2$Cl$_2$, 25° C., 10 hours, >90%. LG=leaving group; 4-DMAP=4-(dimethylamino)pyridine; TBAF=tetra-n-butylammonium fluoride; DEAD=diethylazodicarboxylate; DCC=dicyclohexylcarbodiimide; THF=tetrahydrofuran; DMF=dimethylformamide; dark circle=polystyrene.

Figure 19:
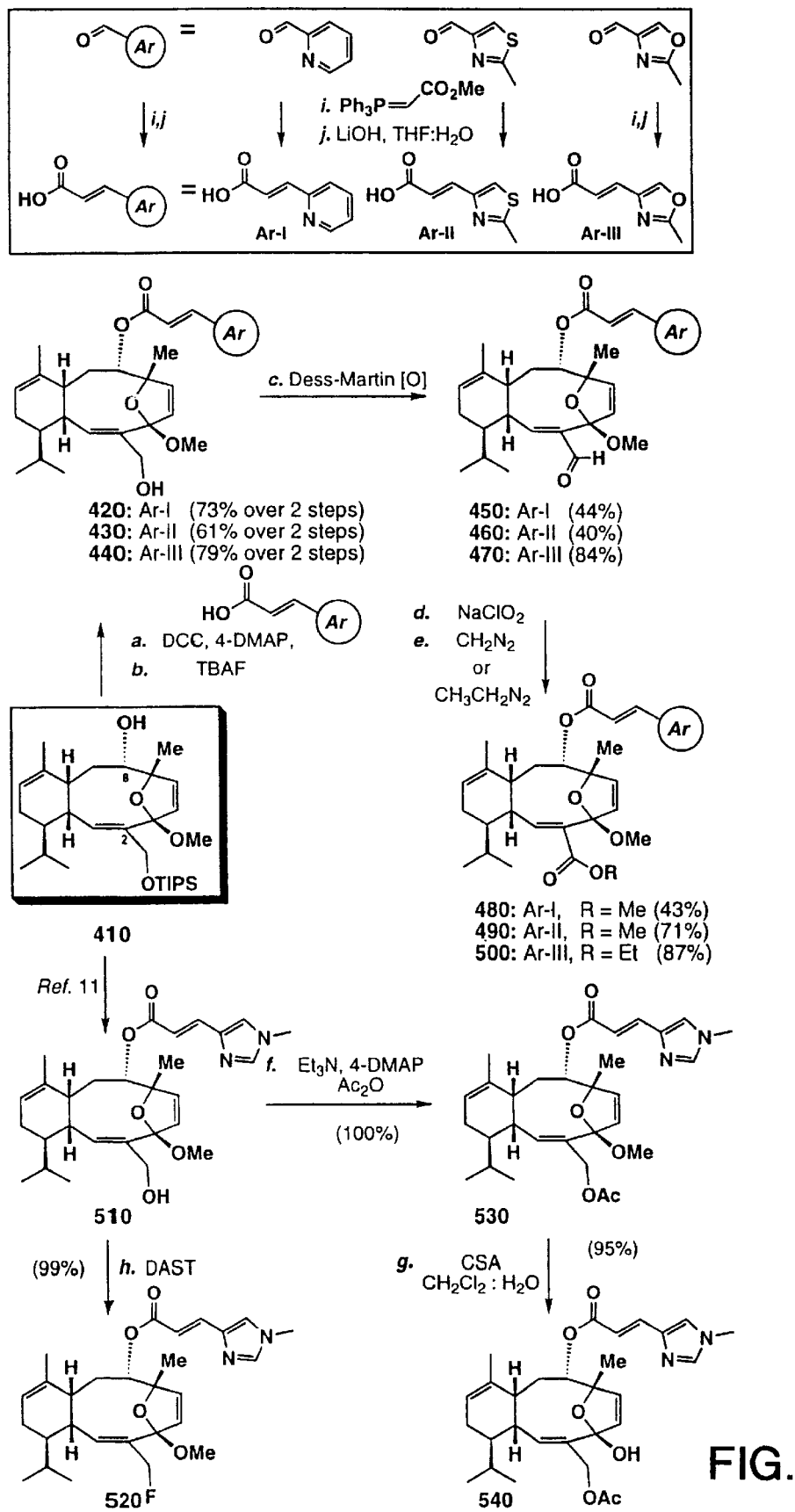

FIG. 19 shows the synthesis of sarcodictyin analogs 480–540 in solution. Reagents and conditions. a. acid Ar-I or Ar-II or Ar-III (1.3 equivalents), DCC (2.0 equivalents), 4-DMAP (0.5 equivalents), CH2Cl2 , 25° C., 36 hours; b. TBAF (2.0 equivalents), THF, 25° C., 1 hour, 73% for 420 over two steps, 61% for 430 over two steps, 79% for 440 over two steps; c. Dess-Martin periodinane (2.5 equivalents), NaHCO3 (ca. 10 equivalents), CH2Cl2, 25° C., 0.5 hours, 44% for 450, 40% for 460, 84% for 470; d. NaClO2 (6.0 equivalents), NaH$_2$PO$_4$ (3.0 equivalents), 2-methyl-2-butene (50 equivalents), THF:tBuOH:H$_2$O (5:5:1), 0° C., 2 hours; e. CH$_2$N$_2$ or CH$_3$CH$_2$N$_2$, 0° C., 10 min, 43% for 480 over two steps, 71% for 490 over two steps, 87% for 500 over two steps; f. Ac$_2$O (5.2 equivalents), Et$_3$N (6.8 equivalents), 4-DMAP (1.6 equivalents), CH$_2$Cl$_2$, 25° C., 2 hours, 100%; g. CSA (cat., 10% mol), CH$_2$Cl$_2$:H$_2$O (10:1), 25° C., 72 hours, 95%; h. DAST (2.0 equivalents), CH2Cl2, –78° C., 3 hours, 99%; i. Ph$_3$PCHCO$_2$Me (1.5 equivalents), benzene, 80° C., 95–98%; j. LiOH (3.0 equivalents), THF:H$_2$O (1:1). 25° C., 100%. DCC= dicyclohexylcarbodiimide; 4-DMAP=4-(dimethylamino)-pyridine; TBAF=tetra-n-butylammonium fluoride; THF= tetrahydrofuran; CSA=camphorsulfonic acid; DAST= diethylaminosulfur trifluoride.

Figure 20C:
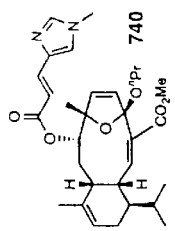

FIG. 20 tabulates various structures and tubulin polymerization properties of sarcodictyin analogs.

FIG. 21 tabulates cytotoxicity data of sarcodictyins with the following tubulin polymerization and cytotoxicity properties of sarcodictyins: (a) The tubulin polymerization measurements were performed at 37° C. except for adjustments in drug concentration (100 mM) and incubation time (90 min). (b) The cytotoxicity experiments were carried out as previously described (Giannakakou et al. *J. Biol. Chem.* 1995, 272, 17118–17125; Nicolaou et al. *Angew. Chem. Int. Ed. Engl.* 1997, 36, 2097–2103).

Figure 22:
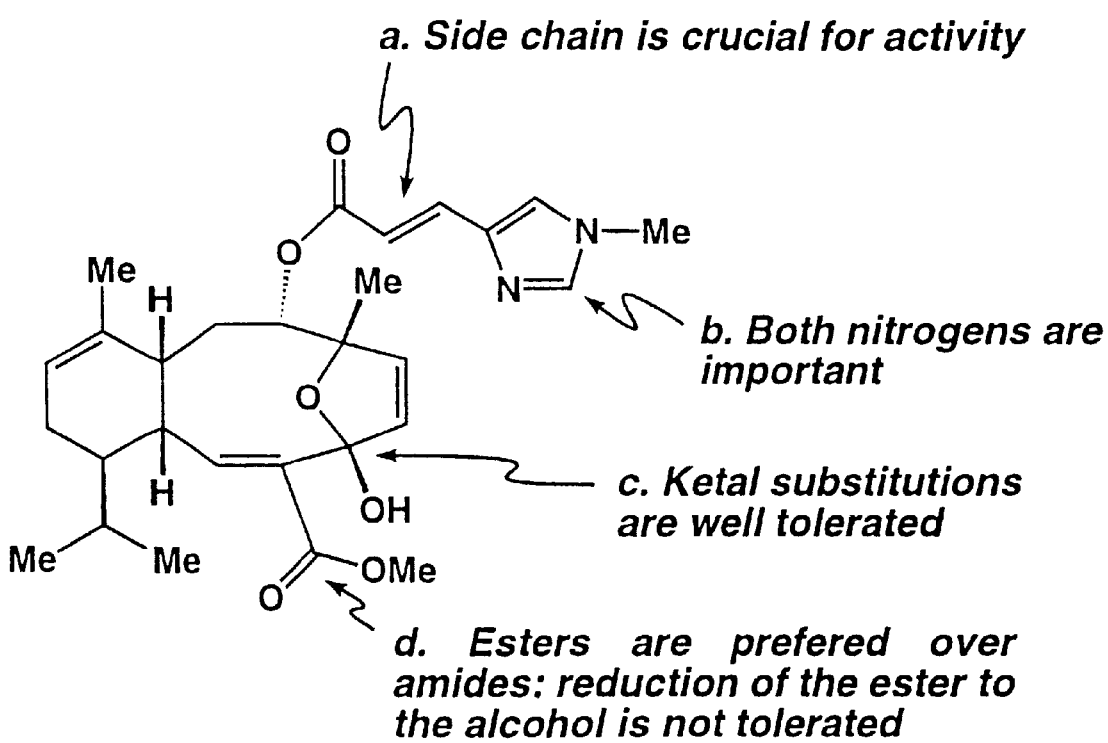

FIG. 22 shows stucture activity relationships (SARs) of sarcodictyins. a. Replacement of side chain with acetate, phenyl carbamate or cynamoyl ester is not tolerated. b. Replacement of the substituted imidazole heterocycle by a pyridine, thiazole or oxazole led to reduced activity. c. Methyl and ethyl ketals are well tolerated, whereas propyl or trifluoroethyl ketals are not. d. Esters are more active than the corresponding amides; substitution of the ester group is well tolerated; reduction of the ester to the alcohol and derivatives therof are not tolerated (except for the eleutherobin 4).

Figure 23:
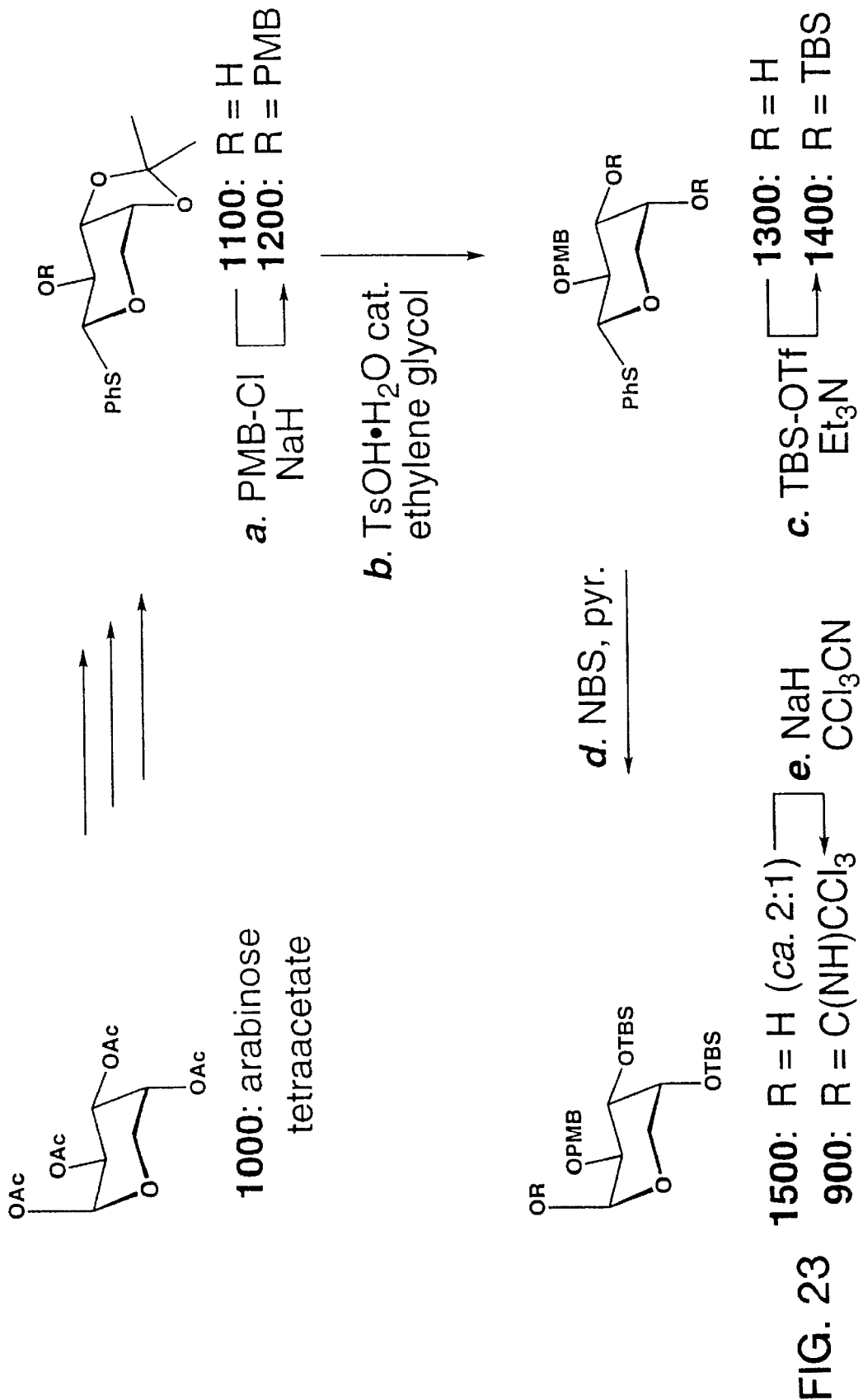

FIG. 23 shows the construction of glycoside donor 900. Reagents and conditions. (a) 1.1 equivalents of NaH, DMF, 0° C., 30 min; then 1.2 equivalents of PMB—Cl, 2 hours, 93%; (b) 0.1 equivalents of TsOH.H$_2$O, ethylene glycol-MeOH (1:10), 25° C., 6 hours, 84%; (c) 4.0 equivalents of TBS-OTf, 10 equivalents of Et3N, CH2Cl2, 0° C., 2 hours, 97%; (d) 3.4 equivalents of NBS, 11 equivalents of pyridine, acetone-H2O (93:7), 80% (ca. 2:1 ratio of anomers); (e) 0.1 equivalents of NaH, 5.0 equivalents of Cl3CCN, CH2Cl2, 25° C., 3.5 hours, 93%. Ts=p-toluenesulfonyl, TBSOTf= tert-butyldimethylsilyl trifluoromethanesulfonate, NBS=N-bromosuccinimide, PMB=p-methoxybenzyl.

Figure 24:
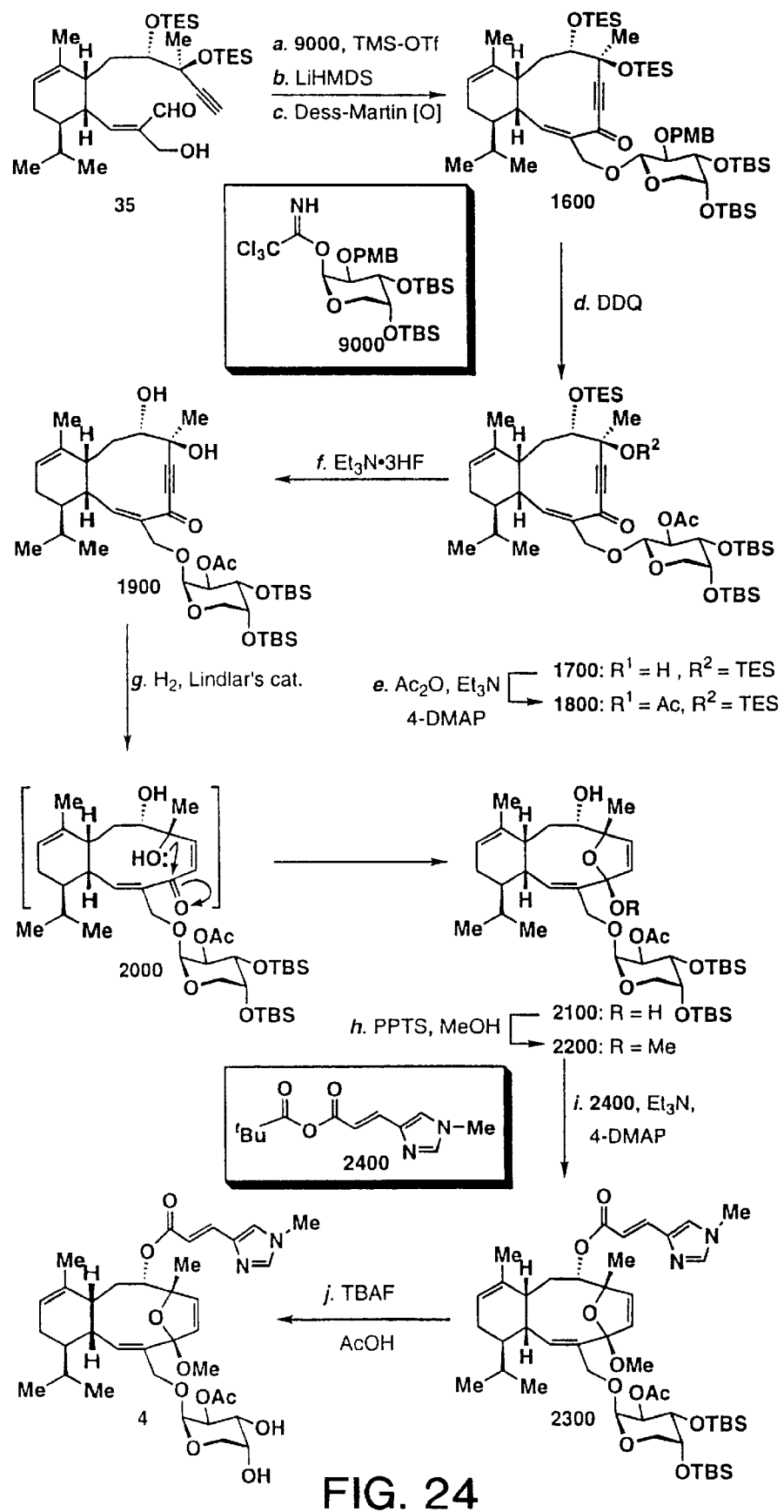

FIG. 24 shows the total Synthesis of eleutherobin (4). Reagents and conditions. (a) 900, TMS-OTf see FIG. 25; (b) 2.0 equivalents of LiHMDS, THF, –30° C., 20 min; (c) 2.0 equivalents of Dess-Martin periodinane, 10 equivalents of NaHCO3, 10 equivalents of pyridine, CH$_2$Cl$_2$, 0° C., 15 min, 93% for two steps; (d) 2.2 equivalents of DDQ, CH$_2$Cl$_2$:H$_2$O (20:1), 25° C., 91%; (e) 12 equivalents of Ac$_2$O, 16 equivalents of Et$_3$N, 0.5 equivalents of 4-DMAP, CH$_2$Cl$_2$, 25° C., 1 hour, 95%; (f) Et$_3$N.3HF:THF (1:7), 25° C., 3 hours, 81%; (g) H$_2$, 50 mol% Lindlar's catalyst, PhCH$_3$, 25° C., 20 min; (h) 0.2 equivalents of PPTS, MeOH, 25° C., 20 min, 76% for two steps; (i) 10 equivalents of 2400, 15 equivalents of Et3N, 2.0 equivalents of 4-DMAP, CH$_2$Cl$_2$, 25° C., 18 hours, 97%; (j) 17 equivalents of TBAF, 4.0 equivalents of ACOH, THF, 25° C., 2.5 hours, 96%. TMSOTf=trimethylsilyl trifluoromethane sulfonate, LiHMDS=lithium hexamethyl-disilazane, DDQ=2,3-dichloro-5,6-dicyano- 1,4-benzoquinone, 4-DMAP=4-dimethyl-aminopyridine, Lindlar's catalyst=Pd/CaCO$_3$/Pb, PPTS=pyridinium p-toluene sulfonate, TBAF=tetra-n-butylammonium fluoride.

Figure 25:
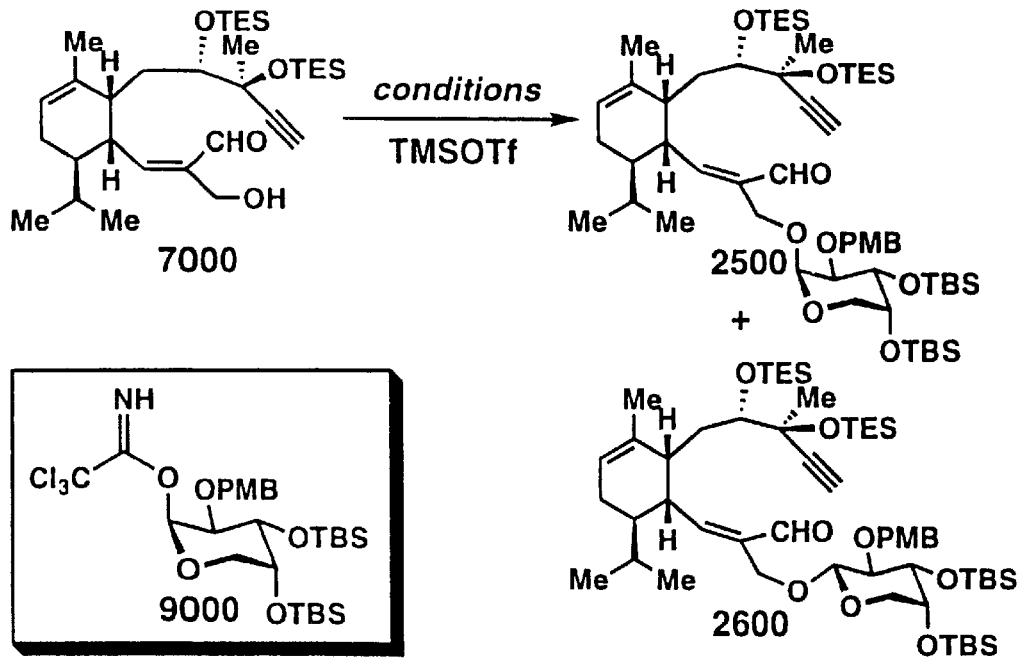

FIG. 25 shows key intermediate conditions towards the total synthesis of eleutherobin (4). Studies for the attachment of the sugar moiety.a. concentration of starting material is 0.1 M, TMSOTf (2–5%), 1.5 equivalents of imidate; b. concentration of starting material is 0.07 M, TMSOTf (2–5%), 2.5 equivalents of imidate; c. The ratio of the two anomers was determined by NMR. TES=triethylsilyl, PMB= p-methoxybenzyl, TBS=t-butyldimethylsilyl, NIS=N-iodosuccinimide.

Figure 26:
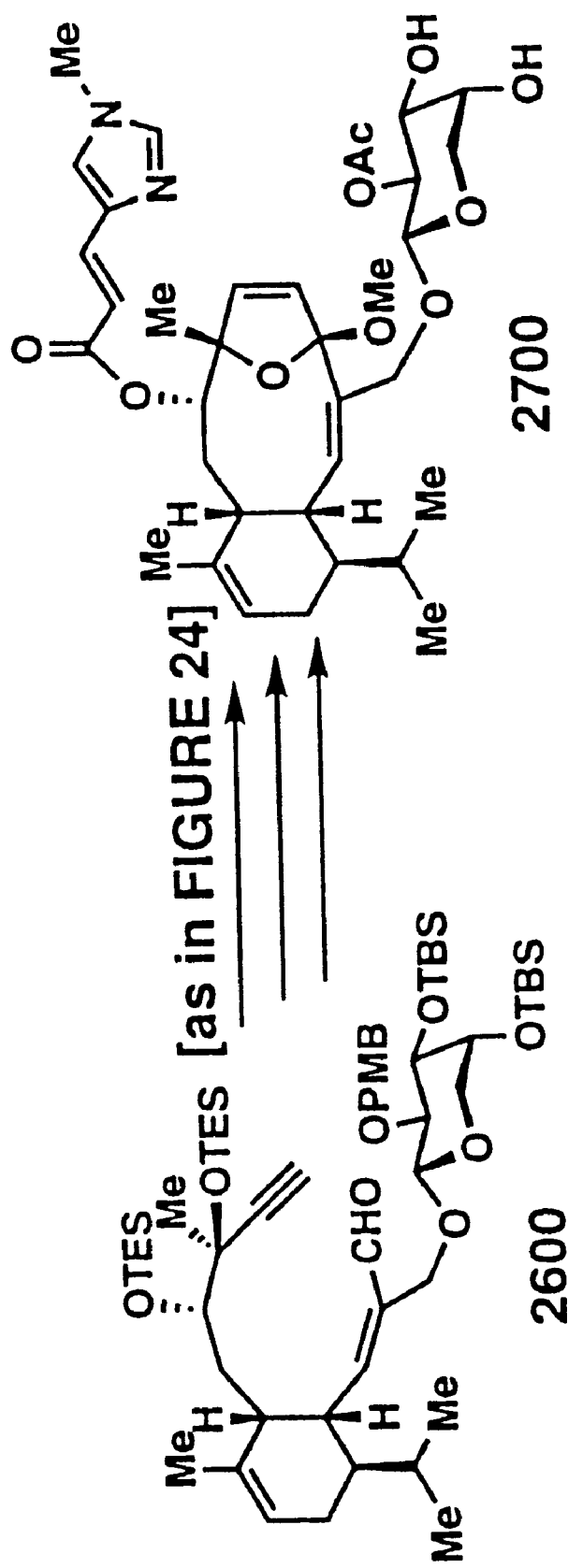

FIG. 26 shows the synthesis of the α-anomer of eleutherobin (2700).

FIG. 26 shows the conversion of 2600 to 2700.

Figure 27:
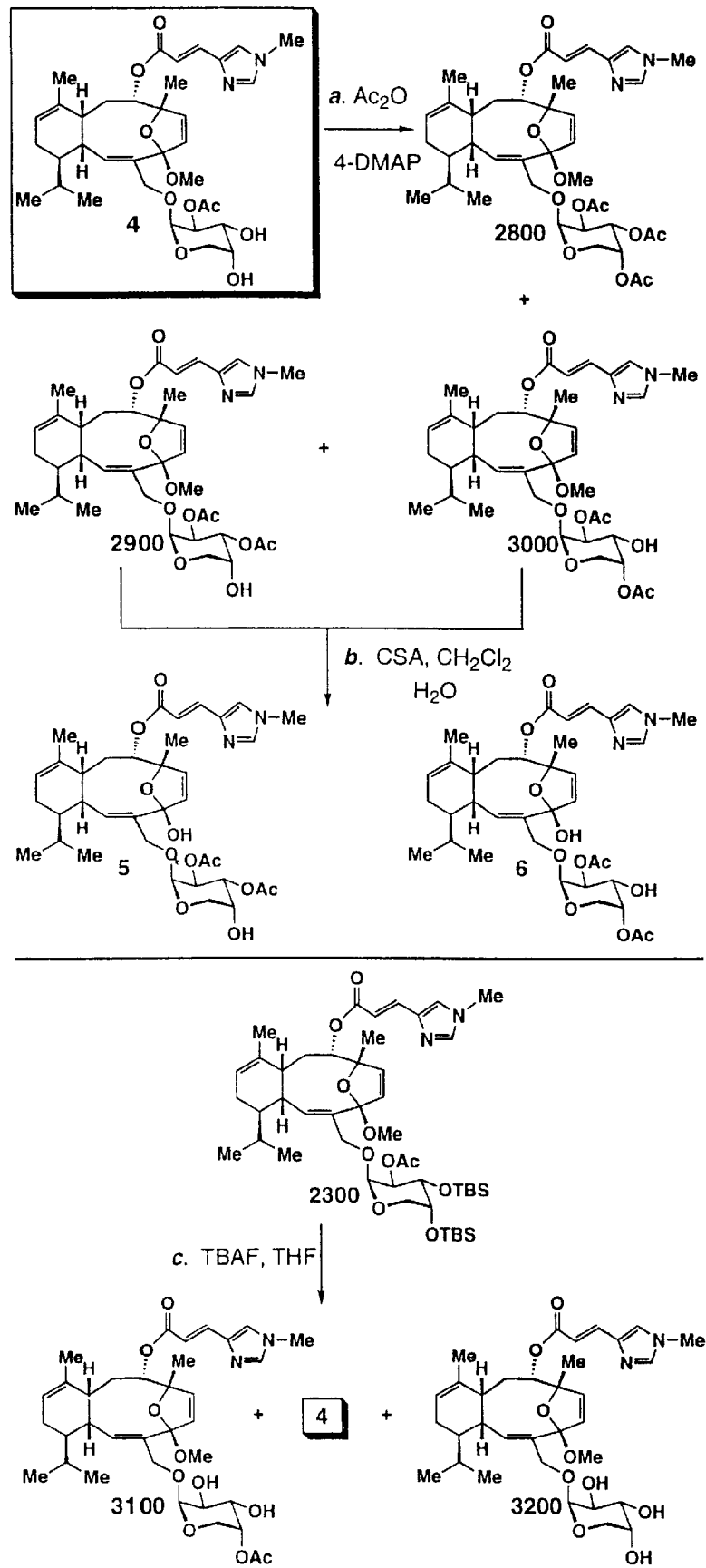

FIG. 27 shows the synthesis of eleuthosides A (5) and B (6). Reagents and conditions. (a) 1.1 equivalents of Ac$_2$O, 3.0 equivalents of Et$_3$N, 0.2 equivalents of 4-DMAP, 0° C., 1 hour, 16% of 2800 along with 73% of the mixture of 2900 and 3000 (2.2:1 by NMR); (b) 2.0 equivalents of CSA, CH2Cl2 :H2O (10:1), 25° C., 48 hours, 80% of the mixture of 5 and 6 (based on 87% conversion of the starting material); (c) 4.0 equivalents of TBAF, THF, 25° C., 6 hours, 4 (22%), 3100 (60%) and 3200 (8%). 4-DMAP=4-dimethylaminopyridine, CSA=10-camphorsulfonic acid.

Figure 28:
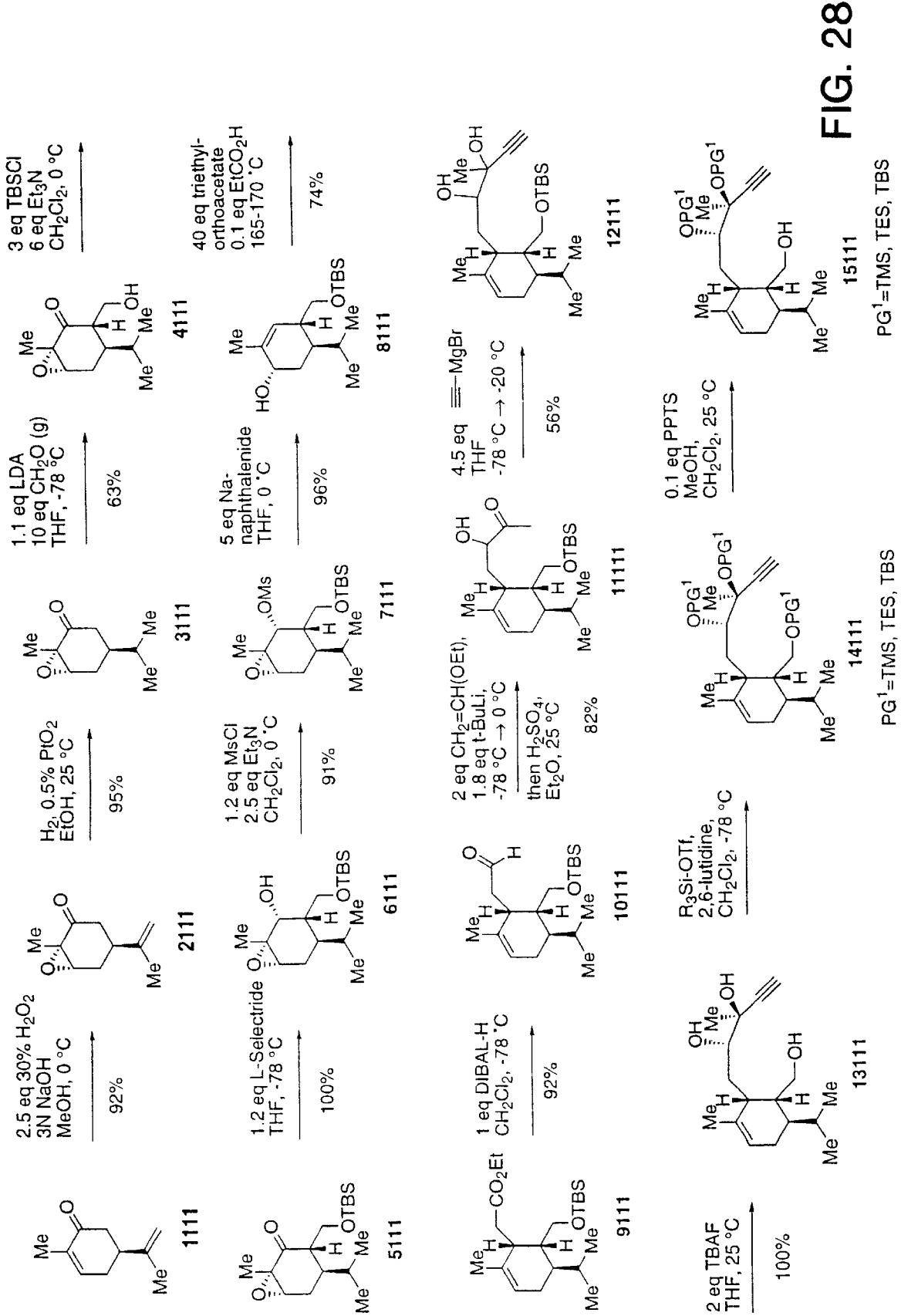

FIG. 28 shows a general synthesis of an eleutherobin core intermediate 15111.

Figure 29:
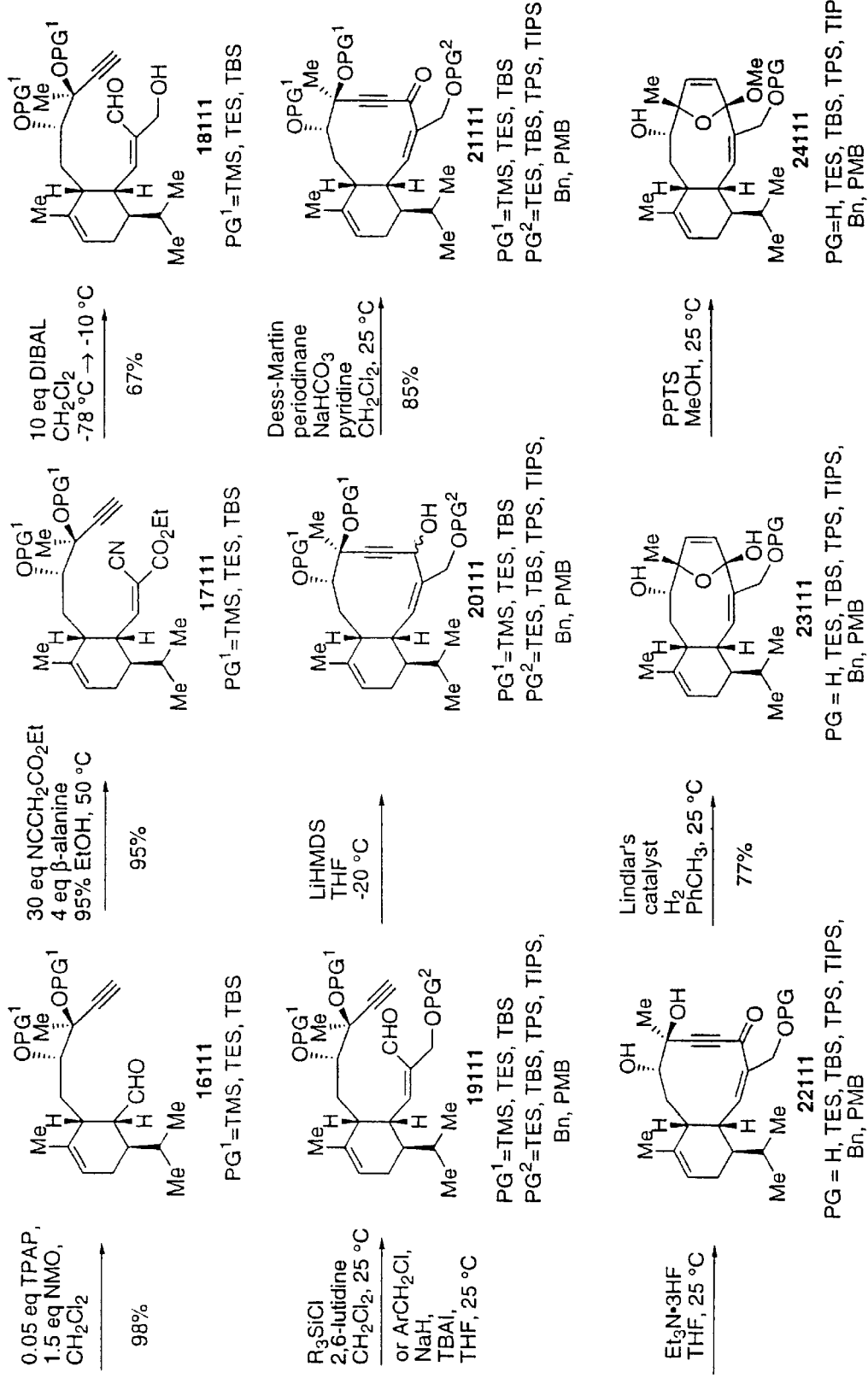

FIG. 29 shows a general synthesis of an eleutherobin core 24111.

Figure 30A:
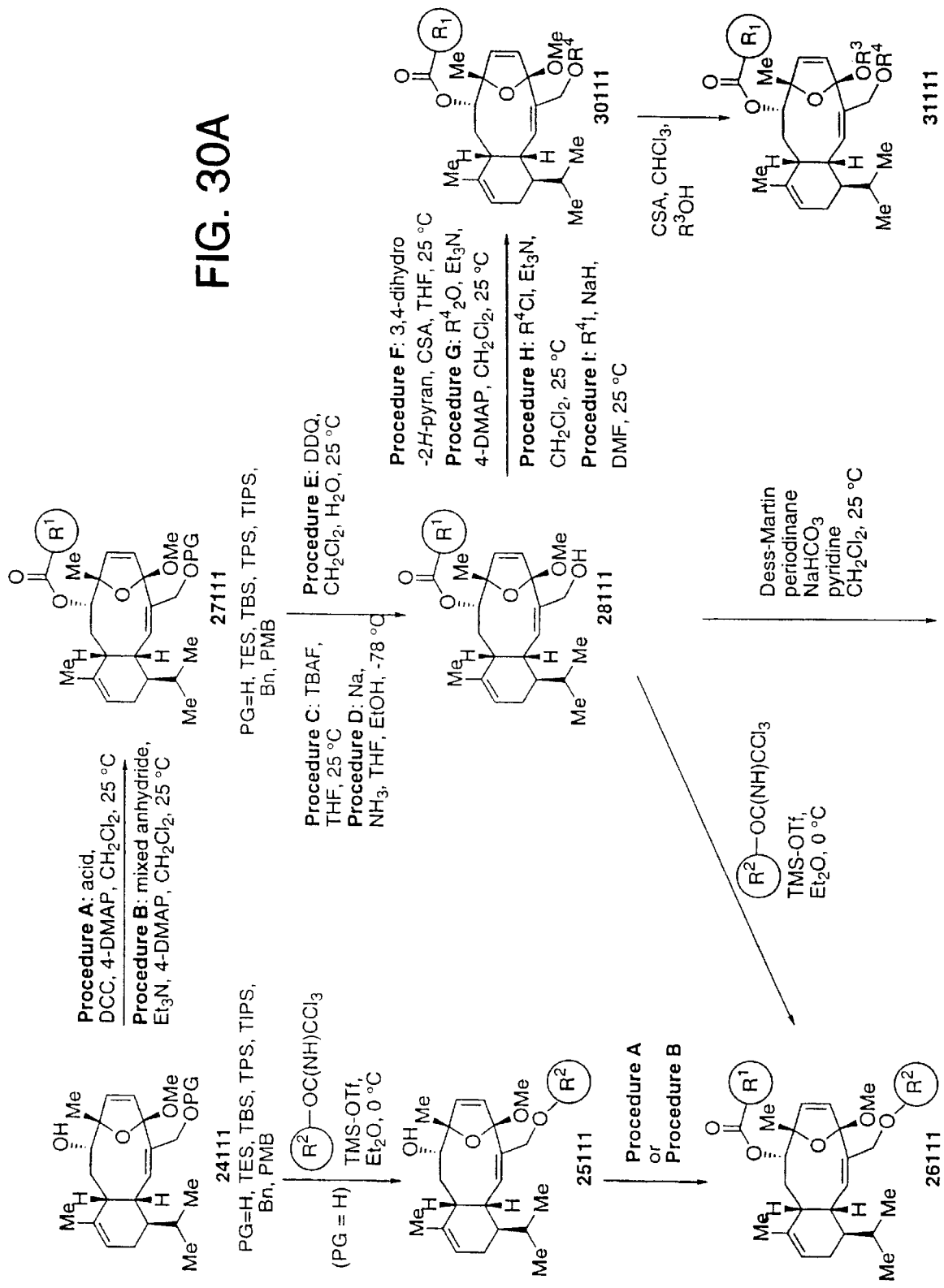
Figure 30B:
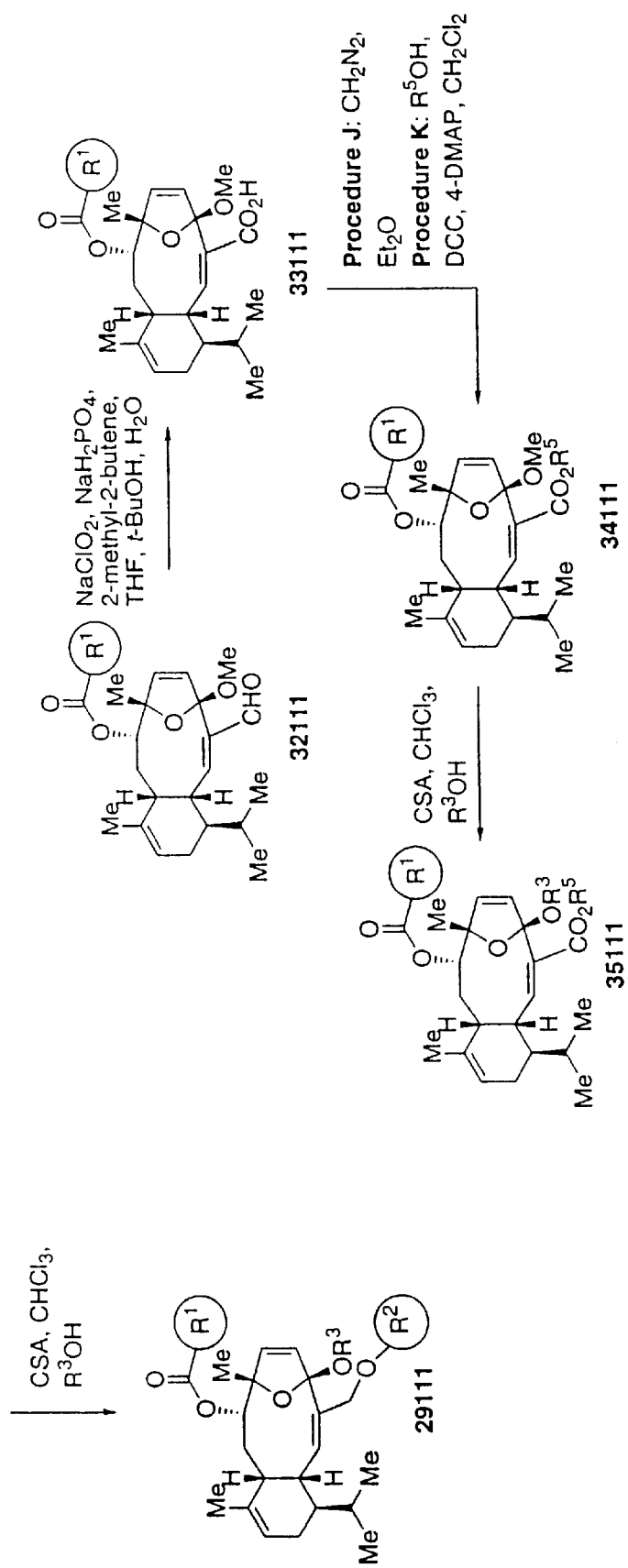
Figure 32:
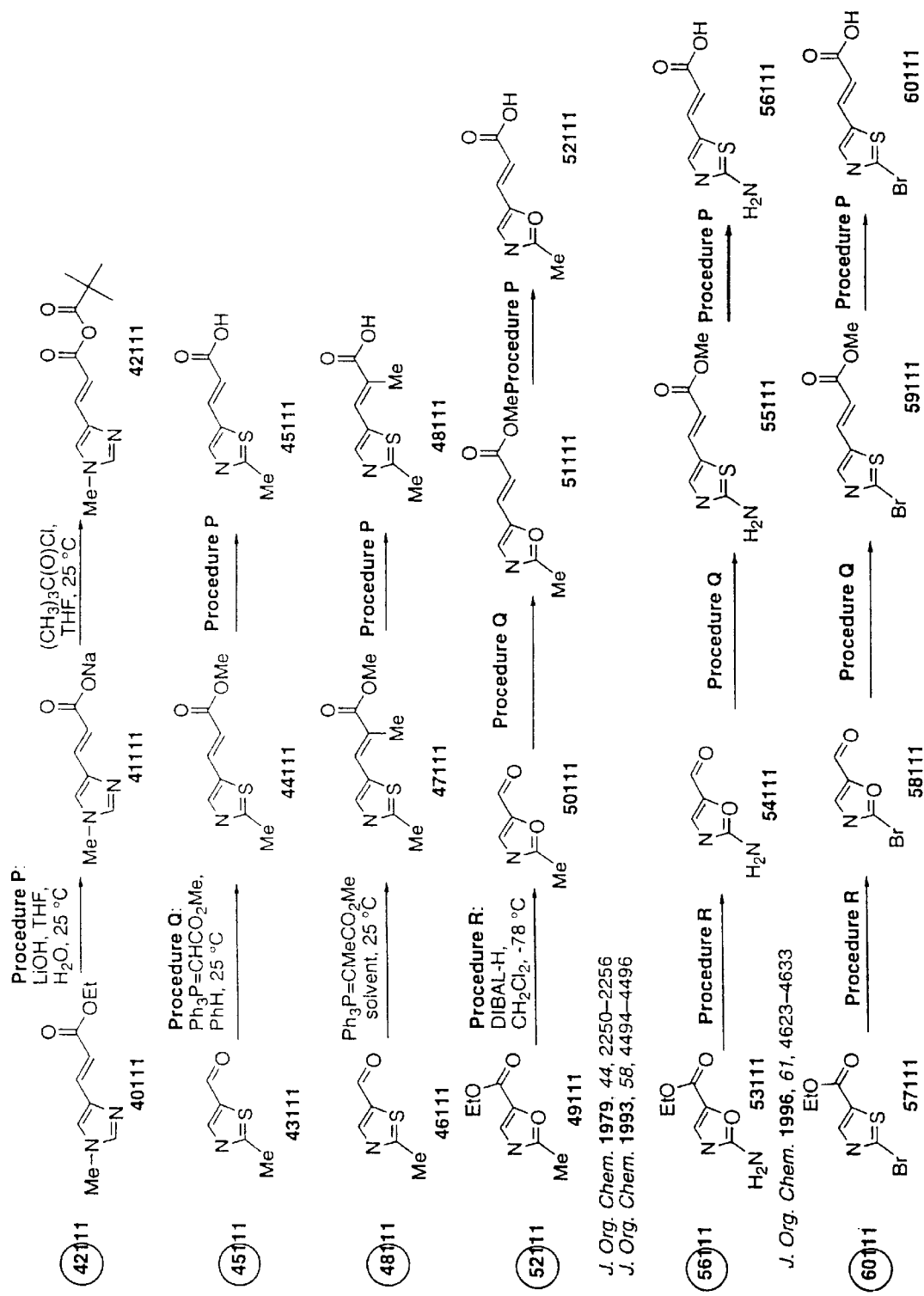
Figure 33:
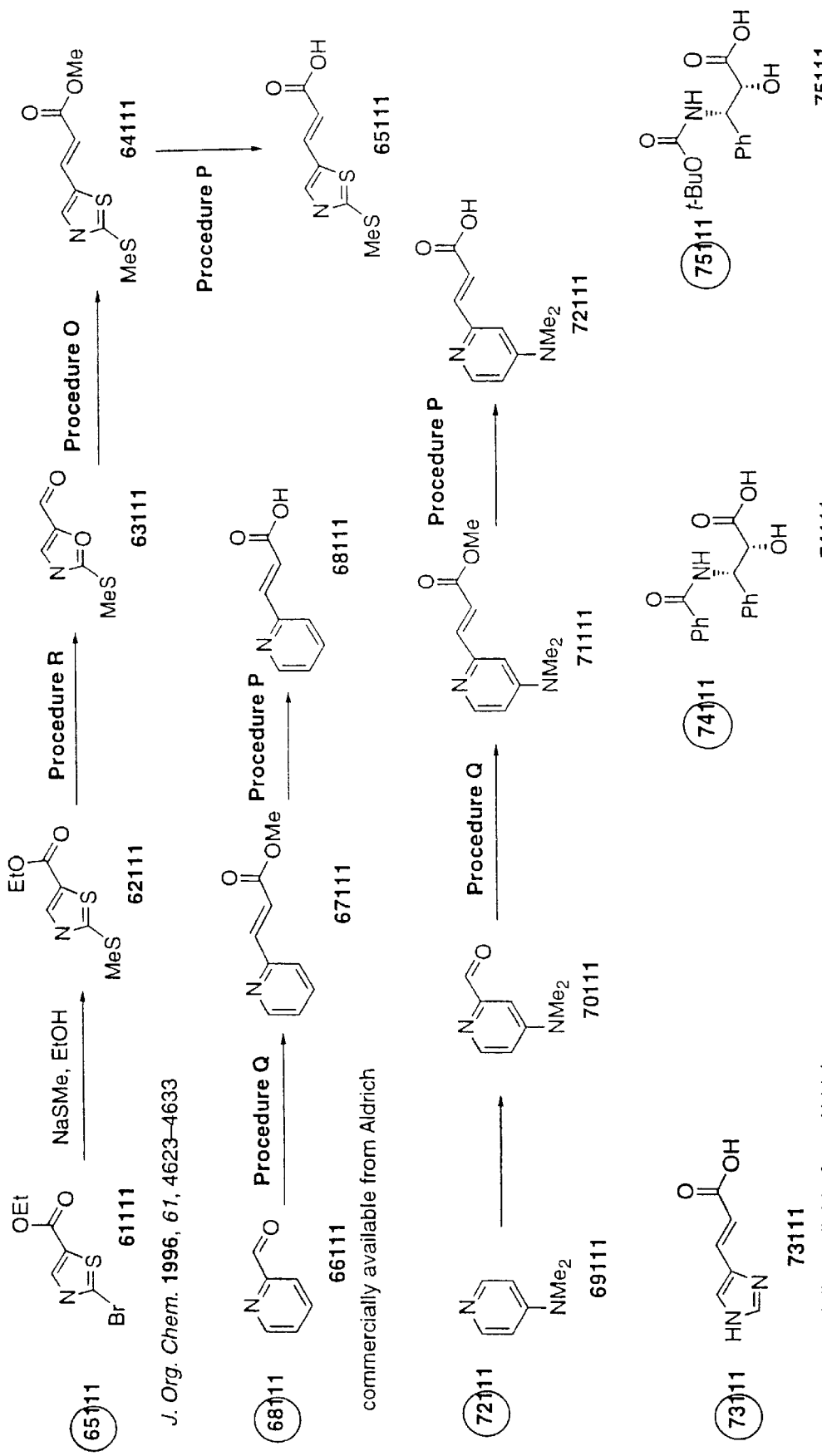

FIG. 30 illustrates the introduction of side-chains and synthesis of sarcodictyin and analogs wherein $R_1$ is represented by the products formed in FIGS. 32 and 33; $R_2$ is represented by the products formed in FIGS. 34; $R_3$ comprises a radical from the group of H, Me, Et, n-Pr, i-Pr, n-Bu, tBu, Bn, $CH_2CH=CH_2$, $CH_2CCH$, c—$C_6H_{11}$, $C_8H_{17}$, and $HO(CH_2)_2$; $R_4$: THP, Ac, 2—Cl—Ac, $CCl_3C(O)$, 2-Br—Ac, $CF_3C(O)$, 2-PhAc, EtC(O), $CH_2=CHC(O)$, HCCC(O), n-PrC(O), i-PrC(O), c-PrC(O), n-BuC(O), i-BuC(O), t-BuC(O), Lev, c—$C_6H_{11}$C(O), Bz, 2-furylC(O), PhCH=CHC(O), 2-thiopheneC(O), Me, Et, n-Pr, i-Pr, All, Prop, n-Bu, Bn, $AcOCH_2CH_2$; $R_5$: H, Me, Et, n-Pr, i-Pr, n-Bu, t-Bu, Bn, CH2CH=CH2, CH2CCH, c—$C_6H_{11}$, $C_8H_{17}$.

Figure 31:
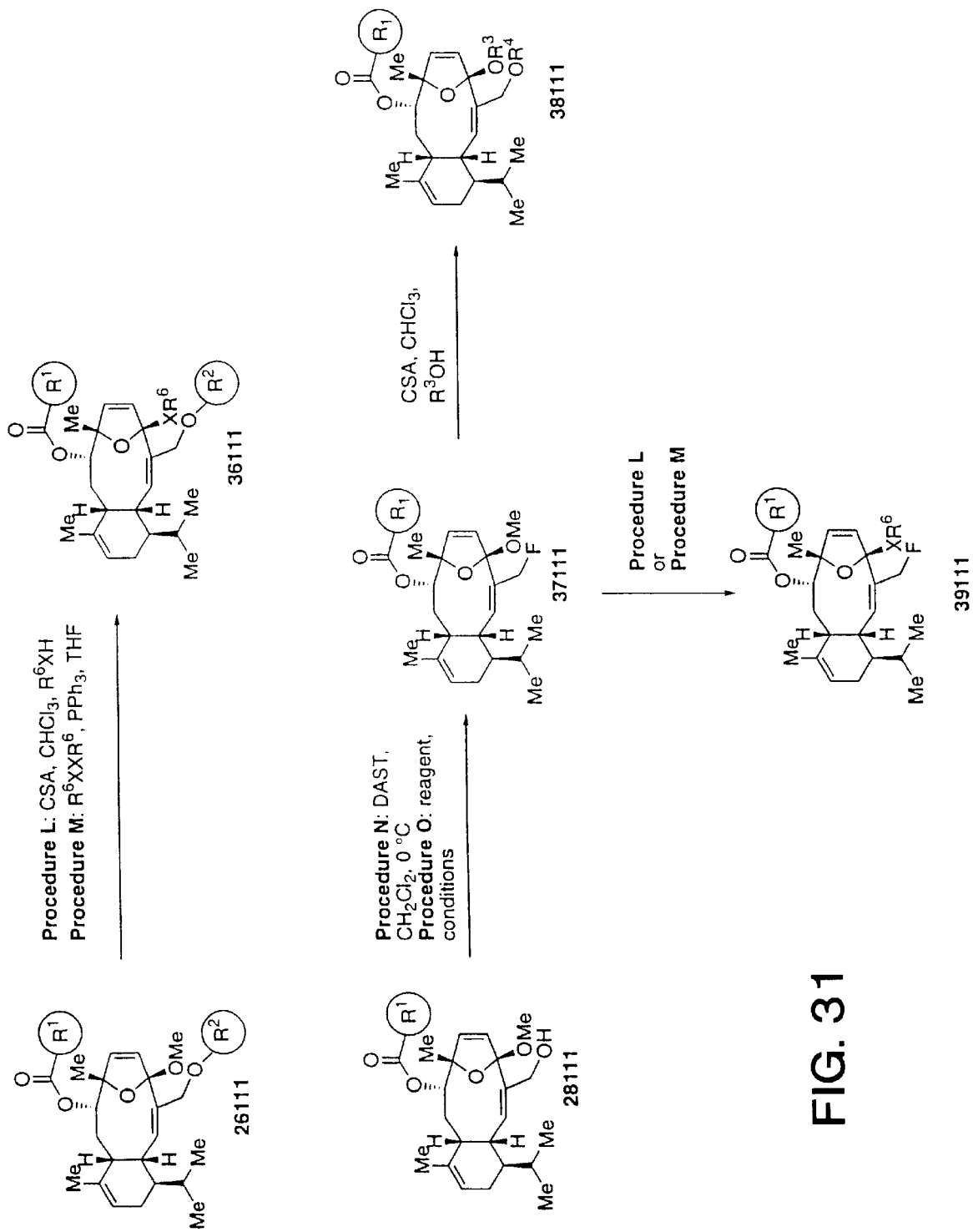

FIG. 31 illustrates further eleutherobin and sarcodictyin analogs wherein $XR_6$ is a radical selected from a group consisting of MeHN, $Me_2N$, EtHN, $Et_2N$, n-PrHN, n-$Pr_2$N, i-PrHN, i-$Pr_2$N, n-$BU_2$N, BnHN, $Bn_2$N, HS, MeS, EtS, n-PrS, i-PrS, n-Bu, PhS, and BnS.

FIG. 31 illustrates the conversion of 26111 to 36111, the conversion of 28111 to 37111, and the conversion of 37111 to 38111 and 39111.

FIG. 32 illustrates the synthesis of $R_1$ side-chain acids and anhydrides.

FIG. 33 continues to illustrate the synthesis of $R_1$ side-chain acids and anhydrides.

Figure 34A:
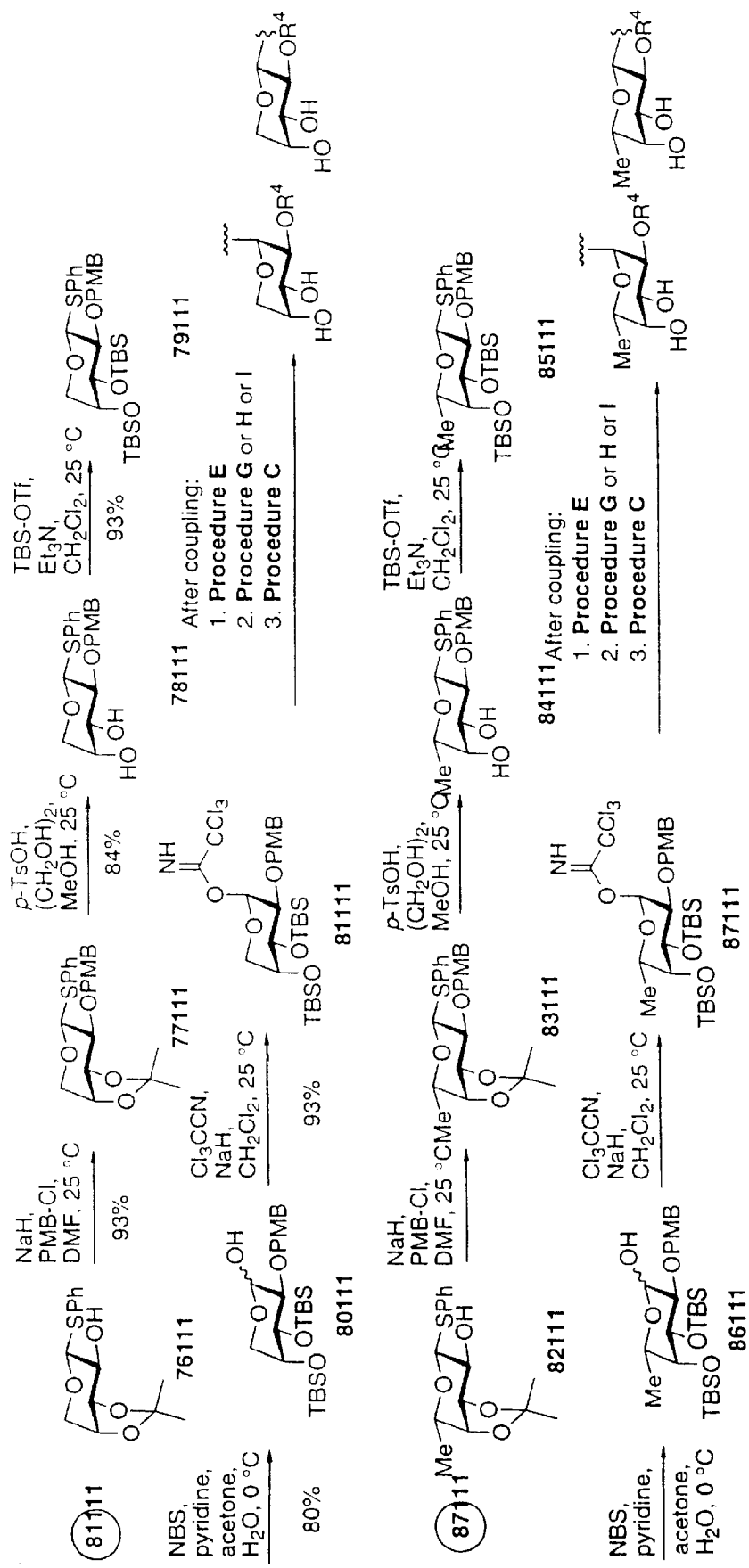
Figure 34B:
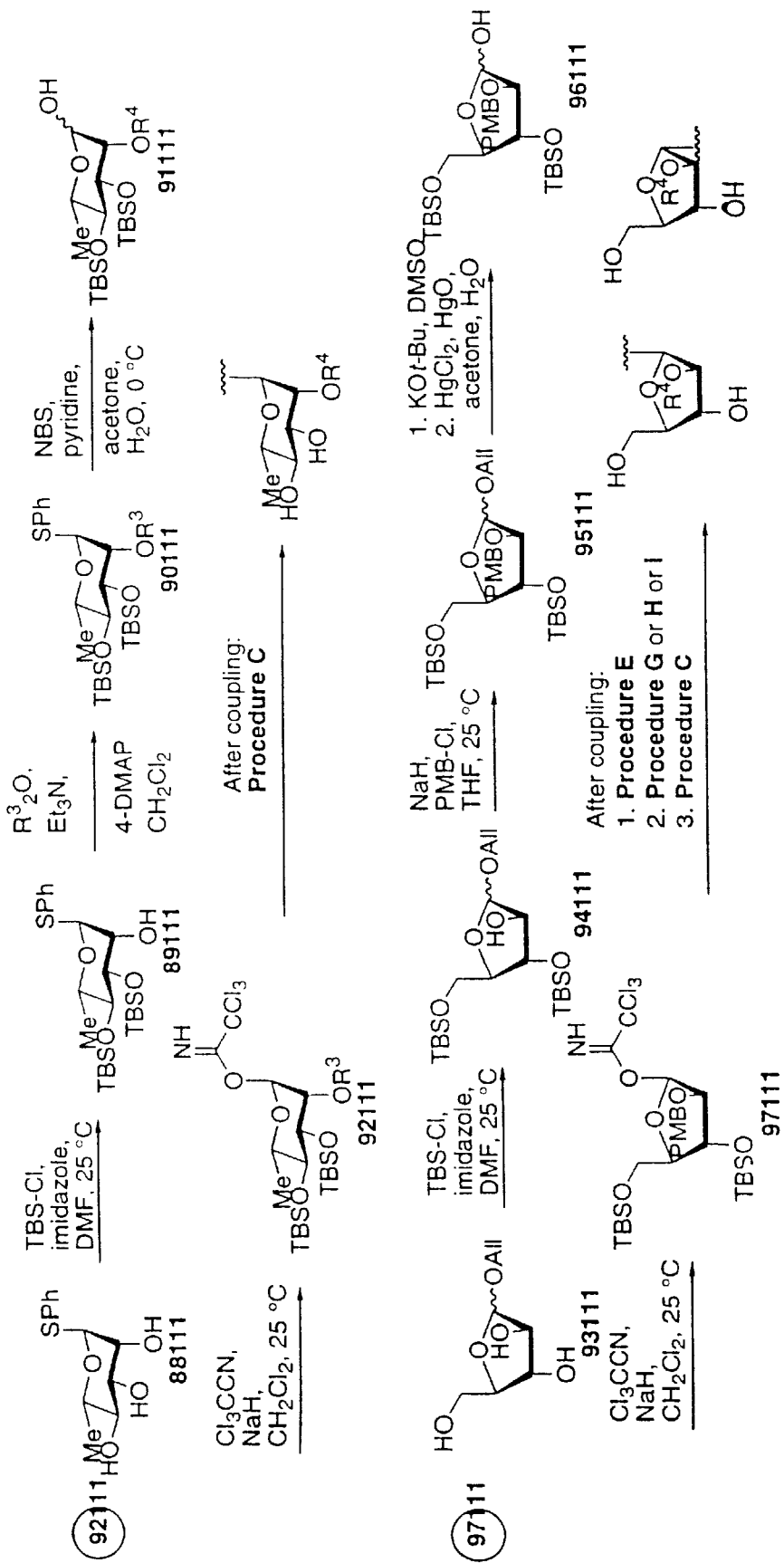

FIG. 34 illustrates the synthesis of the $R_2$ side-chain imidates, and the projected steps after coupling wherein $R_4$ is selected from Ac, 2—Cl—Ac, $CCl_3C(O)$, 2-Br—Ac, $CF_3C(O)$, 2-PhAc, EtC(O), $CH_2=CHC(C)$, HCCC(O), n-PrC(O), i-PrC(O), c-PrC(O), n-BuC(O), i-BuC(O), t-BuC(O), Lev, c—$C_6H_{11}$C(O), Bz, 2-furylC(O), PhCH=CHC(O), and 2-thiopheneC(O).

DETAILED DESCRIPTION OF THE INVENTION

The present invention relates to sarcodictyin A and B, eleutherobin, sarcodictyin analogs, eleutherobin analogs, libraries of both sarcodictyin and eleutherobin analogs, and methods for producing such compounds using solid phase and solution phase chemistries. The invention is directed analogs derived from the total synthesis of sarcodictyns A and B, eleutherobin and eleuthosides A (5) and B (6), the absolute stereochemistry of eleutherobin (4), and the construction of a number of analogs of these compounds. A further embodiment of the invention is directed to solid phase chemistry that provides the generation of a combinatorial sarcodictyin library and its biological evaluation leading to the discovery of analogs possessing higher antitumor potencies than those of the natural products. The gained knowledge provides important information regarding the structure activity relationships within the sarcodictyin-eleutherobin molecular framework and sets the stage for further advances in the field.

EXAMPLE I

Total Synthesis of Sarcodictyins A and B

Figure 6:
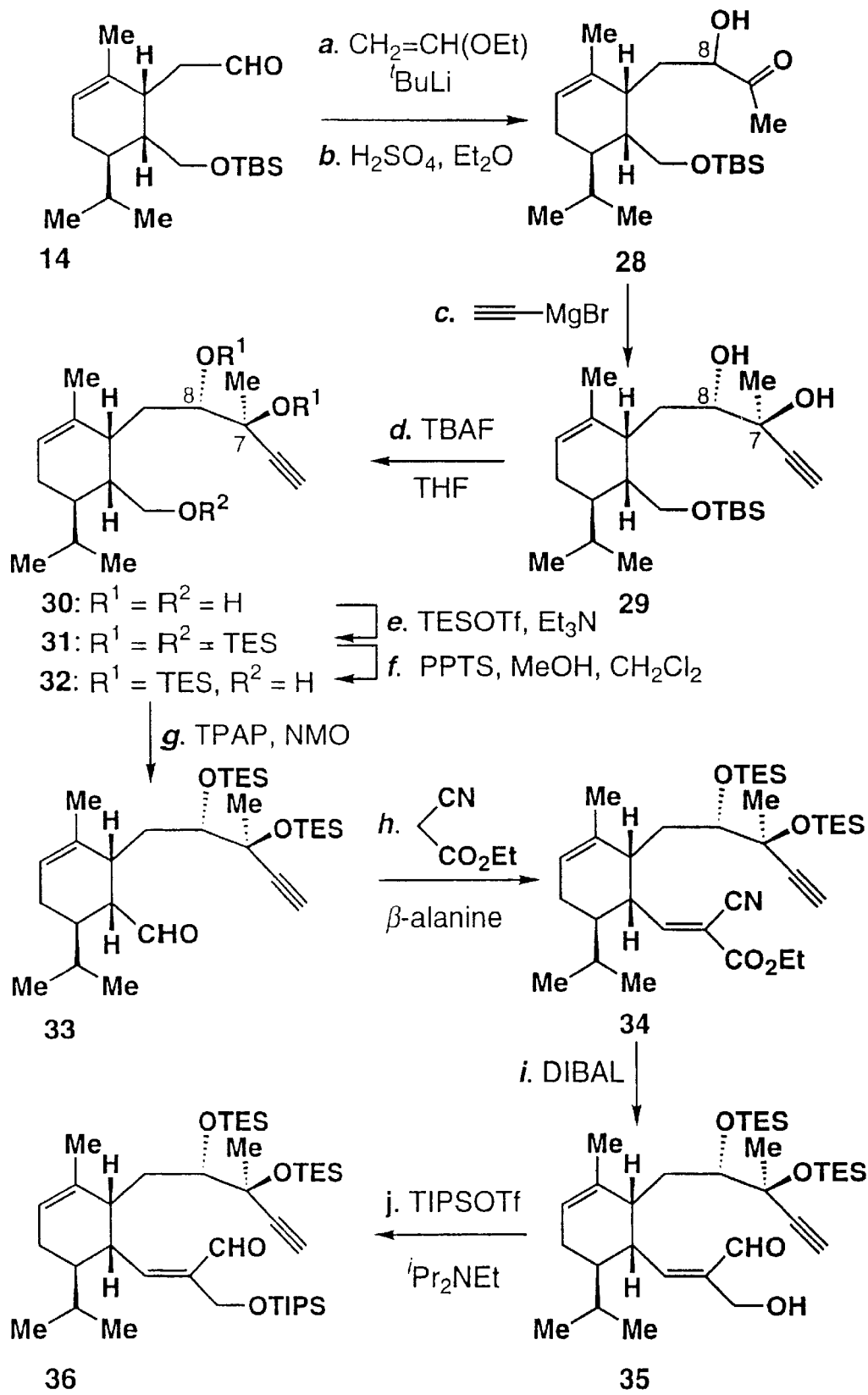
FIG. 6 illustrates the second generation synthesis of acetylene-aldehyde compound 36. Reagents and conditions. a. 2.0 equivalents of $CH_2$=CH(OEt), 1.8 equivalents of tBuLi (1.7 M in THF), THF, −78 to 0° C., 1 hour; then cool to −78° C. and add 14 in THF; then slowly warm to −40° C.; b. conc. $H_2SO_4$, $Et_2O$, 25° C., 2 min, 82% for two steps as a ca. 1.25:1 mixture of diastereoisomers; c. 5.0 equivalents of ethynylmagnesium bromide (0.5 M in THF), THF, −78 to 20°° C., 14 hours, 76%, 29 (43%) plus 7,8-diastereoisomer (33%); d. 29, 2.0 equivalents of TBAF (1.0 M in THF), THF, 0 to 25° C., 1 hour, 92%; e. 5.0 equivalents of TESOTf, 10 equivalents of $Et_3N$, $CH_2Cl_2$, 25° C., 2 hours, 100%; f. 0.1 equivalents of PPTS, MeOH:$CH_2Cl_2$, (3:1), 25° C., 45 min, 98%; g. 0.05 equivalents of TPAP, 1.5 equivalents of NMO, $CH_2Cl_2$, 4 Å MS, 1.5 hours, 98%; h. 30 equivalents of ethyl cyanoacetate, 4.0 equivalents of β-alanine, 95% EtOH, 72 hours, 50° C., 95%; i. 10 equivalents of DIBAL, hexanes, −78° C. for 6 hours, then −40° C. for 1 hour, then −10° C. for 1 hour, 90%; j. 5.0 equivalents of TIPSOTf, 10 equivalents of $iPr_2NEt$, $CH_2Cl_{21}$ −78° C., 1 hour, 93%. THF= tetrahydrofuran, TBAF=tetra-n-butylammonium fluoride, TESOTf=triethylsilyl trifluoromethanesulfonate, PPTS= pyridinium p-toluenesulfonate, TPAP=tetra-n- propylammonium perruthenate, NMO=4-methylmorpholine N-oxide, MS=molecular sieves, DIBAL=diisobutylaluminum hydride, TIPSOTf=triisopropylsilyl trifluoromethane sulfonate.

This example provides the total synthesis of cytotoxic marine natural products possessing tubulin polymerization and microtubule stabilization properties, sarcodictyins A (7) and B (8). Two related approaches to these target molecules have been developed, both utilizing (+)-carvone (9) as starting material. The first approach involves a stereoselective construction of acetylenic aldehyde 27 (FIG. 4) while the second approach proceeds through a more direct but less selective sequence to the similar intermediate 36 (FIG. 6). Both strategies involve ring closures of the acetylenic aldehyde precursors to 10-membered rings under basic conditions followed by elaboration and selective reduction of the acetylenic linkage to a cis double bond. This promotes bridging to form the required tricyclic skeleton of the sarcodictyins (27-37-38-39-4, FIG. 7 and 37-44-45-46-47-42, FIG. 9) and (36-4-45, FIG. 10). Installation of the (E)-N(6')-methylurocanic acid residue was achieved by esterification with mixed anhydride 52, while the C-3 ester moieties were installed by standard deprotection, oxidation, and esterification procedures.

Retrosynthetic Analysis and Strategy

The general structures of sarcodictyins (I, FIG. 2) are characterized by a rigid tricyclic framework from which a number of appendages branch out. Prominent amongst these appendages are the carboxylate group at C-3, the hydroxyl group at C-4, and the ester group at C-8 carrying the (E)-N(6)-methylurocanic acid residue. The bridging oxygen involved in the lactol functionality at C-4 allows a strategic disconnection that unravels the [6.2.1]-bicyclic structure of I into the 10-membered ring II. The latter structure is expected to spontaneously collapse back into I in the synthetic directions. The 5,6-cis-double bond in II can be derived from the corresponding acetylene moiety whose disconnection at C4–C5 via a retro acetylide-aldehyde addition leads to open-chain acetylenic aldehyde III. Two further disconnections, indicated in structure III through retro acetylide-ketone addition and Knoevenagel condensation, furnish intermediate IV whose structure is highly suggestive of (+)-carvone (9).

This retrosynthetic analysis led to a strategy whose execution resulted in efficient total synthesis of both sarcodictyins A (7) and B (8). The sequence can be divided in three subsequences: the construction of the key cyclization precursors, the cyclization and formation of the tricyclic framework and the construction of the remaining side-chains.

Construction of Cyclization Precursors 27 and 36

Figure 2:
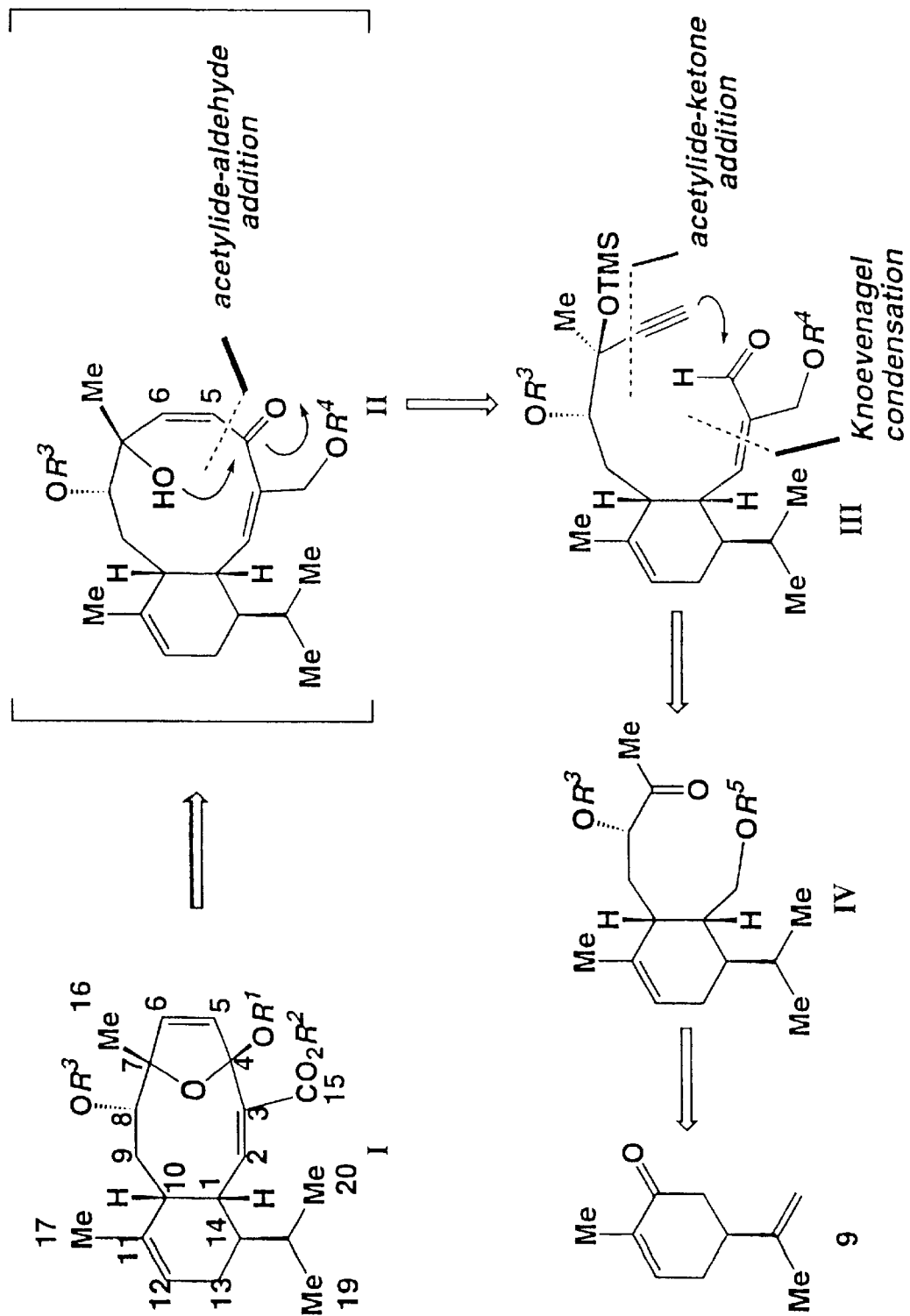
FIG. 2 shows the retrosynthetic analysis of the core structure of eleutherobin (4), eleuthosides A (5) and B (6) and sarcodictyins A (7) and B (8).
Figure 3:
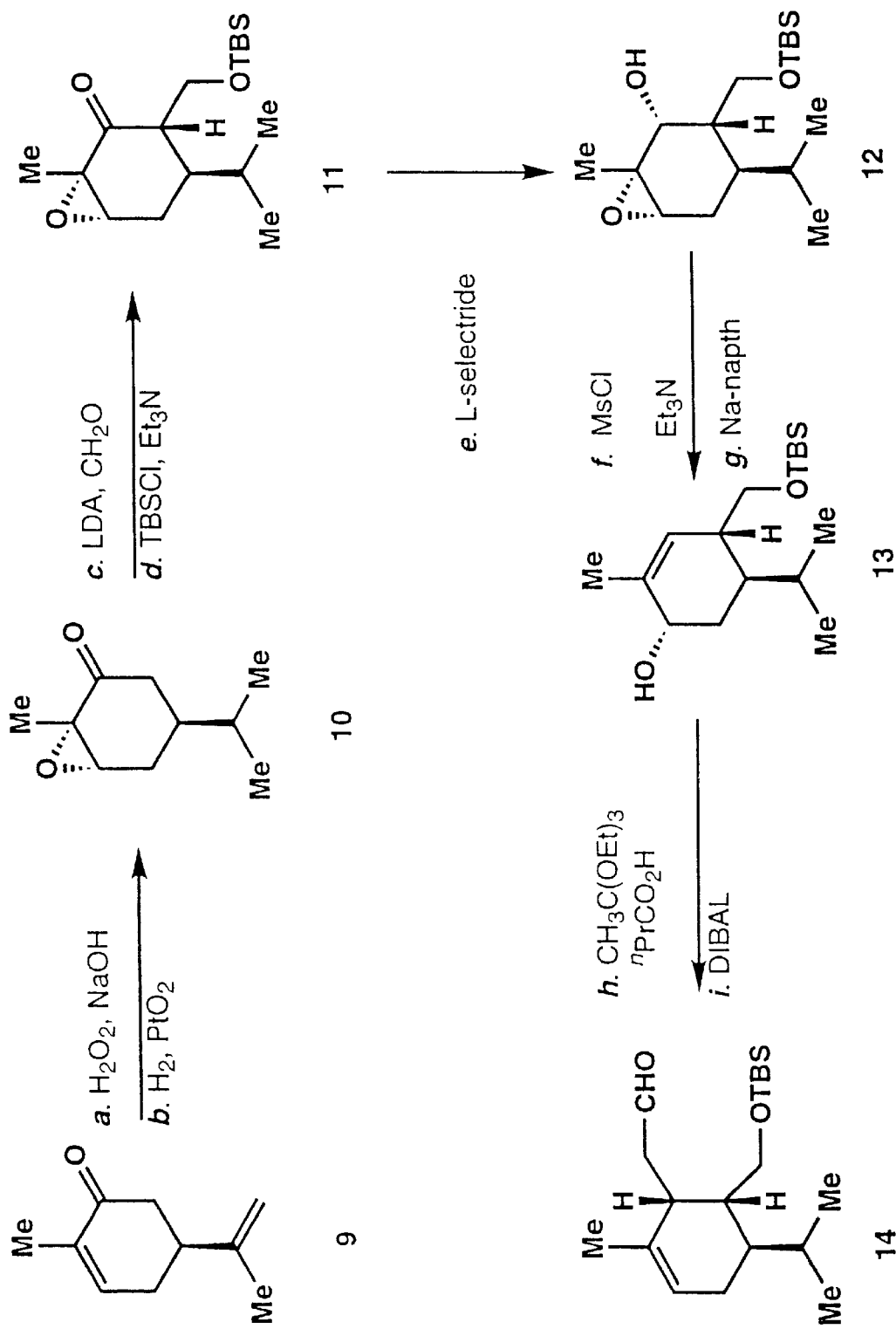
FIG. 3 shows the synthesis of key intermediate (14). Reagents and conditions. a. 1.2 equivalents of $H_2O_2$, 0.3 equivalents of NaOH, MeOH, 2 hours, 0° C.; b. $H_2$, 0.005 equivalents of $PtO_2$, EtOH, 12 hours, 25° C., 87% for two steps; c. 1.4 equivalents of LDA, 5.0 equivalents of $CH_2O$, THF, −78 to 0° C., 2 hours; d. 1.2 equivalents of TBSCl, 4.0 equivalents of $Et_3N$, $CH_2Cl_2$, 12 hours, 53% for two steps; e. 1.2 equivalents of L-selectride, THF, −78° C., 2 hours, 93%; f. 1.2 equivalents of MsCl , 2.5 equivalents of $Et_3N$, $CH_2Cl_2$, 0° C., 0.5 hours; g. 5.0 equivalents of Na-naphthalenide, THF, 0° C., 0.5 hours, 85% for two steps; h. 40 equivalents of $CH_3C(OEt)_3$, 0.1 equivalents of $nPrCO_2H$, 170° C., 72 hours, 74%; i. 1.2 equivalents of DIBAL, $CH_2Cl_2$, −78° C., 0.5 hours, 97%. LDA=lithium diisopropylamide, TBS=t-butyldimethylsilyl, MsCl= methanesulfonyl chloride, DIBAL=diisobutylaluminum hydride.

The synthetic plan called for the initial construction of cyclization precursors of general formula (III, FIG. 2). Consideration of protecting groups and possible routes defined structure 27 (FIG. 4) as a subtarget and compound 14 (FIG. 3) as a key intermediate required for its construction. The appeal of (+)-carvone (9) as a starting material for this synthesis was considerably enhanced by the work of Trost et al. *J. Am. Chem. Soc.* 1991, 113, 670–672 who described its conversion to compound 13 (FIG. 3). Thus, following a modification of the communicated protocols 13 was prepared as shown in FIG. 3. Epoxidation of (+)-carvone under basic hydrogen peroxide conditions followed by hydrogenation of this exocyclic double bond gave 10 in 87% overall yield. Treatment of 10 with LDA (for abbreviations see description of figures) followed by quenching with formaldehyde and silylation of the resulting alcohol furnished silylether 11 in 53% overall yield. Stereoselective L-Selectride® reduction of the ketone functionality in 11 led to 12 (93%). Subsequent mesylation followed by reduction with sodium naphthalenide provided allylic alcohol 13 (85% overall). Finally, exposure of 13 to CH3C(OEt)3 and n-$PrCO_2H$ furnished, via Claisen rearrangement, the expected ethyl ester, which was cleanly reduced with DIBAL to produce aldehyde 14 (72% yield, two steps).

Figure 4:
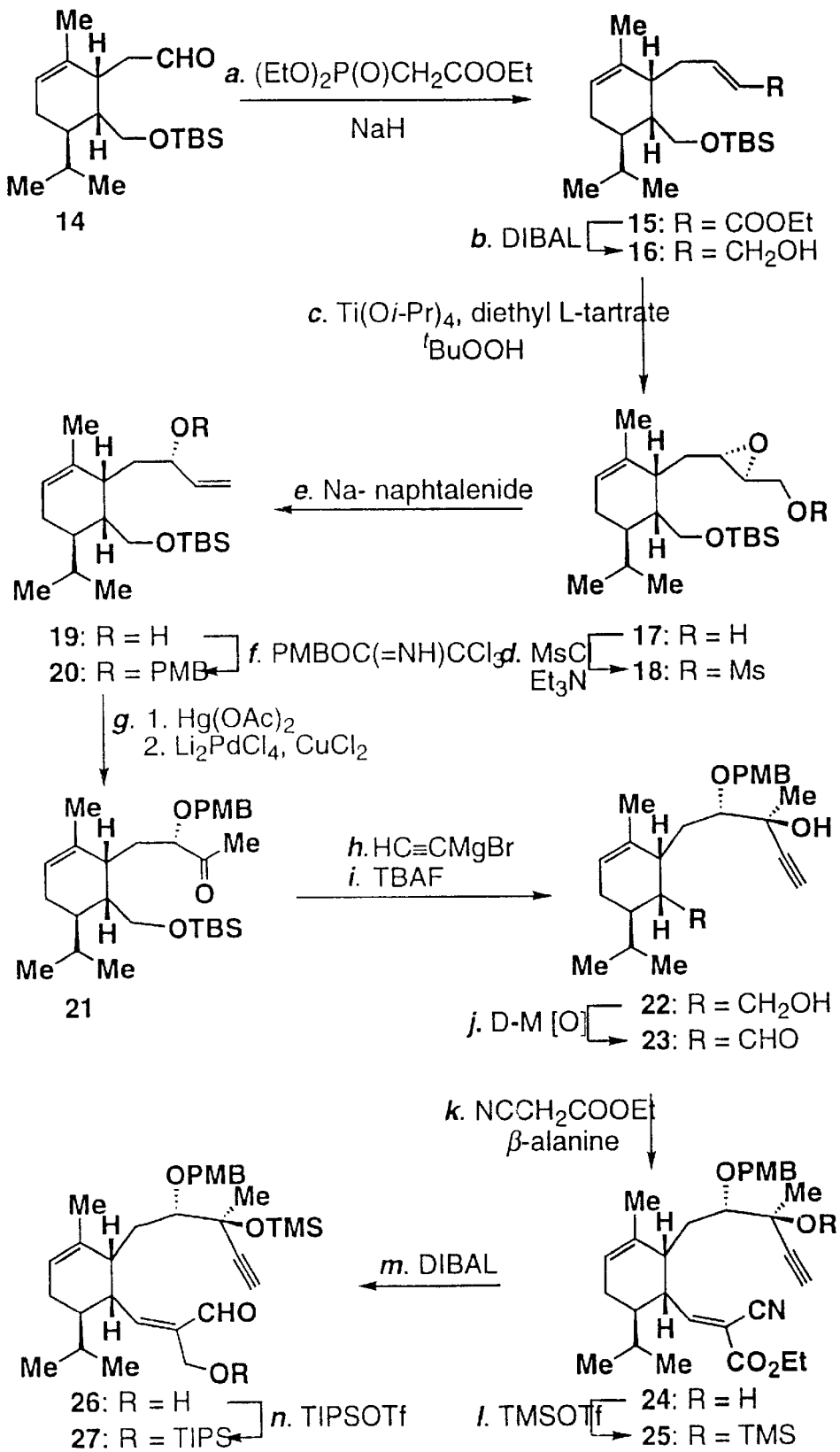
FIG. 4 shows the first generation synthesis of acetylene-aldehyde compound 27. Reagents and conditions. a. 1.5 equivalents of $(EtO)_2P(O)CH_2CO_2Et$, 2.0 equivalents of NaH, THF, 0° C. for 1 hour, then 25° C. for 4 hours, 100%; b. 4.0 equivalents of DIBAL, $CH_2Cl_2$, −78° C., 2 hours, 91%; c. 0.2 equivalents of $Ti(OiPr)_4$, 0.24 equivalents of diethyl L-tartrate, 2.0 equivalents of tBuOOH, 4 Å MS, $CH_2Cl_2$, −20° C., 8 hours, 91%; d. 5.0 equivalents of MsCl, 6.0 equivalents of $Et_3N$, $CH_2Cl_2$, −20° C., 1 hour; e. 5.0 equivalents of sodium naphthalenide, THF, 0° C., 10 min, 90% for two steps; f. 5.0 equivalents of PMBOC(=NH) $CCl_3$, 1.0 equivalent of PPTS, $CH_2Cl_2$, 25° C., 48 hours, 89% based on ca. 50% conversion; g. 1.1 equivalents of $Hg(OAc)_2$, MeOH, 25° C., 12 hours; then 1.0 equivalent of $Li_2PdCl_4$, 3.0 equivalents of $CuCl_2$, MeOH, 55° C., 3 hours, 65%; h. 15 equivalents of HCCMgBr(0.5 M in THF), CH2Cl2:THF(3:1), −78 to 25° C., 12 hours; i. 4.0 equivalents of TBAF, THF, 25° C., 1 hour, 72% for two steps, ds ratio ca. 7:1; j. 1.5 equivalents of Dess-Martin periodinane, 20 equivalents of pyridine, 20 equivalents of $NaHCO_3$, CH2Cl2, 0 to 25° C., 4 hours; k. 30 equivalents of NCCH2COOEt, 4.0 equivalents of β-alanine, 95% EtOH, 25° C., 72 hours; l. 5.0 equivalents of TMSOTf, 10 equivalents of $iPr_2NEt$, $CH_2Cl_2$, −78° C., 10 min, 71% for three steps; m. 10 equivalents of DIBAL, $CH_2Cl_2$, −78° C. for 7 hours then −40° C. for 1 hour, 80%; n. 10 equivalents of TIPSOTf, 20 equivalents of $iPr_2NEt$, $CH_2Cl_2$, −78° C., 1 hour, 91%. TBS=tbutyldimethylsilyl; DIBAL= diisobutylaluminum hydride; PMB=p-methoxybenzyl; PPTS=pyridinium p-toluenesulfonate; TMS=trimethylsilyl; TIPS=triisopropylsilyl; Ms=methanosulfonyl; TBAF=tetra-n-butylammonium fluoride; D-M [O]=Dess-Martin oxidation; Tf=trifluoromethanesulfonate; MS=molecular sieves; THF=tetrahydrofuran.

The stereoselective conversion of 14 to 27 is shown in FIG. 4. Thus, olefination of aldehyde 14 with triethylphosphonoacetate proceeded quantitatively in the presence of NaH to afford ethyl ester 15. DIBAL reduction of 15 gave allylic alcohol 16 in 91% yield and subsequent Sharpless asymmetric epoxidation (diethyl L-tartrate) furnished epoxide 17 (91% yield). The transformation of epoxide 17 to allylic alcohol 19 was accomplished via mesylate 18 in 90% overall yield. Protection of 19 as a PMB-ether [PMBOC(=NH)CCl$_3$, PPTS, 89% yield based on ca. 50% conversion] followed by sequential treatment with Hg(OAc)$_2$ and Li$_2$PdCl$_4$—CuCl$_2$I$_8$ furnished methyl ketone 21 (65% yield) Chelation-controlled addition of HCCMgBr (excess) to ketone 21, followed by desilylation with TBAF gave acetylenic diol 22 as the major diastereoisomer (72% yield, ca. 7:1 de). Attempted oxidation of alcohol 22 to aldehyde 23 with excess Dess-Martin reagent resulted in the formation of lactone A (FIG. 3), m.p.5120-121 C. (ether-hexanes) in 60% yield. The serendipitous preparation of this crystalline compound allowed the assignment of relative stereochemistry within 22 and subsequent intermediates (by x-ray crystallographic analysis) (see ORTEP drawing, FIG. 5).

Controlled oxidation of 22 with 1.5 equivalents of Dess-Martin reagent in the presence of pyridine and NaHCO$_3$ led to the desired aldehyde 23 in good yield. Aldehyde 23 was subjected to Knoevenagel condensation conditions with ethyl cyanoacetate in the presence of -alanine leading, after silylation with TMSOTf and i-Pr$_2$NEt, to the (E)-,-unsaturated-cyanoester 25 via 24 (in 71% overall yield). The geometry of the cyanoester-bearing double bond was later confirmed by successful ring closure to intermediate 37 (vide infra, FIG. 7). A highly regioselective reduction of the cyanoester moiety of 25 was effected with DIBAL to afford hydroxy-aldehyde 26 in 80% yield. Finally, protection of the primary alcohol in 26 with TIPSOTf and i-Pr2NEt gave the targeted protected acetylenic aldehyde precursor 27 in 91% yield.

A second, less stereoselective but more direct, route to a cyclization precursor acetylenic aldehyde 36 was also undertaken, as shown in FIG. 6. Thus, aldehyde 14 (Nicolaou et al. *J. Am. Chem. Soc.* 1997, 119, 11353–11354) was reacted with 1-ethoxyvinyllithium followed by exposure to acid to afford a 1.25:1 mixture of C8-epimeric hydroxyketones 28 in 82% overall yield. This mixture was then reacted with excess HCMgBr in a stereoselective manner, affording a chromatographically separable mixture of the two epimeric acetylenic diols, 29 (43% yield) along with it C7,C8-diastereoisomer (33% yield). Removal of the silyl protecting group from 29 was accomplished by exposure to TBAF furnishing, after flash column chromatography, the pure triol 30 (92%). The identity of 30 was proven by comparison to an authentic sample obtained from 22 (whose structure was unambiguously proven by x-ray analysis as discussed above).

The conversion of 30 to aldehyde 33 required a sequence defined by intermediates 31 (persilylation with TESOTf-Et3N, 100% yield) and 32 (selective desilylation with PPTS in MeOH, 98% yield), and oxidation of the latter compound with TPAP-NMO in CH$_2$Cl$_2$ (98% yield). The Knoevenagel condensation of 33 with ethyl cyanoacetate proceeded smoothly as described above for 33 furnishing (E)-,-unsaturated-cyanoester 34 (95% yield) whose DIBAL reduction gave, regioselectively, hydroxyaldehyde 35 (90% yield). Silylation of 35 with TIPSOTf and i-Pr$_2$NEt, finally led to the desired acetylenic aldehyde precursor 36 in 93% yield.

Cyclization and Formation of Tricyclic Framework

The first approach to sarcodictyins involved key intermediate 27 and had as its initial subtarget tricyclic compound 42 (FIG. 7). The ring closure of 27 was effected by the action of LiHMDS in THF at 25 C yielding the expected 10-membered ring alcohol (mixture of two isomers) whose oxidation with Dess-Martin reagent led to eneynone 37 in 85% overall yield. The TMS group was then removed from 37 by exposure to PPTS in MeOH furnishing alcohol 38 in 94% yield. Hydrogenation of eneynone 38 in the presence of Lindlar's catalyst resulted in the formation of tricyclic system 40 (75% yield), presumably via spontaneous collapse of the initially formed dienone 39. Quantitative conversion of hemiketal 40 to its methoxy derivative 41 was effected by exposure to PPTS in MeOH. Removal of the PMB group from 41 for the purposes of side-chain attachment was carried out by Na in liquid NH$_3$(THF-EtOH) and furnished the targeted tricyclic system 42 along with its C5–C6 saturated counterpart, compound 43 (95% combined yield, ca. 2:1 ratio).

A slightly modified sequence is presented in FIG. 9. Specifically, removal of the PMP-ether from 37 was accomplished after its treatment with DDQ in aqueous CH$_2$Cl$_2$ resulting in the formation of ynone hydroxy 44 in 80% yield. Liberation of the propargylic hydroxy moiety was performed by the action of PPTS in MeOH furnishing diol 45 in 80% yield. The employment of [Rh(nbd)(dppb)]BF4 as the hydrogenation catalyst proved to be beneficial since tricyclic alcohol 42 was isolated in 80% yield after the formation of the methyl ketal functionality (PPTS, MeOH).

The significant extent of reduction of the C5–C6 double bond in our first approach, which was observed in the hydrogenation of 38 to 40, prompted the second general approach to the sarcodictyins which involved intermediate 36 (FIG. 10) carrying different protecting groups for easier removal. Its conversion to the key dihydroxy ynone 45 is detailed in FIG. 10. Thus, treatment of 36 with LiHMDS in THF at −20 C. resulted, as before, in the formation of the 10-membered ring alcohol 48 (mixture of diastereoisomers) which was immediately oxidized with Dess-Martin reagent to eneynone 49 (89% yield for two steps). Selective removal of both TES groups was achieved by exposure to Et3N.3HF (78% yield) furnishing diol 45 and setting the stage for selective hydrogenation and internal cyclization.

To this end, the experiments summarized in FIG. 8 were carried out using acetylenic substrates 37 (FIG. 7), 38 (FIG. 7) and 45 (FIG. 10) and a variety of hydrogenation conditions. The exploration led quickly to the adoption of the rhodium complex [Rh(nbd)(dppb)]BF$_4$ in acetone solution as the catalyst of choice (ca. >10:1 ratio in favor of the desired product 42 which was obtained in 80% yield). With the solution of the reduction problem at hand, the only remaining task was the construction of the side-chains before the final targets were reached.

Construction of the Side Chain and Completion of the Synthesis

The attachment of the C-8 ester functionality, a mixed anhydride protocol was adopted (Nicolaou et al. *Angew. Chem. Int. Ed. Engl.* 1997, 36, 2520–2524). To this end, ethyl (E)-N(6)-methylurocanate (50, FIG. 11; Viguerie et al. *Heterocycles* 1994, 37, 1561–1576) was sequentially converted to its sodium salt 51 by the action of NaOH (THF-H2O, 100%) and thence to tert-butyl mixed anhydride 52 by treatment with t-BuCOCl in THF (75% yield). Reaction of 42 with 52 in the presence of Et$_3$N and 4-DMAP resulted in the formation of ester 53 in 83% yield.

For the purposes of completing the side-chain at C-3, a carboxylic acid group was formed at this position as follows: (i) desilylation with TBAF to afford alcohol 54 in 100% yield; (ii) Dess-Martin oxidation to aldehyde 55; and (iii) further oxidation of 55 with NaClO$_2$ to furnish 56. Exposure of carboxylic acid to CH$_2$N$_2$ or CH$_3$CHN$_2$ furnished methoxy-sarcodictyin A (57, 88% overall yield from 54) or methoxy sarcodictyin B (58, 86% overall yield from 54). Finally, sarcodictyins A (7) and B (8) were generated from their respective methoxy derivatives by treatment with CSA in CH2Cl2—H2O (80% yield for 7 and 86% for 8).

In order to evaluate the importance of the C5–C6 double bond of sarcodictyins for biological activity, C5–C6 dihydrosarcodictyin A (61) was targeted for chemical synthesis. FIG. 12 summarizes an efficient route to 61 from intermediate 45. Thus, hydrogenation of 45 in the presence of 5% Pd/BaSO4 in EtOAc, followed by exposure to PPTS in MeOH resulted in the formation of tricyclic compound 43 (64% overall yield) in which the C5–C6 bond was completely reduced. The construction of the two side-chains proceeded smoothly as described already for compound 42 (FIG. 9) and via compounds 59 and 60 furnishing the desired dihydrosarcodictyin A (61) in excellent overall yield (see FIG. 12).

Sarcodictyins A (7) and B (8) and C5–C6 dihydrosarcodictyin A (61)

Two approaches utilize an intramolecular acetylide-aldehyde addition to construct a 10-membered ring, those elaboration and selective hydrogenation results in the formation of a transient hydroxy-dienone which spontaneously collapses to the tricyclic ring system of sarcodictyins A and B. Appropriate appendage attachments at C-8 and C-15 then leads to completion of the syntheses. The designed strategy allows for a solid phase synthesis, specific analog construction and combinatorial library generation. The solid phase synthesis of sarcodictyins A and B and analogs thereof is described in the following Example II. These studies facilitate the investigation of the chemical biology of sarcodictyins and related compounds.

Solid and Solution Phase Synthesis and Biological Evaluation of Combinatorial Sarcodictyin Libraries In this example, we disclose (a) the first total synthesis of sarcodictyins A (7) and B (8) by a combination of solution and solid phase methods through the attachment of the common precursors 1880 or 200 on solid support, thus generating conjugates 230 and 240, followed by standard chemical manipulations; (b) the construction of a combinatorial library of sarcodictyins by solution and solid phase chemistry modifying the C-8 ester, C-15 ester and C-4 ketal functionalities, and, therefore, producing analogs of the general structures 330, 370 and 400; (c) the tubulin polymerization properties of members of the library; and (d) the cytotoxic actions of a selected number of these compounds against a number of tumor cells including Taxol-resistant lines. Several of the synthesized analogs were identified to be of equal or superior biological activities (e.g. 600, 610, 630, 660–700, 730, 760, 850, 920) as compared to the natural products, setting the stage for further developments in the field of cancer chemotherapy.

Molecular Diversity Design. Solid Phase Strategy

Inspection of the structure of sarcodictyins A (7) and B (8) reveals the three branches of possible molecular diversification; those emanating from skeletal carbons C-3, C-4 and C-8 (see structure I, FIG. 2 for numbering). Furthermore, the ready availability of a suitable common intermediate for attachment to a solid support and the potential reactivity of the functional groups at C-3, C-4 and C-8 presented an attractive opportunity for the design and construction of a general sarcodictyin library depicted under structure I (FIG. 13). Thus, compounds I could be obtained by transketalization with a variety of alcohols with simultaneous cleavage from the resin II, whereas the latter structure (II) could be tailored from III by various functional group (FG) manipulations at the indicated positions. Structures III, in turn, could be obtained from IV by ester or carbamate bond formation. Finally, disconnection of the conjugates IV unravel possible precursors, sarcodictyin scaffold V, an appropriate linker VI, and resin VII (FIG. 13).

Construction of Resins and Substrates for Attachment

In preparation for a solid phase synthesis of sarcodictyins A (7) and B (8) and libraries thereof, the functionalized resins 10, 12 and 14 were designed and constructed as shown in FIG. 14 (Nicolaou et al. *Nature* (London) 1997, 387, 268–272; Nicolaou et al. *J. Am. Chem. Soc.* 1998, 120, 5132–5133; Nicolaou et al. *Angew. Chem. Int. Ed. Engl.* 1997, 36, 2097–2103). Thus, hydroxymethyl polystyrene resin (90) was reacted with excess glutaric anhydride in the presence of Et3N, followed by capping with pivaloyl chloride under the same conditions, to afford resin 100 in >90% overall yield. On the other hand, reaction of Merrifield resin (110) with excess of the monosodium alkoxide of 1,4-butanediol resulted in the formation of resin 120 in 99% yield. Iodination of the latter (12) with I2-Ph3P-imidazole then furnished iodide 130 (>95% yield) which was converted to its phosphonium salt by treatment with Ph$_3$P at 100° C. (95% yield) and hence to phosphorane 140 (>90% yield) by the action of LiHMDS (for abbreviations description of figures). These resins were then ready for coupling with suitable sarcodictyin scaffolds such as 160, 170, 180 and 200 (FIG. 15). The latter compounds were prepared from the previously synthesized intermediate 47 as shown in FIG. 15. Thus, coupling of 47 with ethylene glycol or 1,4-butane diol in the presence of PPTS resulted in the formation of compounds 160 (91%) and 170 (94%) respectively. On the other hand, acetylation of 47 furnished 180 (96%) whose reaction with 1,6-hexanediol in the presence of PPTS led to 190 (92%). Oxidation of 190 with Dess-Martin reagent gave the desired aldehyde 200 in 96% yield.

Loading of Sarcodictyin Scaffolds onto the Solid Support

The reaction of sarcodictyin derivatives 160 and 170 with excess functionalized resin 100 in the presence of Et$_3$N and 4-DMAP led, unexpectedly, to conjugates 210 and 220 respectively in >95% yield. The surprising fact that derivatives 160 and 170 attached themselves to the resin via their secondary, rather than primary, hydroxyl groups was evident from the resistance of 210 and 220 to undergo cleavage under acidic conditions and the ease by which these scaffolds could be recovered under basic conditions. This led us to the investigate the resins 120 and 140. Thus, conjugation of 180 to resin 120 was accomplished in the presence of PPTS to afford 230, but only in 50% yield despite several attempts to drive the reaction to completion with dehydrating agents. In contrast, coupling of aldehyde 200 with resin 140, followed by capping with acetaldehyde, proceeded smoothly to afford conjugate 240 in >95% yield, making this resin a more attractrive starting point for further chemical studies.

Solid Phase Synthesis of Sarcodictyins A and B

With resins 230 and 240 in hand, we proceeded to investigate their use in the synthesis of a sarcodictyin library. As a prelude to a library construction, and in order to develop the chemistry required for the operation, we first targeted the naturally occurring sarcodictyins A (7) and B (8). As demonstrated in FIG. 17, both resins performed equally well. Thus, NaOMe induced deacetylation of 230 or 240 led smoothly to 250 (>95%) which coupled with mixed anhydride 260 in the presence of Et$_3$N and 4-DMAP to afford conjugate 270 in ca. 90% yield. Desilylation of 270 (>95%), followed by Dess-Martin oxidation (>95%) led efficiently to aldehyde 280. Further oxidation of 280 with NaClO$_2$ (>95%) and esterification of the resulting carboxylic acid with MeOH or EtOH in the presence of DCC furnished, in ca. 90% yield, sarcodictyin A and B conjugates 290 and 300 respectively. Finally, generation of the natural substances (7 and 8) from the corresponding resins was achieved by exposure to CSA in $CH_2Cl_2:H_2O$ (2:1). The overall yield of sarcodictyin A (7) was ca. 51% from 240 or 44% from 230 and of sarcodictyin B (8) was 48% from 240 or 42% from 230. The spectroscopic properties of 7 and 8 were identical to those exhibited by authentic samples previously obtained in these laboratories by a solution total synthesis.

Construction of a Sarcodictyin Combinatorial Library

The sarcodictyin library shown in FIG. 20 was constructed by a combination of solid phase (FIG. 18) and solution (FIG. 19) methods. For the solid phase chemistry, resin 240 was used because of its excellent profile in terms of formation, efficiency and reactivity performance. Both parallel and combinatorial techniques were applied, the latter utilizing Radiofrequency Encoded Combinatorial (REC) chemistry (Nicolaou et al. *Angew. Chem. Int. Ed. Engl.* 1995, 34, 2289–2291; Moran et al. *J. Am. Chem. Soc.* 1995, 117, 10787–10788; Nicolaou et al. *Angew. Chem. Int. Ed. Engl.* 1997, 36, 2097–2103).

Thus, individual flasks with resin 250 or IRORI Microkans™21 containing resin 250 were utilized to carry out the chemistry summarized in FIG. 18. Thus, 250 (derived by deacetylation of 240) was reacted with LG-R1 [acid anhydride, acid chloride, carboxylic acid, or isocyanate] under the appropriate coupling conditions to afford a series of esters and cabamates (90–95%) which were deprotected with TBAF, leading to hydroxy esters 310 (>95%). A portion of the reactant (resin or Microkans™, 310) was treated with LG-R2 [acid anhydride, acid chloride or isocyanate] under appropriate coupling conditions to afford, after PPTS-induced cleavage in the presence of HO—R3 (60–90%) a series of sarcodictyins 330 via conjugates 320.

A second portion of the reactant 310 was subjected to Dess-Martin oxidation to afford aldehyde resin 340 in >95% yield. Further oxidation of 340 with $NaClO_2$ led to carboxylic acid resin 350 (>95%) which was subjected to coupling reactions with either alcohols [HO—$R_4$] under Mitsunobu conditions or amines [$H_2N$—R4] under DCC/4-DMAP conditions. The resulting esters or amides (360) were then exposed to acid (CSA) cleavage conditions in HO—$R_3$, affording sublibrary 370 (60–90%).

A third portion of the reactant 31 was converted to azide 380 in >95% yield by the action of $(PhO)_2PON_3$, DEAD and $Ph_3P$. Reduction of the azido group in 380 with $Ph_3P$—$H_2O$ gave the corresponding amine (95%) which was coupled with LG-R5 [anhydride or acid chloride] to afford the amide derivatives 390. Compounds 400 were then released from the resins 390 by exposure to PPTS in $HO_3$ (60–90%). Each library member was obtained in ca. 1–5 mg scale and was purified by silica gel chromatography (flash column or thin layer) or HPLC. The rather wide range in yield for the cleavage was attributed to kinetic reasons and/or instability of the individual products to prolonged exposure to acidic conditions.

Due to the low yields obtained for the DCC coupled products on solid phase, a number of sarcodictyin analogs were prepared by conventional solution methods. Specifically, sarcodictyins 420–540 were synthesized as outlined in FIG. 19. Thus, a number of ester side chains were introduced at C-8 and the appendage at C-4 was modified to include $CH_2OH$, $CH_2OAc$ and $CH_2F$. Thus, DCC/4-DMAP assisted coupling of 410 with carboxylic acids Ar-I, Ar-II and Ar-III (derived from the corresponding known pyridine, thiazole (Nicolaou et al. *J. Am. Chem. Soc.* 1997, 119, 7960–7973; Nicolaou et al. *J. Am. Chem. Soc.* 1997, 119, 7974–7991) and oxazole (Kende et al. *Tetrahedron Lett.* 1995, 36, 4741–4744) aldehydes by a Wittig olefination-saponification sequence in excelent yields) gave, after TBAF removal of the silicon protecting group, esters 420 (73%), 430 (61%) and 440 (79%) respectively. Dess-Martin oxidation of these hydroxy esters led to aldehydes 450 (44%), 460 (40%) and 470 (84%) respectively.

Further oxidation of 450, 460 and 470 with $NaClO_2$ and treatment of the resulting carboxylic acids with $CH_2N_2$ or $CH_3CH_2N_2$ led to the formation of sarcodictyins 480 (43%), 490 (71%) and 500 (87%) respectively. The fluorosarcodictyin 52 (K. C. Nicolaou et al. *Angew. Chem. Int. Ed.* 1998, 37, 1418–1421) was generated from the previously synthesized compound 51 (K. C. Nicolaou et al. *Angew. Chem. Int. Ed.* 1998, 37, 1418–142) by the action of DAST (99%), whereas acetates 53 (K. C. Nicolaou et al. *Angew. Chem. Int. Ed.* 1998, 37, 1418–1421) and 54 were prepared from 51 by sequential treatment with $Ac_2O/Et_3N$/4-DMAP and CSA in $CH_2Cl_2:H_2O$ as indicated in FIG. 19.

Biological Evaluation of Sarcodictyins

The synthesized sarcodictyin library (shown in FIG. 20) was screened for induction of tubulin polymerization using the filtration calorimetric assay and 100 m compound at 37° C. (results are listed in FIG. 20; Bollag et al. *Cancer Res.* 1995, 55, 2325–2333). These investigations were then followed by cytotoxicity studies with ovarian cancer cells (1A9) including two taxol-resistant lines (1A9PTX10 and 1A9PTX22; Giannakakou et al. *J. Biol. Chem.* 1995, 272, 17118–17125). Experiments showing IC50 values less than 2000nM in any of the tested cell lines are tabulated in FIG. 21. The data reveal a number of important structure activity relationships (SARs). Thus, compounds 600, 730–750 and 850 exhibited superior tubulin polymerization properties to those of either sarcodictyins A (7) or B (8). In the cytotoxicity studies compounds 600, 610, 630, 660–700, 730, 760, 850 and 920 exhbitied potencies comparable or higher that those of the natural substances (7 and 8). Particularly striking were the cytotoxicities of compounds 600, 610, 670, 680, 730, 760, 850 and 920 against the taxolresistant tumor cell lines. Interestingly, the tubulin polymerization potencies of some of these compounds were not always in line with their cytotoxicity effects (e.g. compounds 610 and 700). These observations suggest an additional mechanism of action for these compounds such as DNA alkylation.

The importance of the C-8 ester side chain became apparent by a number of substitutions. Thus, replacing the natural urocanic acid side chain with acetate (compound 1070, FIG. 20) or phenyl carbamate (compound 1010, FIG. 20) resulted in complete loss of activity. Likewise, substitution of the heterocycle with a phenyl group while maintaining the α,β unsaturated portion of the ester side chain leads to only negligible biological activity (compound 990, FIG. 20). Even the more subtle substitution of the imidazole-derived natural substituent for a pyridine (compound 480, FIGS. 20 and 21), thiazole (compound 490, FIGS. 20 and 21) or an oxazole (compound 500, FIGS. 20 and 21) moieties led to considerable loss of activity. thereby suggesting a role for both nitrogen atoms of the natural products in their mechanism of action. In contrast, modifications at the C-4 ketal center appear more tolerable for biological activity. Thus, replacement of the OH group of the natural products with an OMe moiety resulted in enhanced biological activity against the taxol-resistant cell lines (compounds 600 and 610, FIGS. 20 and 21), whereas substitution with OnPr or OCH2CF3 resulted in an overall decrease of cytotoxicity (compounds 740 and 840, FIGS. 20 and 21).

The C-15 reduced compound and derivatives thereof (e.g. compounds 510–530 and 550–590, FIGS. 20 and 21) failed to exhibit strong tubulin polymerization or cytotoxicity properties, which is rather intriguing, given the potent biological actions of eleutherobin (4) whose C-15 position is reduced and glycosylated. Interestingly, the C-15 dimethyl acetal (compound 730, FIGS. 20 and 21) displayed biological activities comparable to those of the natural products (7 and 8, FIGS. 20 and 21), thus, demonstrating that ester functionality is not a requirement for activity. Modification of the alcohol component of the C-2 ester group resulted in significant modulation of the biological actions of these compounds as compared to the natural products. Thus, substitution of the methyl (compound 600, FIGS. 20 and 21) with an ethyl (compound 610, FIGS. 20 and 21), n-propyl (compound 680, FIGS. 20 and 21) or allyl group (compound 700, FIGS. 20 and 21) resulted in enhancement of the biological activity. A reversal of the trend was noted with bulkier substituents, such as n-butyl (compound 630, FIGS. 20 and 21) or isopentyl (compound 710, FIGS. 20 and 21). Interestingly, however, the bulky moieties of anthracenyl (compound 920, FIGS. 20 and 21), benzyloxyethyl (compound 690, FIGS. 20 and 21) and 4-butylphenyl (compound 660, FIGS. 20 and 21) exhibited cytotoxicity comparable to, or better than, the natural products (even though their tubulin polymerization potencies were modest). FIG. 22 summarizes the SARs so far obtained within the sarcodictyin family of compounds.

In this example, we illustrate the development of solid phase chemistry for the chemical synthesis of the naturally occurring sarcodictyins A (7) and B (8) and its application to the construction of a sarcodictyin combinatorial library. This library was complemented with compounds synthesized by solution methods and was subjected to biological evaluation with regards to tubulin polymerization and cytotoxicity. The results were useful both in terms of new synthetic methodology development and structure activity relationships in this new structural class of compounds. Furthermore, the chemistry described herein demonstrates the use of REC chemistry (Nicolaou et al. *Angew. Chem. Int. Ed. Engl.* 1995, 34, 2289–2291; Moran et al. *J. Am. Chem. Soc.* 1995, 117, 10787–10788; Nicolaou et al. *Angew. Chem. Int. Ed. Engl.* 1997, 36, 2097–2103) in chemical biology studies and sets the stage for further developments in the field of cancer chemotherapy.

EXAMPLE III

Synthesis of Eleutherobin and Eleuthosides A and B

This example describes the total synthesis of the cytotoxic marine natural products eleutherobin (4) and eleuthosides A (5) and B (6) is described. The strategy involves glycosidation of the (+)-carvone-derived intermediate 35 with the arabinose-derived trichloroacetimidate 900 (FIG. 24) followed by base-induced ring closure and elaboration to afford the dihydroxy eneynone 1900. Selective hydrogenation of 1900 led to the generation and intramolecular collapse of dienone 2000 furnishing 2100 and thence 22 with the required structural framework of the target molecules. Finally, esterification with mixed anhydride 2400 followed by deprotection gave eleutherobin (4) which served as a precursor to eleuthosides A (5) and B (6). The α-glycoside anomer of eleutherobin, compound 2700 (FIG. 26), was also synthesized by application of the developed chemistry, demonstrating the flexibility of the sequence in generating designed analogs for biological screening.

Retrosynthetic Analysis and Strategy

Figure 1:
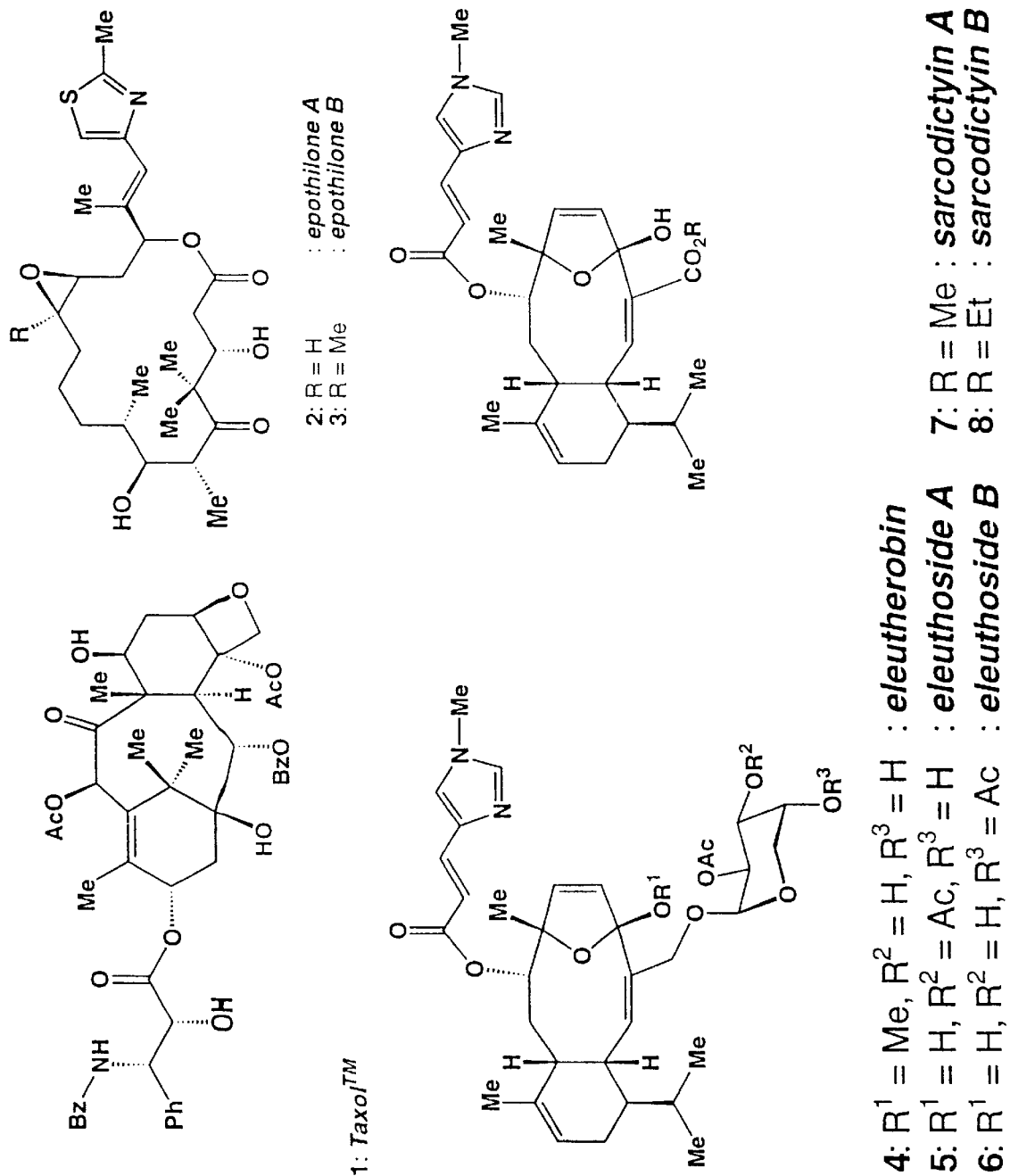
FIG. 1 illustrates molecular structures of Taxol™ (1), epothilones A (2) and B (3), eleutherobin (4), eleuthosides A (5) and B (6) and sarcodictyins A (7) and B (8) (Ac=acetyl, Bz=benzoyl).

With the exception of the D-arabinopyranose moiety, the structural features of eleutherobin (4) and the eleuthosides A (5) and B (6) are similar to those of the sarcodictyins (7,8). Thus, the strategy for their total synthesis was devised from a similar retrosynthetic analysis with appropriate provisions for the introduction of the carbohydrate unit. FIG. 1 outlines the retrosynthetic analysis for eleutherobin (4) and the eleuthosides (5,6). Thus removal of the (E)-N(6)-methylurocanic acid residue from the target structure (I) and dismantling of the oxygen bridge of the central bicyclic core leads to the 10-membered ring dihydroxy dienone II, whose origin can be traced to the open-chain acetylenic aldehyde III. As shown in FIG. 24, further carbon-carbon bond disconnections and retro-glycosidation lead to hydroxy acetylene 35, whose relationship to (+)-carvone was amply evident. It was comforting to know that, although the (+)-enantiomer of carvone was chosen as the initial starting material, the (−)-enantiomer was also available in case the absolute stereochemistry of the natural substances required it. The trichloroacetimidate 900 required for the projected total synthesis was traced to D-arabinose tetraacetate 1000. The execution of the total synthesis of eleutherobin (4) and eleuthosides A (5) and B (6) was carried out as described below.

Total Synthesis of Eleutherobin (4)

The construction of the (+)-carvone-derived hydroxyaldehyde fragment 35 (FIG. 24) has been described in the preceding example We will, therefore, begin here with the synthesis of the requisite fragment, trichloroacetimidate 900 (FIG. 23). Thus, arabinosetetraacetate (1000) was efficiently converted to thioglycoside 1100 by a sequence recently reported from these laboratories (Nicolaou et al. *Angew. Chem. Int. Ed. Engl.* 1997, 36, 2520–2524). The hydroxyl group of 1100 was then protected as a PMB ether by the action of PMB—Cl in the presence of NaH (93% yield) and the acetonide group of the resulting compound 1200 was removed by treatment with TsOH in ethylene glycol:methanol (1:10), furnishing diol 1300 in 84% yield. Both hydroxyl groups in 1300 were then silylated (TBSOTf-Et$_3$N, 97% yield of 1400) and the anomeric position was freed by the action of NBS-pyr. in aqueous acetone, affording lactol 1500 (80% yield, ca. 2:1 mixture of anomers). Finally, treatment of 1500 with NaH, followed by addition of C13CCN gave the desired trichloroacetimidate 900 in 93% yield as the major isomer (greater than 95% purity). Purification of this sensitive intermediate could be achieved by flash chromatography with a short column (silica, 10% ether in hexane containing 1% Et3N).

The next task was to define suitable conditions for the stereospecific glycosidation of hydroxyaldehyde 35 with the arabinose-derived carbohydrate donor 900. To this end, the study in FIG. 25 was carried out. Indeed, it was possible to reverse the stereoselectivity of the formed glycoside bond by varying the experimental conditions. Thus, while reaction of 35 with 900 in hexane in the presence of TMSOTf as a catalyst at −78° C. gave a ca. 8:1 ratio of glycosides in favor of the α-anomer 2600 (75% combined yield), the use of dioxane:toluene (2:1) as solvent at 0° C. led to a ca. 8:1 ratio of products in favor of the desired β-anomer 2500 (75% yield after flash chromatography purification). Flash chromatography produced pure 2500 ready for the next step.

Reaction of the pure β-anomer 2500 with LiHMDS in THF at −30° C. caused smooth cyclization via acetylide formation and intramolecular attack on the aldehyde group affording an intermediate secondary alcohol (mixture of diastereomers) which was immediately oxidized with Dess- Martin reagent to dienone 1600 (FIG. 24; Chen et al. *Angew. Chem. Int. Ed.* 1998, 37, 789–792).

It was now time to install the acetate group at the C-2 position of the pyranose ring. Selective removal of the PMB group from 1600 with DDQ led to the formation of the corresponding hydroxy compound 1700 (FIG. 24) in 91% yield. Standard acetylation then led to acetate 1800 (95% yield). Both TES groups were then removed from 1800 without damage of the TBS group by the discriminating action of $Et_3N_3HF$ in THF at 25° C. furnishing diol 1900.

The next objective in the synthesis was the generation of the key dienone 2000, the fleeting intermediate expected to readily collapse in favor of its bridged isomer 2100 (FIG. 24). Indeed, upon selective hydrogenation of the acetylene moiety (Lindlar cat., $H_2$, toluene, 25° C.), compound 1900 gave rise to the expected lactol 2100, whose conversion to the methoxy ketal 2200 proved straight forward (MeOH, PPTS, 76% yield from 1900).

The attachment of the (E)-N(6)-methylurocanic acid residue onto the main framework of the target molecule was accomplished by reaction of alcohol 2200 with mixed anhydride 2400 (Yang et al. *Angew. Chem. Int. Ed. Engl.* 1997, 36, 166–168; Nicolaou et al. *Angew. Chem. Int. Ed. Engl.* 1997, 36, 525–526) in the presence of $Et_3N$ and 4-DMAP in $CH_2Cl_2$ at 25° C., leading to esterified product 2300 (97% yield). Finally, exposure of 2300 to TBAF-AcOH in THF resulted in the cleavage of the TBS group and the liberation of eleutherobin (4) in 96% yield. Synthetic eleutherobin (4) exhibited identical physical data to those reported for the natural substance. Furthermore, the sign of its rotation $[\alpha]_D$ −67 (c=0.2, MeOH) was the same as that reported for the natural eleutherobin, establishing the absolute stereochemistry of the latter as that corresponding to (+)-carvone and structure 4.

The α-glycoside analog 2700 of eleutherobin (FIG. 26) was synthesized from the α-anomer 2600 (FIG. 25) by following the same route as for 4 (shown in FIG. 24). The yields for the steps involved in this construction were similar to those for the eleutherobin sequence.

Total Synthesis of Eleuthosides

The eleuthosides A (5) and B (6) were synthesized from eleutherobin (4) as indicated in FIG. 27. Thus exposure of 4 to 1.1 equivalents of $Ac_2O$ in the presence of excess $Et_3N$ and 0.2 equivalents of 4-DMAP in $CH_2Cl_2$ at 0° C. resulted in the formation of triacetate 2800 (12% yield) and diacetates 2900 and 3000 (75% yield as a ca. 1:2 mixture in favor of 2900 by $^1$H-NMR), plus some unreacted starting material (13%). The inseparable mixture of diacetates (2900 and 3000) was exposed to CSA in moist $CH_2Cl_2$, furnishing a mixture of eleuthosides A and B (5+6). This mixture could not be separated by conventional chromatographic methods and was characterized as such, matching, in all respects, the data reported for the natural eleuthosides A (5) and B (6). Exposure of bis-TBS ether 2300 (or 4) with TBAF in THF at 25° C. caused slow migration of the acetate group from the 2-position to the 4-hydroxyl group, leading to the isomeric elueltherobin 3100 (60% yield) as well as deacylation leading to deacetoxyeleutherobin 3200 (8% yield). The structure of 3100 was established by NMR spectroscopic methods (1H 1D- and 2D-COSY) and comparisons with 4 and 2300.

Thus, in summary, example III teaches a strategy similar to that described for the sarcodictyns A and B in examples 1 ad by incorporating the arabinose pyranoside moiety into the molecule prior to ring closure, the total synthesis of the marine natural products eleutherobin (4) and eleuthosides A (5) and B (6) has been accomplished. In addition, the chemical synthesis of the isomeric eleutherobin (2700) in which the glycosidic bond is oriented in the α-position as well as the eleuthoside analogs 2800–3200 is described. The reported chemistry allows access, not only to the rare naturally occurring substances, but also to designed analogs and combinatorial libraries for biological screening purposes. Combined with their appealing mechanism of tubulin polymerization and microtubule stabilization, the described technology makes the eleutherobins and eleuthosides an attractive proposition as a new class of potential anticancer agents for further investigation.

It should be noted that the compounds as described in FIGS. 28–34 are synthesized according to the the same conditions as described for the compounds shown in FIG. 20.

While a preferred form of the invention has been shown in the drawings and described, since variations in the preferred form will be apparent to those skilled in the art, the invention should not be construed as limited to the specific form shown and described, but instead is as set forth in the following claims.

EXPERIMENTAL PROTOCOL

General Techniques. All reactions were carried out under an argon atmosphere with dry, freshly distilled solvents under anhydrous conditions, unless otherwise noted. Tetrahydrofuran (THF), toluene and ethyl ether (ether) were distilled from sodium-benzophenone, and methylene chloride (CH2Cl2), from calcium hydride. Anhydrous solvents were also obtained by passing them through commercially available alumina column. Yields refer to chromatographically and spectroscopically ($^1$H NMR) homogeneous materials, unless otherwise stated. Reagents were purchased at highest commercial quality and used without further purification, unless otherwise stated. Reactions were monitored by thin layer chromatography carried out on 0.25 mm E. Merck silica gel plates (60F-254) using UV light as visualizing agent and 7% ethanolic phosphomolybdic acid or p-anisaldehyde solution and heat as developing agents. E. Merck silica gel (60, particle size 0.040–0.063 mm) was used for flash column chromatography. Preparative thin-layer chromatography (PTLC) separations were carried out on 0.25, 0.50 or 1 mm E. Merck silica gel plates (60F-254). NMR spectra were recorded on Brucker DRX-600, AMX-500 or AMX-400 instruments and calibrated using residual undeuterated solvent as an internal reference. The following abbreviations were used to explain the multiplicities: s=singlet, d=doublet, t=triplet, q=quartet, sept=septet, m=multiplet, br=broad. IR spectra were recorded on a Perkin-Elmer 1600 series FT-IR spectrometer. Optical rotations were recorded on a Perkin-Elmer 241 polarimeter. High resolution mass spectra (HRMS) were recorded on a VG ZAB-ZSE mass spectrometer under fast atom bombardment (FAB) conditions with NBA as the matrix. Melting points (mp) are uncorrected and were recorded on a Thomas Hoover Unimelt capillary melting point apparatus.

Synthesis of epoxide 10 from S-(+)-carvone as illustrated in FIG. 3. A solution of 4 N NaOH (48 mL, 192.0 mmol, 0.3 equivalents) was slowly added to a solution of S-(+)-carvone (100.0 g, 665 mmol, 1.0 equivalent) in MeOH (1000 mL) at 0° C., followed by the dropwise addition of 35% hydrogen peroxide solution (70.0 mL, 792.6 mmol, 1.2 equivalents) over 3 hours. After the reaction was complete as established by TLC analysis, it was quenched by the slow addition of saturated Na2SO3 solution (200 mL) and extracted with CH2Cl2 (3×300 mL). The organic extracts were dried over Na2SO4 and concentrated to afford the carvone epoxide product which was used without further purification. A solution of this epoxide (101.8 g, 612.4 mmol, 1.0 equivalent) and PtO2 (0.72 g, 3.18 mmol, 0.095 equivalents) in EtOH (500 mL) was stirred under a hydrogen atmosphere (1 atm) at 25° C. for 12 hours. The reaction mixture was then filtered through a celite pad eluting with Et2O and concentrated. The crude product was purified by flash chromatography (silica gel, 5% EtOAc in hexane) to afford epoxide 10 (97.8 g, 87%, two steps) as a colorless oil. Rf=0.40 (silica gel, EtOAc-hexane, 1:10); FT-IR (neat) nmax 2959, 2873, 1708, 1466, 1438, 1369, 1111, 884, 814 cm$^{-1}$.

Synthesis of 11 through a formaldehyde aldol reaction as illustrated in FIG. 3. To a solution of diisopropylamine (14.06 mL, 107.26 mmol, 1.2 equivalents) in THF (400 mL) at −78° C. was added a solution of 1.6 M n-BuLi in hexanes (67.1 mL, 107.3 mmol, 1.2 equivalents). The reaction was then allowed to warm-up to 0° C. and stirred for 30 min after which a solution of ketone 10 (15.0 g, 89.2 mmol, 1.0 equivalent) in THF (100 mL) was added dropwise via cannula at −78° C. over 1.5 h and stirring continued for 30 min thereafter. A solution of formaldehyde, prepared by cracking paraformaldehyde (33.0 g, 1.10 mol, 12.2 equivalents) at 140° C. and bubbling the resulting gas through THF (500 mL) at −78° C. for 45 min, was added to the enolate solution via cannula over 1 h at −78° C.. The reaction mixture was then allowed to warm to 0° C., quenched by addition of saturated NH4Cl solution (100 mL), and extracted with ether (3×300 mL). The combined organic extracts were dried over Na2SO4 and concentrated. The crude product was filtered through a short pad of silica and eluted with 10% EtOAc in hexane to afford the corresponding alcohol (ca. 10.9 g, ca. 63%). To a solution of this alcohol (10.9 g, 55.0 mmol, 1.0 equivalent), triethylamine (46 mL, 330 mmol, 6.0 equivalents), and 4-DMAP (328 mg, 2.68 mmol, 0.05 equivalents) in CH2Cl2 (200 mL) at 0° C. was added TBSCl (9.9 g, 66.0 mmol, 1.2 equivalents). The reaction mixture was stirred at 25° C. for 12 h and, after the end of the reaction was established by TLC analysis, quenched via addition of MeOH (10 mL) and water (100 mL). The organic layer was separated, dried over Na2SO4 and concentrated. The crude product was purified by flash chromatography (silica gel, 3% EtOAc in hexane) to afford silyl ether 11 (8.21 g, 53%, two steps). Rf=0.70 (silica gel, EtOAc-hexane, 1:10); FT-IR (neat) nmax 2958, 2931, 2856, 1705, 1471, 1254, 1109, 882, 835, 777 cm$^{-1}$.

Synthesis of 12 through enantioselective reduction of ketone 11 as illustrated in FIG. 3. To a solution of ketone 11 (19.2 g, 61.4 mmol) in THF (300 mL) at −78° C. was added 1.0 M L-Selectride in THF (73.7 mL, 73.7 mmol, 1.2 equivalents) via cannula over 1.5 hours. The reaction mixture was stirred at the same temperature for an additional 30 min and, after the complete consumption of the starting ketone was established by TLC, quenched by addition of saturated NH4Cl solution (100 mL) and allowed to warm to 0° C. Excess 35% hydrogen peroxide (8.0 mL, 79.8 mmol, 1.3 equivalents) solution was then added and the mixture was stirred at 0° C. for 1 hour. The reaction mixture was extracted with EtOAc (3×200 mL) and the organic extracts were dried over Na2SO4 and concentrated. The crude product was purified by flash chromatography (silica gel, 5% EtOAc in hexane) to afford the secondary alcohol 12 (18.0 g, 93%) as a light yellow colored oil. Rf=0.32 (silica gel, EtOAc-hexane, 1:10); FT-IR (neat) 3553, 3506, 2955, 2882, 1471, 1436, 1388, 1266, 1255, 1092, 1068, 1006, 960, 905, 836, 776 cm$^{-1}$.

Synthesis of allylic alcohol 13 via the corresponding mesylate as illustrated in FIG. 3. To a solution of alcohol 12 (29.0 g, 92.2 mmol, 1.0 equivalent) and triethylamine (33.8 mL, 243.0 mmol, 2.6 equivalents) in CH2Cl2 (250 mL) at 0° C. was added methanesulfonyl chloride (8.2 mL, 106.3 mmol, 1.15 equivalents) dropwise over 1 hour. The reaction mixture was stirred at 0° C. for 2 h (the progress of the reaction was monitored by TLC), quenched by addition of brine, and extracted with EtOAc (3×300 mL). The combined organic extracts were dried over Na2SO4 and concentrated. The product was filtered through a short pad of silica gel eluting with ether to afford the expected mesylate which was immediately used for the next step without further purification. To a solution of NaC10H8, prepared by the addition of Na-metal (12.3 g, 535.6 mmol, 5.8 equivalents) to naphthalene (80.3 g,. 627.1 mmol, 6.8 equivalents) in THF (1800 mL) and allowing the mixture to stir for 2 hours, was added a solution of the mesylate in THF (300 mL) dropwise via cannula at 0° C. The reaction mixture was stirred for 30 min (TLC monitoring), quenched by addition of saturated NH4Cl solution (200 mL), treated with brine and extracted with EtoAc (3×300 mL). The organic extracts were dried over Na2SO4 and concentrated. The crude product was purified by flash chromatography (silica gel, 10% EtO2 in hexane followed by 10% EtOAc in hexane) to afford allylic alcohol 13 (24.2 g, 85%, two steps) as a colorless oil. Rf=0.53 (silica gel, EtOAc-hexane, 1:3); FT-IR (neat) nmax 3351, 2956, 2931, 2857, 1468, 1254, 1095, 1058, 837, 776 cm$^{31\ 1}$.

Synthesis of key-intermediate aldehyde 14 as illustrated in FIG. 3. A mixture of alcohol 13 (1.61 g, 5.42 mmol, 1.0 equivalent), triethyl orthoacetate (39.6 mL, 216.8 mmol, 40.0 equivalents), and proprionic acid (0.04 mL, 0.542 mmol, 0.1 equivalents) was heated at 170° C. for 72 hours. The excess triethyl orthoacetate was removed by vacuum distillation (25 mm Hg), and the remaining residue was purified by flash chromatography (silica gel, 3% EtOAc in hexane) to produce the expected ethyl ester (1.50 g, 74%) which was used for the next step without further purification. A 1.0 M CH2Cl2 solution of DIBAL (4.6 mL, 4.60 mmol, 1.2 equivalents) was gradually added to a solution of the ethyl ester (1.41 g, 3.83 mmol, 1.0 equivalent) in CH2Cl2 (19 mL) at −78° C., and the reaction mixture was stirred for 30 min at that temperature.

Quenching was performed by addition of saturated NH4Cl solution (20 mL) and stirring for 2 h at ambient temperature. The organic layer was separated, dried over Na2SO4 and concentrated. The residue was purified by flash chromatography (silica gel, 5% EtOAc in hexane) to provide aldehyde 14 (1.20 g, 97%) as a colorless oil. Data for ethyl ester: Rf=0.34 (silica gel, EtOAc-hexane, 1:30); FT-IR (neat) nmax 2929, 2857, 1738, 1470, 1369, 1255, 1156, 1100, 837, 775 cm$^{-1}$.

Synthesis of α,β-unsaturated ester 15 as illustrated in FIG. 4. To a THF (30 mL) suspension of sodium hydride (60% w/w in mineral oil, 542 mg, 13.55 mmol, 2.0 equivalents) was gradually added a solution of triethyl phosphonoacetate (2.7 mL, 13.55 mmol, 2.0 equivalents) in THF (10 mL) via cannula at 0° C. After the addition was complete the reaction mixture was stirred at 25° C. for 30 min before being cooled back down to 0° C. A solution of aldehyde 14 (2.20 g, 6.78 mmol, 1.0 equivalent) in THF (15 mL) was slowly added to the reaction mixture via cannula at 0° C., and the reaction mixture was stirred at the same temperature for 1 h and at 25° C. for 4 hours. After the end of the reaction was established by TLC, the reaction mixture was quenched by the addition of saturated NH4Cl solution (50 mL), extracted with ether (2×100 mL), dried over Na2SO4, and concentrated. The residue was purified by flash chromatography (silica gel, 2% EtOAc in hexane) to furnish the a,b-unsaturated ester 15 (2.67 g, 100%) as a colorless oil. Rf=0.53 (silica gel, EtOAc-hexane, 1:10); FT-IR (neat) nmax 2956, 1722, 1651, 1465, 1367, 1258, 1159, 1078, 841 cm$^{-1}$.

Synthesis of allylic alcohol 16 from ester 15 as illustrated in FIG. 4. A 1.0 M CH2Cl2 solution of DIBAL (12.2 mL, 12.20 mmol, 4.0 equivalents) was gradually added to a solution of a,b-unsaturated ethyl ester 15 (1.20 g, 3.05 mmol, 1.0 equivalent) in CH2Cl2 (15 mL) at −78° C., and the reaction was stirred for 2 h at the same temperature. The reaction mixture was quenched by addition of saturated NH4Cl solution (30 mL), stirred vigorously at ambient temperature for 2 hours, extracted with CH2Cl2 (3×50 mL), dried over Na2SO4 and concentrated. The residue was purified by flash chromatography (silica gel, 10% EtOAc in hexane) to provide allylic alcohol 16 (980 mg, 91%) as a light-yellow oil. Rf=0.21 (silica gel, EtOAc-hexane, 1:10); FT-IR (neat) nmax 3326, 2925, 1464, 1385, 1253, 1106, 1005, 836, 774, 668 cm$^{-1}$.

Synthesis of epoxide 17 from allylic alcohol 16 as illustrated in FIG. 4. To a suspension of diethyl L-tartrate (0.28 mL, 1.50 mmol, 0.2 equivalents) and powdered 4 Å MS (6.8 g) in CH2Cl2 (90 mL) was added titanium(IV) isopropoxide (0.40 mL, 1.25 mmol, 0.2 equivalents) at −20° C. followed by a 5.0 M CH2Cl2 solution of tert-butyl hydroperoxide (2.7 mL, 13.5 mmol, 2.0 equivalents). After the mixture was stirred for 40 min at the same temperature, a solution of allylic alcohol 16 (2.38 g, 6.75 mmol, 1.0 equivalent) in CH2Cl2 (5 mL) was added dropwise via cannula. The reaction mixture was stirred for 8 h at the same temperature, further diluted with CH2Cl2 (150 mL) and quenched by addition of a saturated NaHCO3 solution (100 mL). The mixture was then filtered through a celite pad eluting with CH2Cl2 and the organic phase was separated, washed with water and brine, dried over Na2SO4 and concentrated. The residue was purified by flash chromatography (silica gel, 10% EtOAc in hexane) to furnish epoxy alcohol 17 (2.25 g, 91%) as a colorless oil. Rf=0.47 (silica gel, EtOAc-hexane, 1:3); FT-IR (neat) nmax 3442, 2927, 1465, 1387, 1253, 1104, 838, 775, 668 cm$^{-1}$.

Synthesis of allylic alcohol 19 through the corresponding mesylate as illustrated in FIG. 4. To a solution of epoxy alcohol 17 (1.05 g, 2.82 mmol, 1.0 equivalent) and triethylamine (2.40 mL, 16.9 mmol, 6.0 equivalents) in CH2Cl2 (28 mL) was added dropwise methanesulfonyl chloride (1.4 mL, 18.08 mmol, 4.9 equivalents) at −20° C. After 1 h (TLC monitoring), the reaction mixture was quenched by addition of saturated NH4Cl solution (20 mL), extracted with CH2Cl2 (2×50 mL), dried over Na2SO4 and concentrated. The residue was filtered through a short silica gel pad eluting with CH2Cl2, concentrated and used immediately for the next step without further purification. A solution of the mesylate in THF (28 mL) was added via cannula to a 0.3 M THF solution of sodium naphthalenide (4.7 mL, 14.1 mmol, 5.0 equivalents), generated in the same way described for the synthesis of allylic alcohol 13, at 0° C. After 10 min, the reaction mixture was quenched by addition of saturated NH4Cl solution (50 mL), extracted with ether (2×50 mL), washed with brine, dried over Na2SO4 and concentrated. The residue was purified by flash chromatography (silica gel, 5% EtOAc in hexane) to produce allylic alcohol 19 (895 mg, 90%) as a colorless oil. Rf=0.34 (silica gel, EtOAc-hexane, 1:10); FT-IR (neat) nmax 3420, 2955, 1464, 1387, 1254, 1073, 837, 775 cm$^{-1}$.

Synthesis of PMB-ether 20 as illustrated in FIG. 4. To a solution of allylic alcohol 19 (445 mg, 1.57 mmol, 1.0 equivalent) and p-methoxybenzyl 2,2,2-trichloroacetimidate (2.22 g, 7.85 mmol, 5.0 equivalents) in CH2Cl2 (8 mL) was added pyridinium p-toluenesulfonate (395 mg, 0.31 mmol, 0.2 equivalents) at 25° C. The reaction mixture was stirred for 48 h at the same temperature, and after the end of the reaction was established by TLC, quenched by addition of saturated NaHCO3 solution (10 mL). The organic phase was separated and the aqueous layer was extracted with CH2Cl2 (2×10 mL). The combined organic extracts were dried over Na2SO4 and concentrated. The residue was purified by flash chromatography (silica gel, EtOAc-pentane, 1:99) to produce PMB-ether 20 (240 mg, 89% based on 50% conversion) as a light yellow oil. Rf=0.61 (silica gel, EtOAc-hexane, 1:3); FT-IR (neat) nmax 2954, 1614, 1514, 1464, 1250, 1080, 837, 775 cm$^{-1}$.

Synthesis of methyl ketone 21 as illustrated in FIG. 4. A solution of PMB-ether 20 (135 mg, 0.285 mmol, 1.0 equivalent) and mercuric acetate (100 mg, 3.4 mmol, 1.2 equivalents) in methanol (2 mL) was stirred at 25° C. for 12 hours. The reaction mixture was then transferred to a solution of LiCl (24.1 mg, 0.568 mmol, 2.0 equivalents), PdCl2 (50.5 mg, 0.285 mmol, 1.0 equivalent) and CuCl2 (0.115 mg, 0.855 mmol, 3.0 equivalents) in methanol (1 mL) via cannula and was further stirred at 55° C. for another 3 hours. Saturated NaHCO3 (5 mL) was added, and the product was extracted with ether (20×3 mL). The organic extracts were dried over Na2SO4 and concentrated. The crude product was purified by flash chromatography (silica gel, 6% EtOAc in hexane) to furnish methyl ketone 21 (90.5 mg, 65%) as a colorless oil. Rf=0.34 (silica gel, EtOAc-hexane, 1:15); FT-IR (neat) nmax 2956, 1714, 1514, 1249, 1081, 836 cm$^{-1}$.

Synthesis of propargylic alcohol 22 as illustrated in FIG. 4. To a stirring solution of methyl ketone 21 (180 mg, 0.369 mmol, 1.0 equivalent) in CH2Cl2:THF (3:1, 20 mL) at −78° C. was added ethynylmagnesium bromide (0.5 M in THF, 11.8 mL, 5.40 mmol, 14.6 equivalents) via syringe over 15 min. The reaction was stirred for 6 h at that temperature after which it was allowed to warm to 25° C. The reaction mixture was quenched with saturated NH4Cl solution (10 mL). The aqueous layer was separated and extracted with ether (3×20 mL), and the combined organic phase was dried over Na2SO4 and concentrated. The residue was taken up in THF (2 mL) and treated with 1.0 M THF solution of TBAF (1.47 mL, 1.47 mmol, 4.0 equivalents) at 25° C. After 2 hours (TLC monitoring), the reaction was quenched with water and extracted with ethyl acetate (3×20 mL). The combined organic phase was dried over Na2SO4 and concentrated. The residue was purified by flash chromatography (silica gel, 50% EtOAc in hexane) to afford diol 22 (106 mg, 72%, two steps) as a colorless oil. Rf=0.24 (silica gel, EtOAc-hexane, 1:1); FT-IR (neat) nmax 3305, 2958, 1614, 1514, 1248, 1090, 1035, 820 cm$^{-1}$.

Synthesis of cyano ester 25 through an oxidation-Knoevenagel condensation-protection sequence as illustrated in FIG. 4. A mixture of NaHCO3 (504 mg, 5.99 mmol, 20.0 equivalents), pyridine (0.485 mL, 5.99 mmol, 20.0 equivalents), Dess-Martin periodinane (191 mg, 0.449 mmol, 1.5 equivalents), and diol 22 (0.120 g, 0.300 mmol, 1.0 equivalent) was stirred at 25° C. for 4 hours. To the reaction was then added saturated NaHCO3 solution (15 mL), and the product was extracted with ether (3×25 mL). The combined organic layers were dried over Na2SO4, filtered through celite eluting with ether and concentrated to afford aldehyde 23 that was used for the next step without further purification. To a solution of aldehyde 23 in 95% ethanol (1.8 mL) was added ethyl cyanoacetate (0.963 mL, 9.00 mmol, 30 equivalents) and b-alanine (107 mg, 1.20 mmol, 4.0 equivalents). After 72 hours at 25° C., the reaction mixture was filtered through a pad of silica gel eluting with ether and concentrated to afford a,b-unsaturated cyano ester 24, which was used for the next step without further purification. The residue of 24 was dissolved in CH2Cl2 and N,N-diisopropylethylamine (0.522 mL, 2.99 mmol, 10 equivalents) was added. The reaction was cooled to −78° C. and TMSOTf (0.288 mL, 1.49 mmol, 5.0 equivalents) was added over 15 min. After 2 hours, the reaction was quenched with excess methanol (1.0 mL) and concentrated. The resulting residue was purified by flash chromatography (silica gel, 6% EtOAc, hexane) to afford 25 (0.12 g, 71%, three steps). Rf=0.27 (silica gel, EtOAc-hexane, 1:3); FT-IR (neat) nmax 2959, 2231, 1730, 1614, 1513, 1248, 1078, 1022, 842 cm$^{-1}$.

Synthesis of α,β-unsaturated aldehyde 27 as illustrated in FIG. 4. To a solution of cyano ester 25 (280 mg, 0.497 mmol, 1.0 equivalent) in hexanes (25 mL) at −78° C. was added dropwise a 1.0 M THF solution of DIBAL (5.0 mL, 5.0 mmol, 10.0 equivalents). After 7 hours at −78° C. and 1 h at −40° C., EtOAc (5 mL) was added and the reaction mixture was warmed to 25° C. Addition of water (30 mL) and stirring for 1 h at ambient temperature completed the workup procedure. The reaction mixture was extracted with ether (3×50 mL), dried over Na2SO4 and concentrated. The product was purified by flash chromatography (silica gel, 10% EtOAc in hexane) to afford alcohol 26 (210 mg, 80%). To a solution of 26 (50.0 mg, 0.0949 mmol, 1.0 equivalent) in CH2Cl2 (0.95 mL) was added N,N-diisopropylethylamine (0.33 mL, 1.90 mmol, 20.0 equivalents) and the resulting mixture was cooled to −78° C., after which TIPSOTf (0.26 mL, 0.95 mmol, 10.0 equivalents) was added dropwise. After 1 hour (TLC monitoring), the reaction mixture was quenched by the addition of MeOH (0.2 mL). After 10 min, aqueous saturated NH4Cl solution (5 mL) was added and the mixture was warmed to 25° C., extracted with ether (10 mL) and concentrated. The residue was purified by flash chromatography (silica gel, 2% EtOAc in hexane) to furnish TIPS ether 27 (58.8 mg, 91%) as a colorless oil. Rf=0.33 (silica gel, EtOAc-hexane, 1:10); FT-IR (neat) nmax 3470, 3300, 2957, 2360, 2337, 1672, 1613, 1513, 1418, 1370, 1302, 1250 cm$^{-1}$.

Synthesis of diastereoisomeric diols 29 as illustrated in FIG. 6. To a solution of ethyl vinyl ether (1.16 g, 16.0 mmol, 2.0 equivalents) in THF (70.0 mL) at −78° C. was added 1.7 M t-BuLi in hexanes (8.5 mL, 14.4 mmol, 1.8 equivalents), and the solution was warmed to 0° C. The reaction was followed by the color change from yellow to colorless. The resulting vinyl-anion solution was then cooled to −78° C. and a solution of aldehyde 14 (2.60 g, 8.02 mmol, 1.0 equivalent) in THF (25 mL) was added dropwise, after which the reaction mixture was stirred for an additional 30 min at −78° C. The reaction was quenched by addition of saturated NH4Cl solution (40 mL) and extracted with ether (3×150 mL). The combined organic extracts were dried over MgSO4 and concentrated. The crude product was then dissolved in ether and treated with concentrated H2SO4 in a separatory funnel while shaking vigorously. The progress of the hydrolysis was followed by TLC and, upon completion, the ether solution was washed with water (20 mL) and saturated NaHCO3 solution (20 mL), dried over MgSO4 and concentrated. The residue was purified by flash chromatography (silica gel, 10% to 15% Et2O in hexane) to produce hydroxy ketones 28 as an inseparable mixture of stereoisomers (ca. 1.25:1 by NMR). To a solution of mixture 28 in THF (78 mL) at −78° C. was added ethynyl magnesium bromide (0.5M in THF, 70.8 mL, 35.0 mmol, 4.4 equivalents) and the solution was stirred at −78° C. for 6 h and then was allowed to slowly warm to −10° C. The reaction mixture was quenched by addition of saturated NH4Cl solution (50 mL) and extracted with ether (3×100 mL). The combined organic extracts were dried over MgSO4 and concentrated, and the resulting residue was purified by flash chromatography (silica gel, 10% to 25% Et2O in hexane) to afford the desired 29 (1.39 g, 44%) along with its C-7, C-8 stereoisomer (1.04 g, 33%). 29: Rf=0.40 (silica gel, Et2O-hexane,1:3).

Synthesis of triol 30 as illustrated in FIG. 6. To a solution of diol 29 (0.63 g, 1.59 mmol, 1.0 equivalent) in THF (16 mL) at 0° C. was added TBAF (1.0M in THF, 3.18 mL, 3.18 mmol, 2.0 equivalents) and the reaction mixture was allowed to warm to 25° C. over 1 hour. After the end of the reaction was established by TLC, the solution was quenched by addition of saturated NH4Cl (50 mL) and extracted with ether (3×100 mL). The combined organic extracts were concentrated and the residue was purified by filtration through silica gel to furnish triol 30 (0.45 g, 100%) as a light yellow oil. Rf=0.12 (silica gel, Et2O-hexane, 3:1); FT-IR (neat) nmax 3385, 2958, 1448, 1368, 1078, 946 cm$^{-1}$.

Synthesis of trisilyl ether 31 as illustrated in FIG. 6. To a solution of triol 30 (0.45 g, 1.59 mmol, 1.0 equivalent) in CH2Cl2 (16 mL) was added triethylamine (2.3 mL, 16.5 mmol, 10.3 equivalents) and the solution was chilled to 0° C. TESOTf (2.10 g, 8.00 mmol, 5.0 equivalents) was then added and the reaction mixture was allowed to warm to 25° C. After the disappearance of the starting triol was established by TLC, the solution was quenched by addition of saturated NH4Cl (50 mL) and extracted with CH2Cl2 (3×100 mL). The organic extracts were combined, dried over MgSO4 and concentrated. The residue was purified by filtration through silica gel (25% Et2O in hexane) to produce trisilyl ether 31 (0.99 g, 100%) as a light yellow oil. Rf=0.62 (silica gel, Et2O-hexane, 1:9); FT-IR (neat) nmax 3308, 2956, 2876, 1459, 1414, 1378, 1239, 1115, 1006 cm$^{-1}$.

Selective deprotection of the primary hydroxide to produce alcohol 32 as illustrated in FIG. 6. To a solution of trisilyl ether 31 (1.48 g, 2.37 mmol, 1.0 equivalent) in 3:1 MeOH/CH2Cl2 (20 mL) was added a catalytic amount of PPTS (45 mg, 0.24 mmol, 0.1 equivalents). After its completion (TLC monitoring), the reaction mixture was worked up by addition of saturated NaHCO3 (50 mL) and extraction with ether (3×150 mL). The combined organic extracts were dried over MgSO4 and concentrated. The residue was purified by filtration through silica gel eluting with ether to provide alcohol 32 (1.18 g, 98%) as a colorless oil. Rf=0.12 (silica gel, Et2O-hexane, 1:9); FT-IR (neat) nmax 3490, 3308, 2955, 2876, 1459, 1414, 1378, 1238, 1109, 1072, 1004 cm$^{-1}$.

Synthesis of aldehyde 33 as illustrated in FIG. 6. To a solution of alcohol 32 (1.24 g, 2.43 mmol, 1.0 equivalent) and powdered activated 4 Å MS (0.5 g) in CH2Cl2 (16 mL) was added NMO (0.43 g, 3.64 mmol, 1.5 equivalents) and the reaction mixture was stirred for 10 min. TPAP (0.043 g, 0.181 mmol, 0.07 equivalents) was then added and the reaction mixture was stirred at 25° C. for 30 min. The heterogeneous solution was then filtered through a short pad of silica gel and washed with CH2Cl2. After concentration, aldehyde 33 (1.20 g, 98%) was obtained as a colorless oil. Rf=0.42 (silica gel, Et2O-hexane, 1:9); FT-IR (neat) nmax 3309, 2955, 2876, 1719, 1458, 1414, 1378, 1238, 1073, 1004 cm$^{-1}$.

Formation of a,b-unsaturated cyano ester 34 as illustrated in FIG. 6. A solution of aldehyde 33 (1.14 g, 2.25 mmol, 1.0 equivalent), ethyl cyanoacetate (7.63 g, 67.0 mmol, 30 equivalents), and b-alanine (0.080 g, 9.00 mmol, 4.0 equivalents) in EtOH (15 mL) was stirred at 50° C. for 72 hours. The reaction mixture was then concentrated and purified by filtration through a short pad of silica gel eluting with 10% Et20 in hexanes to produce cyano ester 34 (1.28 g, 95%) as a colorless oil. Rf=0.40 (silica gel, Et2O-hexane, 1:9); FT-IR (neat) nmax 3308, 2958, 2878, 2201, 1735, 1619, 1461, 1370, 1249, 1117, 1008 cm$^{-1}$.

Synthesis of hydroxyaldehyde 35 as illustrated in FIG. 6. To a solution of cyanoester 34 (101 mg, 0.168 mmol, 1.0 equivalent) in hexanes (8.4 mL) at −78° C. was added DIBAL (1.0 M in toluene, 1.7 mL, 1.70 mmol, 10.0 equivalents). The reaction mixture was stirred for 6 h at −78° C. and then slowly warmed to −10° C. for 2 hours. The solution was then quenched with ethyl acetate (0.2 mL), saturated NH4Cl (10 mL) solution was added, and the reaction was stirred for 2 hours, after which it was filtered through a short celite pad eluting with ether and extracted with ethyl acetate (3×10 mL). The combined organic extracts were concentrated and purified by flash chromatography (silica gel, 10% Et2O in hexanes) to produce hydroxyaldehyde 35 (79.8 mg, 90%) as a light yellow oil. Rf=0.42 (silica gel, Et2O-hexane, 1:1); FT-IR (neat) nmax 3447, 3307, 2957, 2877, 1677, 1459, 1414, 1380, 1239, 1117, 1008 cm$^{-1}$.

Synthesis of trisilyl ether 36 as illustrated in FIG. 6. To a solution of hydroxyaldehyde 35 (930.0 mg, 1.65 mmol, 1.0 equivalent) and iPr2NEt (2.8 mL, 16.07 mmol, 9.7 equivalents) in CH2Cl2 (8 mL) at −78° C. was added TIPSOTf (2.2 mL, 8.25 mmol, 5.0 equivalents), and the solution was stirred at that temperature for 1 hour. The reaction mixture was quenched by addition of MeOH (0.5 mL) followed by addition of saturated NH4Cl (10 mL). The mixture was then extracted with ether (10 mL), and the organic extracts were combined, dried over Na2SO4 and concentrated. The resulting residue was purified by flash chromatography (silica gel, 2% EtOAc-hexane) to furnish trisilyl ether 36 (1.10 g, 93%) as a light yellow oil. Rf=0.33 (silica gel, hexane); FT-IR (neat) nmax 3309, 2957, 2872, 2361, 1675, 1462, 1381, 1239, 1167, 1117, 1007, 882, 819, 741 cm$^{-1}$.

Synthesis of alkynone 37 by intramolecular acetylide addition to aldehyde 27 as illustrated in FIG. 7. A solution of LiHMDS (1.0 M in THF, 0.037 mL, 0.037 mmol, 1.5 equivalents) was added dropwise to a solution of aldehyde 27 (17.0 mg, 0.025 mmol, 1.0 equivalent) in THF (1.2 mL) at 25° C. After 10 min (TLC monitoring), the reaction mixture was quenched by the addition of aqueous saturated NH4Cl solution (5 mL), extracted with ether (2×10 mL), dried over Na2SO4 and concentrated. The residue was redissolved in CH2Cl2 (1.0 mL) and NaHCO3 (41.8 mg, 0.497 mmol, 20 equivalents) was added to the solution at 0° C. After 40 min, Dess-Martin periodinane (10.6 mg, 0.025 mmol, 1.0 equivalent) was added to the reaction mixture at the same temperature, and the solution was warmed to 25° C. After stirring for 4 h at ambient temperature, the reaction mixture was diluted with ether (5 mL) and quenched by the consecutive addition of saturated aqueous NaHCO3 solution (5 mL) and sodium thiosulfate pentahydrate (Na2S2O3.5H2O, 65 mg, 0.261 mmol, 10.4 equivalents). The resulting solution was extracted with ether (2×10 mL), and the combined organic extracts were dried over Na2SO4 and concentrated. The crude product was purified by flash chromatography (silica gel, 1% EtOAc in hexane) to provide enyneone 37 (14.4 mg, 85%, two steps) as a colorless oil. Rf=0.46 (silica gel, EtOAc-hexane, 1:10); FT-IR (neat) nmax 2961, 2361, 2197, 1650, 1611, 1512, 1461, 1384, 1461, 1384, 1248, 1175, 1095, 1035, 841, 760, 685 cm$^{-1}$.

Synthesis of propargylic alcohol 38 as illustrated in FIG. 7. To a solution trimethylsilyl ether 37 (3.2 mg, 0.0047 mmol, 1.0 equivalent) in MeOH (1 mL) was added, at 25° C., PPTS (1.18 mg, 0.0047 mmol, 1.0 equivalent), and the reaction mixture was allowed to stir at ambient temperature for 30 min. The reaction was quenched by addition of saturated NaHCO3 solution (1 mL) and extracted with ether (2×10 mL). The combined organic extracts were dried over Na2SO4 and concentrated. The crude product was purified by flash chromatography (silica gel, 15% EtOAc in hexane) to provide alcohol 38 (2.7 mg, 94%) as a colorless oil. Rf=0.45 (silica gel, EtOAc-hexane, 1:3).

Synthesis of the basic tricyclic core 40 as illustrated in FIG. 7. To a solution of alkynone 38 (6.2 mg, 0.0135 mmol, 1.0 equivalent) in toluene (1 mL) was added 5% Pd on CaSO4 treated with Pb (Lindlar cat., 14.0 mg, 0.00675 mmol, 0.5 equivalents) at 25° C. under argon. This suspension was then stirred under a H2 atmosphere (1 atm) at the same temperature for 20 min, and the reaction mixture was filtered through celite and concentrated. The crude residue was purified by flash chromatography (silica gel, 10% EtOAc-hexanes) to produce hemiketal 40 (6.2 mg, 75%) as a colorless oil, along with its 5,6-dihydro analog (1.5 mg, 15%). Rf=0.55 (silica gel, EtOAc-hexane, 1:3); FT-IR (neat) nmax 3418, 2866, 1615, 1515, 1463, 1248, 1017 cm$^{-1}$.

Synthesis of methyl ketal 41 as illustrated in FIG. 7. To a solution of hemiketal 40 (4.0 mg, 0.0066 mmol, 1.0 equivalent) in MeOH (0.5 mL) was added PPTS (1.65 mg, 0.0066 mmol, 1.0 equivalent). After 10 min, the reaction was quenched by addition of saturated NaHCO3 solution (5 mL). The bi-phasic system was then extracted with CH2Cl2,(3× 10 mL) and the organic extracts were combined, dried over Na2SO4 and concentrated. The product was purified by flash chromatography (silica gel, 5% EtOAc in hexane) to furnish ketal 41 (4.5 mg, 100%) as a light yellow oil. Rf=0.68 (silica gel, EtOAc-hexane, 1:3); FT-IR (neat) nmax 2957, 2866, 1614, 1514, 1463, 1250, 1064 cm$^{-1}$.

Synthesis of alcohol 42 from PMB ether 41 as illustrated in FIG. 7. A solution of ether 41 (5.0 mg, 0.0080 mmol, 1.0 equivalent) in THF (1 mL) and EtOH (2 drops) was added to liq. NH3 (2 mL) at −78° C. Sodium (1.8 mg, 0.078 mmol, 9.8 equivalents) was then added, and the reaction was stirred at −78° C. for 20 min. After the end of the deprotection was established by TLC, the reaction was quenched by addition of solid NH4Cl (50 mg), warned to ambient temperature to evaporate the NH3, extracted with ether (3×10 mL), dried with Na2SO4, concentrated and purified by flash chromatography (silica gel, 15% EtOAc in hexane) to provide alcohol 42 along with its 5,6-dihydro analog 43 as an inseparable mixture (ca. 2:1, 3.8 mg, 95%).

Synthesis of alcohol 42 from hydroxy alkynone 45 as illustrated in FIG. 9. To a solution of α,β-alkynone 45 (26.8 mg, 0.055 mmol, 1.0 equivalent) in acetone (3 mL) was added [Rh(nbd)(dppb)]BF4 (1.9 mg, 0.0027 mmol, 0.05 equivalents) at 25° C. under argon. The reaction flask was then evacuated and treated with hydrogen gas (1 atm). After 10 min, the reaction was quenched by addition of saturated NaHCO3 (10 mL), extracted with ether (3×10 mL), dried over Na2SO4, and concentrated to a crude residue. To a solution of this residue in MeOH (6 mL) was added PPTS (6.9 mg, 0.027 mmol, 0.5 equivalents) at 25° C. After 10 min, the reaction was quenched by addition of saturated NaHCO3, (10 mL), extracted with ether (3×20 mL), dried over Na2SO4 and concentrated. The residue was purified by flash chromatography (silica gel, 15% EtOAc in hexane) to produce methyl ketal 42 (22.2 mg, 80%, two steps) as a colorless oil. Rf=0.43 (silica gel, EtOAc-hexane, 1:3); FT-IR (neat) nmax 3456, 2940 2866, 1466, 1366, 1047, 881 cm$^{-1}$.

Synthesis of 5,6-dihydro analog 43 from hydroxy alkynone 45 as illustrated in FIG. 12. To a solution of ketone 45 (4.5 mg, 0.0092 mmol, 1.0 equivalent) in ethyl acetate (0.5 mL) was added 5% Pd on BaSO4 (19.6 mg, 0.0092 mmol, 1.0 equivalent). This suspension was stirred under a hydrogen atmosphere (1 atm) at 25° C. for 1 hour. The reaction mixture was then filtered through celite and concentrated by evaporation. To a solution of the crude residue in MeOH (0.5 mL) was added PPTS (4.6 mg, 0.018 mmol, 2.0 equivalents), and the mixture was stirred for 6 h at 25° C. A saturated solution of NaHCO3 (5 mL) was added, and the reaction mixture was extracted with ether (3×10 mL), dried over Na2SO4 and concentrated. The crude residue was purified by flash chromatography (silica gel, 15% EtOAC-hexane) to provide 5,6-dihydro methyl ketal analog 43 (3.0 mg, 64%, two steps). Rf=0.50 (silica gel, EtOAc-hexane, 1:3); FT-IR (neat) nmax 3422, 2961, 2865, 2361, 1464, 1383, 1122, 1047, 882, 684 cm$^{-1}$.

Synthesis of bicyclic alcohol 44 as illustrated in FIG. 9. To a solution of PMB-ether 37 (31.0 mg, 0.045 mmol, 1.0 equivalent) in CH2Cl2 (4.6 mL) and H2O (0.3 mL) was added DDQ (21.0 mg, 0.091 mmol, 2.0 equivalents), and the reaction was stirred at 25° C. for 30 min. After the disappearance of starting ether was established by TLC, the reaction mixture was quenched by addition of saturated NaHCO3 (3 mL), extracted with ether (3×10 mL), and dried over Na2SO4. The crude residue was purified by flash chromatography (silica gel, EtOAc-hexane, 1:99) to yield alcohol 44 (20.4 mg, 80%) as a colorless oil. Rf=0.57 (silica gel, EtOAc-hexane, 1:10); FT-IR (neat) nmax 3490, 2959, 2866, 2197, 1651, 1464, 1384, 1252, 1122, 1095, 1021, 864, 843 cm$^{-1}$.

Synthesis of alkynone 49 as illustrated in FIG. 10. To a solution of aldehyde 36 (243.0 mg, 0.338 mmol, 1.0 equivalent) in THF (17 mL) was added dropwise a 1.0 M THF solution of LiHMDS (0.68 mL, 0.68 mmol, 2.0 equivalents) at −20° C. The reaction mixture was stirred for 20 min at that temperature and then it was quenched with saturated NH4Cl solution (30 mL), extracted with ether (2×50 mL), dried over Na2SO4 and concentrated to a crude residue. A solution of this residue in CH2Cl2 (9 mL) was added to a solution of NaHCO3 (170.0 mg, 2.0 mmol, 5.9 equivalents), pyridine (0.16 mL, 2.0 mmol, 5.9 equivalents) and Dess-Martin reagent (286.0 mg, 0.67 mmol, 2.0 equivalents) in CH2Cl2 (9 mL) at 0° C. The reaction was stirred for 1 h at the same temperature and then it was quenched by consecutive addition of saturated NaHCO3 (20 mL) and Na2S2O3.5H2O (1.17g, 4.7 mmol, 13.9 equivalents). It was stirred for an additional 30 min, extracted with ether (2×50 mL), dried over Na2SO4 and concentrated. This crude residue was then purified by flash chromatography (silica gel, 0.5% EtOAc in hexane) to produce bicyclic alkynone 49 (216 mg, 89%, two steps) as a light yellow oil. Rf=0.74 (silica gel, EtOAc-hexane, 1:10); FT-IR (neat) nmax 2957, 2362, 1652, 1460, 1383, 1212, 1114, 1004, 883, 732, 684 cm$^{-1}$.

Synthesis of diol 45 as illustrated in FIG. 10. To a solution of trisilyl ether 49 (200 mg, 0.28 mmol, 1.0 equivalent) in THF (1 mL) was added Et3N.3HF (0.23 mL, 1.40 mmol, 5.0 equivalents) at 25° C. After 1.5 hours, the reaction mixture was cooled to 0° C., quenched by addition of NaHCO3 (10 mL), extracted with ether (3×10 mL), dried over Na2SO4 and concentrated. The residue was purified by flash chromatography (silica gel, 25% EtOAc in hexane) to produce diol 45 (107 mg, 78%) as a colorless oil. Rf=0.26 (silica gel, EtOAc-hexane, 1:3); FT-IR (neat) nmax 3411, 2941, 2867, 2202, 1650, 1465, 1385, 1207, 1089, 1018, 883, 757, 685 cm$^{-1}$.

Synthesis of mixed anhydride of the aromatic side chain 52 as illustrated in FIG. 11. To a solution of ethyl ester 50 (750 mg, 4.16 mmol, 1.0 equivalent) in (1:1) THF:water (32.0 mL) at 25° C. was added LiOH.H2O (192 mg, 4.57 mmol, 1.1 equivalents) and the resulting reaction mixture was stirred at the same temperature for 12 hours. The solvent was removed under reduced pressure, and the solid was azeotroped with benzene (5 mL×5) and finally dried under high vacuum. The acid salt 51 was used without further purification. To a solution of 51 in THF (40 mL) at 25° C. was added Piv-Cl (0.54 mL, 4.58 mmol, 1.1 equivalents) and the reaction mixture was stirred at the same temperature for 12 hours. Once complete by TLC, the reaction mixture was filtered, and the filtrate was concentrated under reduced pressure and dried under high vacuum to give anhydride 52 (698 mg, 75%). The anhydride was stored as a 0.2 M solution in CH2Cl2 and used in this form for the esterification.

Synthesis of 53 by attachment of the aromatic side chain. A mixture of alcohol 42 (61.0 mg, 0.120 mmol, 1.0 equivalent), 4-DMAP (14.7 mg, 0.120 mmol, 1.0 equivalent), triethylamine (0.3 mL, 2.15 mmol, 17.9 equivalents) and mixed anhydride 52 (6.0 mL of 0.2 M solution in CH2Cl2, 1.22 mmol, 10.0 equivalents) was stirred at 25° C. for 22 hours. The reaction mixture was then concentrated and purified by flash chromatography (silica gel, 10:10:1, EtOAc:CH2Cl2: MeOH) to yield ester 53 (75.0 mg, 98%). Rf=0.42 (silica gel, 10:10:1, EtOAc:CH2Cl2:MeOH); FT-IR (neat) nmax 2940, 2864, 1704, 1639, 1465, 1384, 1269, 1154, 1060, 994 cm$^{-1}$.

Synthesis of alcohol 54 as illustrated in FIG. 11. To a solution of silyl ether 53 (75.0 mg, 0.117 mmol, 1.0 equivalent) in THF (2 mL) was added 1.0 M TBAF in THF (0.22 mL, 0.22 mmol, 1.9 equivalents) and the reaction was stirred for 1 h at 25° C. After completion (thin layer chromatography monitoring), the reaction mixture was concentrated and purified by flash chromatography (silica gel, 10:10:1, EtOAc:CH2Cl2:MeOH) to provide alcohol 54 (50.0 mg, 89%). Rf=0.23 (silica gel, 10:10:1, EtOAc:CH2Cl2:MeOH); FT-IR (neat) nmax 3380, 2961, 2361, 1700, 1636, 1450, 1382, 1269, 1156, 1036, 731 cm$^{-1}$.

Synthesis of aldehyde 55 as illustrated in FIG. 11. To a solution of allylic alcohol 54 (50 mg, 0.104 mmol, 1.0 equivalent) in CH2Cl2 (2 mL) was added NaHCO3 (88.0 mg, 0.595 mmol, 10.0 equivalents) and Dess-Martin reagent (84.8 mg, 0.20 mmol, 2.0 equivalents), and the reaction was stirred for 30 min at ambient temperature, after which isopropanol (0.1 mL) was added followed by ethyl acetate (10 mL). The precipitate was filtered off and the filtrate was concentrated and purified by flash chromatography (silica gel, 10:10:1, EtOAc:CH2Cl2:MeOH) to yield aldehyde 55 (49.5 mg, 100%). Rf=0.43 (silica gel, 10:10:1, EtOAc:CH2Cl2:MeOH).

Synthesis of methyl ester 57 with the intermediacy of acid 56 as illustrated in FIG. 11. To a solution of aldehyde 55 (14.0 mg, 0.0291 mmol, 1.0 equivalent) in t-BuOH:H2O (5:1, 1.2 mL total) was added 2.0 M 2-methyl-2-butene in THF (1 mL, 2.0 mmol, 68.7 equivalents), NaH2PO4 (10.5 mg, 0.087 mmol, 2.9 equivalents) and NaClO2 (15.7 mg, 0.174 mmol, 6.0 equivalents) at 0° C. The reaction was stirred at the same temperature for 2 hours, after which an ether solution of CH2N2 (excess) was added and the reaction was stirred for an additional 10 min at 25° C. The excess CH2N2 was removed by an argon stream, the reaction was extracted with ethyl acetate (3×15 mL), dried over Na2SO4 and concentrated. The crude residue was purified by flash chromatography (silica gel, 10:10:1 EtOAc:CH2Cl2:MeOH) to furnish methyl ester 57 (13.1 mg, 88%, two steps). Rf=0.42 (silica gel, 10:10:1 EtOAc:CH2Cl2:MeOH); FT-IR (neat) nmax 3410, 2960, 1711, 1637, 1435, 1384, 1269, 1155, 1048, 732 $cm^{-1}$.

Completion of the synthesis for sarcodictyin A (7) as illustrated in FIG. 11. To a solution of methyl ester 57 (6.0 mg, 0.0117 mmol, 1.0 equivalent) in 10:1 CH2Cl2:H2O (1.1 mL) was added CSA (10 mg, 0.043 mmol, 6.4 equivalents) and the reaction was stirred at 25° C. for 16 hours, after which triethylamine was added and the reaction mixture was concentrated. The crude mixture was purified by flash chromatography (silica gel, 10:10:1, EtOAc:CH2Cl2:MeOH) to yield sarcodictyin A (7) (4.6 mg, 79%) as a white solid. Rf=0.32 (silica gel, 10:10:1, EtOAc:CH2Cl2:MeOH); FT-IR (neat) nmax 2958, 2361, 1711, 1636, 1244, 1153, 1050 $cm^{-1}$.

Synthesis of ethyl ester 58 as illustrated in FIG. 11. To a solution of aldehyde 55 (27.8 mg, 0.058 mmol, 1.0 equivalent) in t-BuOH:H2O (5:1, 1.2 mL total) was added 2.0 M 2-methyl-2-butene in THF (1 mL, 2.0 mmol, 34.4 equivalents), NaH2PO4 (20.9 mg, 0.174 mmol, 3.0 equivalents) and NaClO2 (31.5 mg, 0.340 mmol, 2.9 equivalents) at 0° C. The reaction was stirred at the same temperature for 2 hours, after which an ether solution of excess CH3CHN2 was added and the reaction was stirred for an additional 10 min at 25° C. The excess CH3CHN2 was removed by an argon stream, the reaction was extracted with ether (2×15 mL), dried over Na2SO4 and concentrated. The crude residue was purified by flash chromatography (silica gel, 10:10:1 EtOAc:CH2Cl2:MeOH) to yield ethyl ester 58 (27.0 mg, 89%, two steps). Rf=0.41 (silica gel, 10:10:1 EtOAc:CH2Cl2:MeOH); FT-IR (neat) nmax 2963, 1708, 1636, 1269, 1154, 1048 $cm^{-1}$.

Completion of the synthesis of sarcodictyin B (8) as illustrated in FIG. 11. To a solution of ethyl ester 58 (3.5 mg, 0.0067 mmol, 1.0 equivalent) in 10:1 CH2Cl2:H2O (1.1 mL) was added CSA (10.0 mg, 0.043 mmol, 6.4 equivalents) and the reaction was stirred at 25° C. for 24 hours, after which triethylamine was added and the reaction mixture was concentrated. The crude mixture was purified by flash chromatography (silica gel, 10:10:1 EtOAc:CH2Cl2:MeOH) to yield sarcodictyin B (8) (3.0 mg, 86%) as a white solid. Rf=0.32 (silica gel, 10:10:1 EtOAc:CH2Cl2:MeOH); FT-IR (neat) nmax 3348, 2926, 2855, 1708, 1637, 1458, 1383, 1299, 1271, 1244, 1156, 1051 $cm^{-1}$.

Synthesis of C5,C6-saturated analog 61 as illustrated in FIG. 12. Analog 61 was synthesized by the same reaction sequence followed for the two natural products (53, 54, 55, 56, 57, 58) from alcohol 43. Rf=0.32 (silica gel, 10:10:1, EtOAc:CH2Cl2:MeOH); FT-IR (neat) nmax 2959, 1711, 1638, 1451, 1247, 1159, 1043 $cm^{-1}$.

Synthesis of mixed anhydride resin 100 as illustrated in FIG. 14: A suspension of hydroxymethyl polystyrene resin (5.00 g, 4.00 mmol, 1.0 equivalent) in CH2Cl2 (50 mL) at 25° C. was treated with Et3N (2.79 mL, 20.0 mmol, 5.0 equivalents) and glutaric anhydride (1.87 g, 16.0 mmol, 4.0 mmol). The reaction mixture was stirred gently (<300 rpm) over 8 hours at 25° C. after which time it was poured into a fritted funnel, washed with CH2Cl2 (50 mL), MeOH (50 mL), CH2Cl2 (3×50 mL), and ether (2×200 mL) and dried to constant weight under high vacuum. The resulting resin was resuspended in CH2Cl2 (50 mL) at 25° C. and treated with Et3N (2.79 mL, 20.0 mmol, 5.0 equivalents) followed by pivaloyl chloride (1.44 g, 12.0 mmol, 3.0 equivalents). The reaction mixture was stirred gently over 6 hours at 25° C. after which time it was poured into a fritted funnel, washed with the following distilled solvents under an argon atmosphere: CH2Cl2 (50 mL), Et2O (50 mL), CH2Cl2 (3×50 mL), and Et2O (2×200 mL) and dried to constant weight under high vacuum (5.60 g). A two-step yield of >90% was determined by titration of the mixed anhydride resin with benzyl alcohol. Thus, in three separate experiments, the mixed anhydride resin (300 mg, 0.207 mmol, 1.0 equivalent) was treated with benzyl alcohol (15.6 mg, 0.145 mmol, 0.7 equivalents), (20.1 mg, 0.186 mmol, 0.9 equivalents) and (24.5 mg, 0.227 mmol, 1.1 equivalents) followed by Et3N (43.2 mL, 0.310 mmol, 1.5 equivalents) and 4-DMAP (5.0 mg, 0.041 mmol, 0.2 equivalents). TLC analysis of the reaction mixtures revealed complete consumption of the benzyl alcohol for the experiments with 0.7 and 0.9 equivalents of benzyl alcohol establishing the yield as at least 90%.

Synthesis of hydroxy resin 120 as illustrated in FIG. 14: To a suspension of NaH (60% in mineral oil, 1.76 g, 44.0 mmol, 4.0 equivalents) in DMF (100 mL) at 0° C. was added 1,4-butanediol (3.86 mL, 44.0 mmol, 4.0 equivalents) and the reaction mixture was stirred for 1 h at 0° C. Merrifield resin (10.0 g, 11.0 mmol, 1.0 equivalent) was then added to the reaction mixture followed by tetra-n-butylammonium iodide (400 mg, 0.11 mmol, 0.1 equivalents) and the mixture was stirred gently (<300 rpm) over 12 hours. The resin was poured into a fritted funnel, washed with aq. HCl (1 N, 200 mL), DMF (2×300 mL), MeOH (200 mL), CH2Cl2 (300 mL), MeOH (200 mL), CH2Cl2 (2×300 mL), and Et2O (2×200 mL) and dried to constant weight under high vacuum (9.98 g, 99% yield). A sample of this resin was suspended in CH2Cl2 at 25° C. and treated with Fmoc—Cl (5.0 equivalents) and pyridine (5.0 equivalents) for 6 hours. The reactive hydroxyl groups were photometrically quantified from the amount of Fmoc chromophore released upon treatment of the Fmoc-resin with 10% Et3N in CH2Cl2 at 25° C. for 8 hours.

Synthesis of iodo resin 13 as illustrated in FIG. 14: A suspension of hydroxy resin 12 (9.00 g, 9.39 mmol, 1.0 equivalent) in $CH_2Cl_2$ (100 mL) at 0° C. was treated sequentially with imidazole (2.55 g, 37.6 mmol, 4.0 equivalents), Ph3P (9.85 g, 37.6 mmol, 4.0 equivalents) and iodine (9.55 g, 37.6 mmol, 4.0 equivalents). The reaction mixture was stirred gently at 0° C. for 4 hours after which time it was poured into a fritted funnel, washed with CH2Cl2 (3×200 mL), MeOH (200 mL), CH2Cl2 (2×200 mL), and Et2O (2×200 mL) and dried to constant weight under high vacuum (9.95 g, >95% yield). Subjection of this resin to the Fmoc assay described in the synthesis of 120, indicated complete consumption of the alcohol.

Synthesis of phosphorane resin 140 as illustrated in FIG. 14: A mixture of iodide resin 130 (5.00 g, 4.45 mmol, 1.0 equivalent) and Ph3P (11.7 g, 44.5 mmol, 10 equivalents) in DMF (30 mL) was gently stirred at 100° C. for 15 h after which time it was poured into a fritted funnel, washed with warm (100° C.) DMF (3×200 mL), CH2Cl2 (2×200 mL) and Et2O (3×300 mL) and dried to a constant weight of 6.10 g (>95% yield based on mass gain). A portion of this resin (2.2 g, 1.57 mmol, 1.0 equivalent) was resuspended in THF (15 mL) at 25° C., LiHMDS (1.0 M in THF, 2.04 mL, 2.04 mmol, 1.3 equivalents) was added, and the reaction was allowed to stir for 2 h at ambient temperature after which time the resin adopted a deep red color. The supernatant solvent was removed by cannulation, the resin was washed with THF (3×15 mL) and the resulting resin was used for the next step without any additional treatment (>90% yield). The yield was determined as follows. The ylide was quenched with benzaldehyde (5.0 equivalents, 25° C., 6 h) and the resulting resin was subjected to ozonolysis (CH2Cl2, −78° C., 30 min) followed by a reductive workup (Me2S). The quantity of benzaldehyde recovered was quantified by HPLC absorption calibrated with an authentic benzaldehyde sample.

Acetate 180 as illustrated in FIG. 15. A solution of hydroxy compound 47 (0.404 g, 0.806 mmol, 1.0 equivalent) in CH2Cl2 (10 mL) at 25° C. was treated with pyridine (0.322 g, 4.03 mmol, 5.0 equivalents) and Ac2O (0.246 g, 2.42 mmol, 3.0 equivalents). The reaction mixture was stirred for 1 h at 25° C. after which time TLC analysis indicated complete reaction. The reaction mixture was poured into Et2O (150 mL), washed with sat. aq. NaHCO3 (3×100 mL), dried over MgSO4, and concentrated. The crude mixture was purified by flash column chromatography (silica gel, EtOAc-hexane, 1:3) to furnish pure acetate 180 (0.421 g, 96% yield). Rf=0.20 (silica gel, EtOAc-hexane, 1:3); $[\alpha]_{D25}$ +47.8 (c=2.32, CHCl3); FT-IR (neat) nmax 2942, 2866, 2363, 2334, 1739, 1720, 1459, 1364, 1239, 1034 $cm^{-1}$.

Hydroxy ketal 190 as illustrated in FIG. 15. A solution of ketal 180 (0.421 g, 0.774 mmol, 1.0 equivalent) in CH2Cl2 (5 mL) at 25° C. was treated with 1,6-hexanediol (0.913 g, 7.74 mmol, 10 equivalents) and PPTS (0.194 g, 0.774 mmol, 1.0 equivalent). The reaction mixture was stirred for 4 h at 25° C. after which time TLC analysis indicated complete reaction. The reaction mixture was loaded onto a short silica column and eluted with EtOAc-hexanes (1:2) to give pure hydroxy ketal 190 (0.450 g, 92% yield). Rf=0.15 (silica gel, EtOAc-hexanes, 1:2); $[\alpha]_{D25}$ +36.5 (c=1.0, C6H6); FT-IR (neat) nmax 3427, 2936, 2864, 1742, 1465, 1368, 1238, 1051, 1032, 880 $cm^{-1}$.

Aldehyde ketal 200 as illustrated in FIG. 15. To a solution of Dess-Martin periodinane (0.451 g, 1.07 mmol, 1.5 equivalents) in CH2Cl2 (10 mL) at 25° C. was added pyridine (0.280 g, 3.56 mmol, 5.0 equivalents) and NaHCO3 (0.598 g, 7.12 mmol, 10 equivalents). The mixture was stirred for 15 min at ambient temperature and then cooled to 0° C. Alcohol 190 (0.450 g, 0.712 mmol, 1.0 equivalent) was added as a solution in CH2Cl2 (10 mL). The reaction mixture was removed from the cold bath after 15 min and stirred for an additional 2 h at 25° C. after which time TLC analysis indicated complete reaction. The crude mixture was loaded onto a short silica gel column and eluted with EtOAc-hexane (1:3) to yield pure product 200 (0.430 g, 96% yield). Rf=0.18 (silica gel, EtOAc-hexane, 1:3); $[\alpha]_{D25}$ +29.0 (c=1.0, C6H6); FT-IR (neat) nmax 2940, 2865, 1939, 1458, 1369, 1238, 1032, 996, 880 $cm^{-1}$.

Attachment of sarcodictyin core 180 on resin 120 by transketalization as illustrated in FIG. 16. To a suspension of resin 120 (0.563 g, 0.54 mmol, 10 equivalents) in CH2Cl2 (3 mL) containing flamed-dried 4 Å molecular sieves (0.30 g) at 25° C. was added a solution of ketal 180 (28 mg, 0.054 mmol, 1.0 equivalent) in CH2Cl2 (1 mL) followed by PPTS (13 mg, 0.054 mmol, 1.0 equivalent). The reaction mixture was agitated gently on a wrist shaker at ambient temperature for 48 h and then filtered and washed with anhydrous CH2Cl2 (2×5 mL). The unreacted starting material in the combined filtrates was purified to recover 14 mg of pure 180 (50% yield based on recovered starting material). The excess alcohol on the resin was caped by resuspending the resin in DMF (3 mL) followed by addition of MOM-Cl (88 mg, 0.054 mmol, 20 equivalents) and iPr2NEt (126 mg, 1.1 mmol, 20 equivalents) for 24 h at ambient temperature. The resin was filtered in a fritted funnel, washed with CH2Cl2 (3×50 mL) containing 1% Et3N, Et2O (2×50 mL) and dried under high vacuum to a constant weight of 0.56 g (0.039 mmol/g loading of the sarcodictyin core).

Attachment of sarcodictyin core 200 on resin 140 by a Wittig reaction as illustrated in FIG. 16. To a suspension of ylide 140 (0.75 mmol, 7.0 equivalents) in THF (2 mL) cooled to −78° C. was added a solution of aldehyde 200 (67.6 mg, 0.107 mmol, 1.0 equivalent) in THF (5 mL). The reaction mixture was allowed to warm up slowly to ambient temperature over 2 h and was stirred for an additional 2 h at 25° C., after which time TLC analysis indicated complete consumption of the aldehyde (>95% yield). The excess ylide was quenched by the addition of acetaldehyde (99 mg, 2.25 mmol, 21 equivalents), the resin was collected on a fritted funnel, washed with THF (3×50 mL) containing 1% Et3N, Et2O (2×50 mL) and dried under high vacuum to a constant weight of 836 mg (0.128 mmol/g loading of the sarcodictyin core). In a cleavage demonstration experiment, a sample of this resin (225 mg, 28.8 mmol, 1.0 equivalent) was treated with PPTS (14.3 mg, 57.6 mmol, 2.0 equivalents) in MeOH (0.5 mL) at 25° C. for 30 h to recover, after purification (silica gel, flash column chromatography), 14.2 mg of the corresponding methyl ketal (90% for 2 steps).

Hydrolysis of acetate 240 and formation of polymer-bound alcohol 250 as illustrated in FIG. 17. To a suspension of resin 240 (3.12 g, 0.40 mmol, 1.0 equivalent) in THF (20 mL) was added NaOMe (0.5 M in MeOH, 4.0 mL, 2.0 mmol, 5.0 equivalents). The reaction mixture was agitated on a wrist shaker for 12 h at ambient temperature. The resin was filtered and washed with MeOH containing 1% Et3N (100 mL), CH2Cl2 containing 1% Et3N (100 mL) and Et2O (100 mL) and then dried under high vacuum. The completion of the reaction was verified by TLC analysis after cleavage of the product from the resin with PPTS (ca. 3 equivalents) in MeOH. NMR analysis of the crude product obtained from the cleavage showed a single compound corresponding to the previously reported product 410 (FIG. 19) thereby establishing a yield of >95%. Although exact procedures for the sequence of reactions leading to sarcodictyins A (7) and B (8) are given only for resin 240, similar procedures were followed for resin 230 and with similar results.

Attachment of the urocanic acid side chain and synthesis of resin 270 as illustrated in FIG. 17. A suspension of hydroxy resin 250 (2.0 g, 0.256 mmol, 1.0 equivalent) in DMF (6 mL) was treated with mixed anhydride 260 (0.302 g, 1.28 mmol, 5.0 equivalents) in the presence of Et3N (0.357 mL, 2.56 mmol, 10 equivalents) and 4-DMAP (62 mg, 0.512 mmol, 2.0 equivalents) for 24 h at 50° C. The resin was filtered, washed with CH2Cl2 containing 1% Et3N (2×25 mL), Et2O (25 mL), CH2Cl2 containing 1% Et3N (2×25 mL) and Et2O (3×20 mL) and then dried under high vacuum. The completion of the reaction was confirmed by TLC analysis after cleavage of the product from the resin by the action of PPTS (ca. 3 equivalents) and MeOH (which also revealed the presence of 5–10% of a less polar by-product presumed to be derived from impurities in reagent 260). NMR analysis of the crude product obtained from the cleavage confirmed its identity16 and led to an estimated yield of 90%.

Desilylation and oxidation of alcohol 270. Synthesis of solid-supported aldehyde 280 as illustrated in FIG. 17. A suspension of resin 270 (300 mg, 38.4 mmol, 1.0 equivalent)

in THF (1.5 mL) was treated with TBAF (1.0 M in THF, 384 mmol, 10 equivalents) for 8 h at 25° C. The resin was filtered, washed with THF containing 1% Et3N (4×10 mL) and Et2O (3×10 mL) and then dried under high vacuum. The completion of the reaction was established by TLC analysis after cleavage of the product from a sample of resin by the action of PPTS (ca. 3 equivalents) and MeOH. NMR analysis of the crude product so obtained confirmed its identityll and established a yield of >95% for the deprotection steps. The resin (250 mg, 32 mmol, 1.0 equivalent) was resupended in CH2Cl2 (1.0 mL) containing pyridine (12.8 mg, 160 mmol, 5.0 equivalents) and treated with a preformed suspension of Dess-Martin periodinane (67.2 mg, 160 mmol, 5.0 equivalents), NaHCO3 (40.3 mg, 480 mmol, 15 equivalents) and pyridine (25.6 mg, 64 mmol, 10 equivalents) in CH2Cl2 (1.5 mL). The mixture mixture was allowed to react for 2 h at ambient temperature. The resin was then filtered, washed with CH2Cl2 (4×10 mL), H2O (3×10 mL), MeOH (2×5 mL), CH2Cl2 (2×5 mL), Et2O (3×5 mL) and dried under high vacuum. The completion of the reaction, the identity of the resulting product and the yield of the reaction (>95%) were established by TLC and NMR analysis after subjecting a sample the resin to cleavage with CSA (ca. 3 equivalents) and MeOH.

Oxidation of aldehyde 280 and esterification of the resulting carboxylic acid. Synthesis of polymer-bound sarcodictyins A (290) and B (300) as illustrated in FIG. 17. A mixture of resin 280 (220 mg, 28.2 mmol, 1.0 equivalent), sodium chlorite (63.3 mg, 704 mmol, 25 equivalents), KH2PO4 (83.7 mg, 704 mmol, 25 equivalents) and isobutylene (2 M in THF, 1.40 mmol, 50 equivalents) in THF:tBuOH:H2O (4:4:1) was allowed to react for 48 h at ambient temperature. The resulting resin was filtered, washed with water (3×10 mL), MeOH (2×10 mL), 0.5 M PPTS in CH2Cl2 (3×10 mL), CH2Cl2 (2×10 mL) and Et2O (2×10 mL) and then dried under high vacuum. The completion of the reaction was established by TLC analysis after cleaving the acid products from the resin with CSA (ca. 3 equivalents) in MeOH thereby estimating a yield of >95%. The resin was then split into two portions (100 mg each, 12.8 mmol, 1.0 equivalent) and each were treated with a solution of DMF (0.5 mL) containing DCC (26 mg, 128 mmol, 10 equivalents) and 4-DMAP (7.7 mg, 64 mmol, 5.0 equivalents). To the first portion of resin was added MeOH (4.0 mg, 128 mmol, 10 equivalents) and to the second portion of resin was added EtOH (5.9 mg, 128 mmol, 10 equivalents). The reaction vessels were agitated on a wrist shaker for 48 h after which time each resin was filtered and washed with CH2Cl2 (4×5 mL), MeOH (2×5 mL), CH2Cl2 (3×5 mL), Et2O (3×5 mL). The completion of the reaction was established by TLC after cleaving a sample of each ester product from the solid support by the action of CSA (ca. 3 equivalents) and MeOH thereby estimating a yield of >90%.

Cleavage of polymer-bound sarcodictyins A an B with CSA/H2O. Synthesis of sarcodictyins A (7) and B (8) as illustrated in FIG. 17. A suspension of resin 290 (92 mg, 11.7 mmol, 1.0 equivalent) or 300 (90 mg, 11.5 mmol, 1.0 equivalent) in CH2Cl2/H2O (2:1, 2.0 mL) at 25° C. was treated with CSA (8 mg, 35.1 mmol, 3.0 equivalents) and stirred vigorously over the course of 40 hours. The reaction mixture was then quenched with NaHCO3 (9.8 mg, 117 mmol, 10 equivalents) filtered and the aqueous layer washed with CH2Cl2 (3×1 mL). The combined organic layers were dried over MgSO4, concentrated and the product was purified by PTLC (3% MeOH in CH2Cl2) to yield 3.0 mg of natural sarcodictyin A (7) (ca. 75% yield from 290, ca. 51% overall yield from 240) or 2.6 mg sarcodictyin B (8) (ca. 75% yield from 300, ca. 44% overall yield from 240).

Reaction of resin 250 with trans-cinnamoyl chloride. Towards the synthesis of cinnamoate ester 310 as illustrated in FIG. 18. To a suspension of resin 250 (600 mg, 0.077 mnmol) in DMF (5.0 mL) was added, cinnamoyl chloride (128 mg, 0.77 mmol, 10 equivalents), Et3N (0.215 mL, 1.54 mmol, 20 equivalents) and 4-DMAP (46.5 mg, 0.385 mmol, 5.0 equivalents) and the reaction mixture was heated at 50° C. for 12 hours. The resin was then filtered, washed with CH2Cl2 containing 1% Et3N (5×20 mL and Et2O (2×100 mL) and then dried under high vacuum. The completion of the reaction was established by TLC analysis after cleavage of the ester from the solid support by PPTS (ca. 3 equivalents) in MeOH thereby estimating a yield of >95%.

DCC-mediated esterification of resin 250 with thiazole acid side chain Ar-II. Towards the synthesis of thiazole ester 310 as illustrated in FIG. 18. To a suspension of resin 250 (200 mg, 0.026 mmol) in DMF (3.0 mL) was added thiazole acid side chain Ar-II (scheme 5 and 6) (48 mg, 0.26 mmol, 10 equivalents), DCC (52 mg, 0.26 mmol, 10 equivalents) and 4-DMAP (6.3 mg, 0.052 mmol, 2.0 equivalents) and the reaction mixture was heated at 50° C. for 48 hours. The resin was then filtered, washed with CH2Cl2 containing 1% Et3N (5×20 mL) and Et2O (2×100 mL) and then dried under high vacuum. The completion of the reaction was established by TLC analysis after cleavage of the ester from the solid support by PPTS (ca. 3 equivalents) in MeOH treatment thereby estimating a yield of 90–95%.

Reaction of alcohol 250 with phenyl isocyanate. Towards the synthesis of phenyl carbamate 310 as illustrated in FIG. 18. To a suspension of resin 250 (500 mg, 0.064 mmol, 1.0 equivalent) in DMF (4.0 mL) was added, phenyl isocyanate (77 mg, 0.64 mmol, 10 equivalents) and 4-DMAP (39 mg, 0.32 mmol, 5 equivalents) and the reaction mixture was shaken on a wrist shaker for 10 hours. The resin was filtered, washed with CH2Cl2 containing 1% Et3N (3×15 mL) and Et2O (2×15 mL) and then dried under high vacuum. The completion of the reaction was established by TLC analysis of the product obtained from PPTS (ca. 3 equivalents)/ MeOH cleavage of the substrate from the resin thereby estimating a yield of >95%.

General desilylation procedure. Synthesis of hydroxy resins 310 as illustrated in FIG. 18. A suspension of the silylated resin (1.0 equivalent) in THF was allowed to react with TBAF (10 equivalents, 1.0 M in THF) at 25° C. for 6 hours. The resin was then filtered, washed with THF containing 1% Et3N, CH2Cl2 (containing 1% Et3N) and Et2O and then dried under high vacuum. The completion of the reactions was verified by cleavage of the corresponding alcohol from the resin under the influence of PPTS (ca. 3 equivalents) and MeOH thereby estimating a yield of >95%.

General procedure for the functionalization of hydroxy resins 310. Synthesis of compounds 320 as illustrated in FIG. 18. A suspension of resin 310 (1.0 equivalent) in CH2Cl2 at 25° C. was treated with Et3N (10 equivalents), 4-DMAP (2.0 equivalents) and acetic anhydride (10 equivalents) or benzoyl chloride (10 equivalents) or methyl chloroformate (10 equivalents) or phenylisocyanate (10 equivalents). After 15 hours, the resin was filtered, washed with CH2Cl2 containing 1% Et3N and Et2O and then dried under high vacuum. The reactions were monitored by TLC analysis of the product obtained after PPTS (ca. 3 equivalents)/ MeOH cleavage. The acylation, benzoylation and formation of carbamate were found to proceed smoothly (>95%) whereas the carbonate formation proceeded in 70% yield along with the formation of two less polar unidentified by-products.

General procedure for the Dess-Martin oxidation of solid-supported hydroxy resins 310. Synthesis of aldehyde resins 340 as illustrated in FIG. 18. To a suspension of hydroxy resin 310 (1.0 equivalent) in CH2Cl2 containing pyridine (5.0 equivalents) was added a preformed suspension of Dess-Martin periodinane (5.0 equivalents), NaHCO3 (15 equivalents) and pyridine (10 equivalents) in CH2Cl2. The mixture was allowed to react for 2 h at ambient temperature. The resin was then filtered, washed with CH2Cl2, H2O, MeOH, Et2O and dried under high vacuum. A yield of >95% was estimated by TLC analysis of the cleavage products obtained by treatement of the resin with CSA (ca. 3 equivalents) and MeOH.

General procedure for the sodium chlorite oxidation of aldehyde resins 340. Synthesis of carboxylic acids 350. A mixture of aldehyde resin 340 (1.0 equivalent), sodium chlorite (25 equivalents), KH2PO4 (25 equivalents) and isobutylene (2 M in THF, 50 equivalents) in THF:tBuOH:H2O (4:4:1) was allowed to react for 48 h at ambient temperature. The resulting resin was filtered, washed with water, MeOH, 0.5 M PPTS in CH2Cl2, CH2Cl2, Et2O and dried under high vacuum. The completion of the reaction was verified by TLC analysis after cleaving the acid products from the resin with CSA (ca. 3 equivalents) in MeOH thereby estimating a yield of >95%.

General procedure for the DCC/4-DMAP-mediated formation of ester or amide sarcodictyin analogs 360. To a suspension of resin 350 as illustrated in FIG. 18 (1.0 equivalent) in DMF was added DCC (10 equivalents), 4-DMAP (5.0 equivalents), an alcohol or an amine (10 equivalents, amines were used as HCl or PPTS salts) and the reaction mixture was allowed to react for 20 h at ambient temperature. The resin was then filtered, washed with CH2Cl2, MeOH and Et2O and dried under high vacuum. A yield of >85% was estimated by TLC analysis of the cleavage product obtained by treatement of the resin with CSA (ca. 3 equivalents) and MeOH.

General procedure for the Ph3P/DEAD-mediated formation of ester sarcodictyin analogs 360 as illustrated in FIG. 18. A suspension of resin 350 (1.0 equivalent) in THF containing Ph3P (10 equivalents) and an alcohol (10 equivalents) was cooled to 0° C. DEAD (10 equivalents) was then added dropwise and the reaction mixture was allowed to warm up to 25° C. After 12 hours, the resin was filtered, washed with CH2Cl2 and Et2O and dried under high vacuum. The completion of the reaction was established by TLC analysis after cleaving the esters from the resin with CSA (ca. 3 equivalents) in MeOH thereby estimating a yield of >90%.

General procedure for the formation of azides 380 via a Mitsunobu reaction as illustrated in FIG. 18. A suspension of resin 310 (1.0 equivalent) in THF containing Ph3P (10 equivalents) and (PhO)2P(O)N3 (10 equivalents) was cooled to 0° C. and treated with DEAD (10 equivalents, dropwise addition). After completion of the addition, the reaction mixture was allowed to warm up to 25° C. After 4 hours, the resin was filtered, washed with CH2Cl2 (containing 1% Et3N), Et2O and dried under high vacuum. The completion of the reaction was established by TLC after cleaving the azide product from the solid support by the action of PPTS (ca. 3 equivalents) and MeOH. NMR analysis of the cleavage product revealed >95% yield (see compound 560 for spectroscopic data).

General procedure for the Ph3P/H2O-mediated reduction of azides 380. Toward the syntheses of amides 390 as illustrated in FIG. 18. A suspension of resin 380 (1.0 equivalent) in THF containing Ph3P (10 equivalents) and H2O (50 equivalents) was heated to 50° C. and stirred at that temperature for 8 hours. The resin was then filtered, washed with CH2Cl2 containing 1% Et3N and Et2O and dried under high vacuum. The completion of the reaction was established by TLC analysis after cleaving the amine product from the solid support by the action of PPTS (ca. 3 equivalents) and MeOH thereby estimating a yield of >95%.

General procedure for the synthesis of amides 390 as illustrated in FIG. 18. A suspension of the resin-bound amines (1.0 equivalent) in CH2Cl2 at 25° C. was treated with Et3N (15 equivalents) and acetic anhydride (10 equivalents) or benzoyl chloride (10 equivalents) for 10 h at ambient temperature. The resin was then filtered, washed with CH2Cl2 containing 1% Et3N, Et2O and dried under high vacuum. A yield of >90% was estimated by TLC analysis of the cleavage product obtained by treatement of the resin with PPTS (ca. 3 equivalents) and MeOH.

General procedure for the cleavage with PPTS/ROH. Synthesis of sarcodictyin analogs 330 and 400 as illustrated in FIG. 18. A suspension of resins 320 or 390 (1.0 equivalent) in ROH at 25° C. was treated with PPTS (3.0 equivalents). After 15 hours, the reaction was quenched with solid NaHCO3 (10 equivalents), filtered and washed with CH2Cl2 and MeOH. The combined filtrates were concentrated and the product was purified by PTLC (60–90%, see individual compounds in supplementary material for exact overall yields).

General procedure for the cleavage with CSA/H2O. Synthesis of sarcodictyin analogs 370 as illustrated in FIG. 18. A suspension of resins 290 or 300 (1.0 equivalent) in CH2Cl2/H2O (2:1) at 25° C. was treated with CSA (3.0 equivalents). After 40 hours, the reaction was quenched with solid NaHCO3 (10 equivalents) filtered and washed with CH2Cl2. The organic layer of the combined filtrates was collected, dried over MgSO4, concentrated and the product was purified by PTLC (60–90%, see individual compounds in supplementary material for exact overall yields).

General procedure for the transketalization with CSA/ROH. Synthesis of sarcodictyin analogs 370 as illustrated in FIG. 18. A suspension of resins 360 in ROH (0.5 mL) at 25° C. was treated with CSA (3.0 equivalents). After 15 hours, the resin was quenched with NaHCO3 (10 equivalents) filtered and washed with CH2Cl2 and MeOH. The combined filtrates were concentrated and the products were purified by PTLC (60–90%, see individual compounds in supplementary material for exact overall yields).

Preparation of pyridine carboxylic acid Ar-I as illustrated in FIG. 19: To a solution of 2-pyridinecarboxaldehyde (2.0 g, 18.7 mmol, 1.0 equivalent) in benzene (37 mL) was added Ph3PCHCO2Me (9.36 g, 28.0 mmol, 1.5 equivalents) and the reaction mixture was heated at reflux temperature for 2 hours. After the end of the reaction was established (TLC), the solvent was evaporated under reduced pressure and the crude product was purified by flash column chromatography (silica gel, Et2O-hexanes, 1:1, Rf=0.26) furnishing the expected a,b-unsaturated methyl ester (2.9 g, 95% yield). The so prepared methyl ester (1.5 g, 9.2 mmol, 1.0 equivalent) was treated in THF:H2O (1:1, 30 mL) with LiOH—H2O (1.16 g, 27.6 mmol, 3.0 equivalents) at ambient temperature for 3 h after which time the end of the reaction was established (TLC). The reaction mixture was extracted with sat. aq. NaHCO3 (3×20 mL), the combined aqueous extracts were acidified with 1 M HCl to pH 4 and further extracted with EtOAc (4×20 mL). Concentration of the combined organic solutions furnished, in quantitative yield, essentially pure carboxylic acid Ar-I (1.4 g, 100% yield). Rf=0.35 (silica gel, EtOAc); mp 141–142 ° C.

(EtOAc); FT-IR (neat) nmax 3434, 3091, 1700, 1644, 1595, 1568, 1464, 1319, 1224, 1016, 980 cm$^{-1}$.

Preparation of thiazole carboxylic acid Ar-II as illustrated in FIG. 19: According to the procedure described for the synthesis of pyridine derivative Ar-I, the corresponding thiazole aldehyde (2.0 g, 16 mmol, 1.0 equivalent) was reacted with Ph3PCHCO2Me (8.0 g, 24.0 mmol, 1.5 equivalents) in benzene (32 mL) to yield after chromatographic purification (silica gel, Et2O-hexanes, 3:1), the expected a,b-unsaturated thiazole methyl ester (2.8 g, 97% yield). Rf=0.42 (silica gel, Et2O-hexanes, 3:1); FT-IR (neat) nmax 3095, 3048, 1707, 1631, 1431, 1300, 1275, 1170, 1125, 998 cm$^{-1}$.

The so obtained methyl ester (0.50 g, 2.73 mmol, 1.0 equivalent) was saponified by the action of LiOH—H2O (0.33 g, 8.19 mmol, 3.0 equivalents) in THF:H2O (1:1, 7 mL) as described for pyridine acid Ar-I above, to produce thiazole acid Ar-II (0.46 g, 100% yield) as a white crystaline solid. Rf=0.32 (silica gel, EtOAc); mp 172–173° C. (EtOAc); FT-IR (neat) nmax 3413, 2919, 1690, 1672, 1625, 1496, 1414, 1308, 1273, 1196, 1137 cm$^{-1}$.

Preparation of oxazole carboxylic acid Ar-III as illustrated in FIG. 19: According to the procedure described for the synthesis of pyridine derivative Ar-I above, the corresponding oxazole aldehyde (0.7 g, 6.3 mmol, 1.0 equivalent) was reacted with Ph3PCHCO2Me (3.16 g, 9.45 mmol, 1.5 equivalents) in benzene (13 mL) to yield after chromatographic purification (silica gel, EtOAc), the expected a,b-unsaturated oxazole methyl ester (2.7 g, 96%) yield. Rf=0.61 (silica gel, EtOAc); FT-IR (neat) nmax 3132, 3088, 1716, 1646, 1439, 1388, 1336, 1298, 1209, 1166, 976, 916, 866, 814 cm$^{-1}$.

The so obtained methyl ester (0.3 g, 1.80 mmol, 1.0 equivalent) was saponified by the action of LiOH—H2O (0.22 g, 5.4 mmol, 3.0 equivalents) in THF:H2O (1:1, 15 mL) as described for pyridine carboxylic acid Ar-I, to produce thiazole carboxylic acid Ar-III (0.28 g, 100%) in quantitative yield as a white crystaline solid. Rf=0.33 (silica gel, EtoAc); mp 165–166° C. (EtOAc); FT-IR (neat) nmax 3085, 2938, 2546, 1668, 1636, 1598, 1566, 1429, 1404, 1274, 1219, 1105, 981, 915, 870, 796, 692, 637 cm$^{-1}$.

Attachment of the pyridine side chain and desilylation. Synthesis of compound 420 as illustrated in FIG. 19. To a solution of hydroxy compound 410 (23.0 mg, 0.046 mmol, 1.0 equivalent) in CH2Cl2 (2.2 mL) was added 4-DMAP (2.8 mg, 0.023 mmol, 0.5 equivalents), pyridine carboxylic acid Ar-I (10.2 mg, 0.068 mmol, 1.5 equivalents) and DCC (18.8 mg, 0.091 mmol, 2.0 equivalents) at 25° C. The reaction mixture was stirred for 20 h at that temperature and then concentrated. The crude mixture was purified by flash chromatography (silica gel, EtOAc-hexane, 1:4, Rf=0.28) to furnish the corresponding ester (24.5 mg, 85%). The latter compound was desilylated as follows: A solution of the silylether (24.5 mg, 0.038 mmol, 1.0 equivalent) in THF (1 mL) was treated with TBAF (1.0 M in THF, 77 mL, 2.0 equivalents) and the reaction mixture was stirred for 1 hour at 25° C. The solvent was removed under reduced pressure and the crude product was purified by flash chromatography (silica gel, EtOAc-hexane, 1:1) to yield alcohol 420 (16.1 mg, 87%). Rf=0.10 (silica gel, EtOAc-hexane, 1:1); [α]$_{D25}$ −13.75 (c=0.8, CHCl3); FT-IR (neat) nmax 3410, 2961, 1713, 1647, 1583, 1468, 1434, 1319, 1160, 1034, 986, 786, 752 cm$^{-1}$.

Attachment of the thiazole side chain and desilylation. Synthesis of compound 430 as illustrated in FIG. 19. According to the procedure described above for compound 420, to a solution of hydroxy compound 410 (15 mg, 0.030 mmol, 1.0 equivalent) in CH2Cl2 (1.8 mL) was added 4-DMAP (1.8 mg, 0.015 mmol, 0.5 equivalents), thiazole carboxylic acid Ar-II (6.5 mg, 0.039 mmol, 1.3 equivalents) and DCC (11.3 mg, 0.055 mmol, 1.7 equivalents) at 25° C. to provide, after flash chromatography (silica gel, EtOAc-hexane, 1:4), the corresponding ester (12 mg, 61% yield). Desilylation of the latter compound (6.0 mg, 9.1 mmol, 1.0 equivalent) in THF (1 mL) with TBAF (1.0 M in THF, 18 mL, 2.0 equivalents) furnished after flash chromatography (silica gel, EtOAc-hexane, 1:2) alcohol 430 (5.5 mg, 100%). Rf=0.18 (silica gel, EtOAc-hexane, 1:2); [α]$_{D25}$ +19.6 (c=0.55, CHCl3); FT-IR (neat) nmax 3414, 2961, 1711, 1636, 1450, 1270, 1158, 1038 cm$^{-1}$.

Attachement of the oxazole side chain and desilylation. Synthesis of compound 440 as illustrated in FIG. 19. According to the procedure described for the synthesis of compound 420, alcohol 410 (21 mg, 0.042 mmol, 1.0 equivalent) was treated with 4-DMAP (2.5 mg, 0.020 mmol, 0.5 equivalents), oxazole carboxylic acid Ar-III (8.4 mg, 0.055 mmol, 1.3 equivalents) and DCC (16.9 mg, 0.082 mmol, 2.0 equivalents) in CH2Cl2 (2 mL) to produce, after chromatographic purification (silica gel, EtOAc-hexane, 1:4, Rf=0.43) the desired ester (23 mg, 86%). The latter compound (23 mg, 0.036 mmol, 1.0 equivalent) was deprotected by the action of TBAF (1.0 M in THF, 72 mL, 2.0 equivalents) according to the procedure described above for compound 420 to afford, after chromatographic purification (flash column, silica gel, EtOAc-hexane, 1:1), alcohol 440 (16 mg, 92%). Rf=0.21 (silica gel, EtOAc-hexane, 1:1); [α]$_{D25}$ +8.1 (c=1.6, CHCl3); FT-IR (neat) nmax 3410, 2961, 2865, 1712, 1651, 1451, 1302, 1258, 1160, 1106, 1035, 988 cm$^{-1}$.

Oxidation of alcohol 440. Synthesis of aldehyde 470 as illustrated in FIG. 19. To a solution of alcohol 440 (16 mg, 0.033 mmol, 1.0 equivalent) in CH2Cl2 (2.0 mL) was added NaHCO3 (20 mg, 0.238 mmol, ca. 7 equivalents) and Dess-Martin periodinane (25 mg, 0.060 mmol, ca. 2 equivalents) in CH2Cl2 (1.5 mL) and the reaction mixture was stirred for 50 min at 25° C. after which time isopropanol (excess) was added followed by EtOAc (2.0 mL). The precipitates were filtered off through a short plug of silica and the filtrates were concentrated and purified by flash chromatography (silica gel, EtOAc-hexane, 1:1) to yield the desired aldehyde 470 (13.3 mg, 84%). Rf=0.56 (silica gel, EtOAc-hexane, 1:1); [α]$_{D25}$ +85.0 (c=1.3, CHCl3); FT-IR (neat) nmax 2962, 1697, 1650, 1450, 1301, 1256, 1160, 1107 cm$^{-1}$.

Preparation of sarcodictyin analog 480 as illustrated in FIG. 19: According to the procedure described above for the synthesis of compound 470, alcohol 420 (16.0 mg, 0.033 mmol, 1.0 equivalent) was treated with NaHCO3 (26.6 mg, 0.334 mmol, ca. 10 equivalents) and Dess-Martin periodinane (35.4 mg, 0.083 mmol, ca. 2.5 equivalents) in CH2Cl2 (1.5 mL) to produce, after chromatographic purification (silica gel, EtOAc-hexane, 1:4, Rf=0.35), the corresponding aldehyde (7.0 mg, 44%). The so obtained aldehyde 450 (7.0 mg, 0.015 mmol, 1.0 equivalent) was treated with 2-methyl-2-butene (2.0 M in THF, 1.5 mL), NaH2PO4 (5.3 mg, 0.044 mmol, ca. 3 equivalents) and NaClO2 (8.0 mg, 0.088 mmol, ca. 6 equivalents) in THF:tBuOH:H20 (5:5:1, 2.2 mL) at 0° C. The reaction mixture was stirred at 0° C. for 2 hours after which time a solution of CH2N2 in Et2O (excess) was added and stirring was continued for an additional 10 min at 25° C. The excess CH2N2 was removed by a stream of argon and the reaction mixture was extracted with Et2O (3×8 mL), dried over Na2SO4, and concentrated. The crude residue was purified by flash chromatography (silica gel, EtOAc-hexane, 1:4) to afford sarcodictyin analog 480 (3.2 mg, 43% for 2 steps). Rf=0.56 (silica gel, EtOAc-hexane, 1:1); $[\alpha]_{D25}$ −37.14 (c=0.07, CHCl3).

Preparation of sarcodictyin analog 490 as illustrated in FIG. 19. According to the procedure described above for the synthesis of compound 470, to a solution of alcohol 430 (5.0 mg, 0.010 mmol, 1.0 equivalent) in CH2Cl2 (1.0 mL) was added NaHCO3 (6.7 mg, 0.080 mmol, 8.0 equivalents) and Dess-Martin periodinane (8.5 mg, 0.02 mmol, 2.0 equivalents) and the reaction mixture was stirred for 30 min at 25° C. to afford after flash chromatography (silica gel, EtOAc-hexane, 1:4; Rf=0.45) the corresponding aldehyde 460 (2.0 mg, 40%) which was used directly in the next step. Thus, aldehyde 460 (2.0 mg, 0.004 mmol, 1.0 equivalent) in tBuOH:H2O (5:1, 0.6 mL) was treated with 2-methyl-2-butene (2.0 M in THF, 0.5 mL, 1.0 mmol), NaH2PO4 (1.4 mg, 0.012 mmol, 3.0 equivalents) and NaClO2 (2.2 mg, 0.024 mmol, 6.0 equivalents) at 0° C. The reaction mixture was stirred at 0° C. for 2 hours after which time a solution of CH2N2 (excess) in Et2O was added and stirring was continued for an additional 10 min at 25° C. The excess CH2N2 was removed by a stream of argon and the reaction mixture was extracted with Et2O (3×5 mL), dried over Na2SO4, and concentrated. The crude residue was purified by flash chromatography (silica gel, EtOAc-hexane, 1:4) to yield sarcodictyin analog 490 (1.5 mg, 71% for 2 steps). Rf=0.45 (silica gel, EtOAc-hexane, 1:4); $[\alpha]_{D25}$ −13.4 (c=0.10, CHCl3); FT-IR (neat) nmax 2960, 2360, 2337, 1714, 1636, 1436, 1268, 1157 cm$^{-1}$.

Preparation of sarcodictyin analog 500 as illustrated in FIG. 19. According to the procedure described above for the synthesis of compound 490, aldehyde 470 (8.5 mg, 0.017 mmol, 1.0 equivalent) was treated with 2-methyl-2-butene (2.0 M in THF, 1.0 mL), NaH2PO4 (6.3 mg, 0.053 mmol, ca. 3 equivalents) and NaClO2 (9.6 mg, 0.106 mmol, ca. 6 equivalents) in tBuOH:H2O (5:1, 1.2 mL) to furnish, after diazoethane treatment and chromatographic purification (silica gel, EtOAc-hexane, 1:2), sarcodictyin analog 500 (8.0 mg, 87% for 2 steps). Rf=0.35 (silica gel, EtOAc-hexane, 1:2); $[\alpha]_{D25}$ +3.6 (c=0.8, CHCl3); FT-IR (neat) nmax 2963, 1713, 1650, 1449, 1301, 1250, 1158, 1049 cm$^{-1}$.

Preparation of sarcodictyin analog 520 as illustrated in FIG. 19. A solution of alcohol 410 (2.5 mg, 0.0052 mmol, 1.0 equivalent) in CH2Cl2 (1.0 mL) at −78° C. was treated with DAST [(diethylamino)sulfur trifluoride] (1.3mL, 0.010 mmol, ca. 2 equivalents) and stirred at that temperature for 3 hours. The reaction mixture was quenched by the addition of solid NaHCO3 (30 mg), warmed to 25° C., concentrated and purified by flash chromatography (silica gel, EtOAc:CH2Cl2:MeOH, 10:10:1) to afford the desired sarcodictyin analog 520 (2.5 mg, 99% yield). Rf=0.31 (silica gel, EtOAc:CH2Cl2:MeOH, 10:10:1); $[\alpha]_{D25}$ −32.4 (c=0.25, CHCl3); FT-IR (neat) nmax 2961, 1762, 1637, 1451, 1384, 1269, 1156, 1037, 980 cm$^{-1}$.

Preparation of sarcodictyin analog 530 as illustrated in FIG. 19. To a solution of alcohol 410 (5.0 mg, 0.01 mmol, 1.0 equivalent) in CH2Cl2 (1.0 mL) there was added acetic anhydride (5.0 mg, 0.052 mmol, 5.2 equivalents), Et3N (10 mL, 0.07 mmol, 6.8 equivalents) and 4-DMAP (2.0 mg, 0.016 mmol, 1.6 equivalents) and the reaction mixture was stirred at ambient temperature for 2 hours. After completion of the reaction was established (TLC), quenching with saturated NaHCO3 solution (2×2 mL), removal of the solvents under reduced pressure and flash chromatographic purification (silica gel, EtOAc) afforded sarcodictyin analog 530 in quantitative yield (5.2 mg, 100%). Rf=0.41 (silica gel, EtOAc); $[\alpha]_{D25}$ −16.2 (c=0.55, CHCl3); FT-IR (neat) nmax 2961, 1737, 1704, 1638, 1450, 1381, 1233, 1155, 1039 cm$^{-1}$.

Preparation of sarcodictyin analog 540 as illustrated in FIG. 19. To a stirring solution of ketal 530 (5.2 mg, 0.01 mmol, 1.0 equivalent) in CH2Cl2:H2O (10:1) at ambient temperature there was added a catalytic amount of CSA (10% mol) and stirring was continued for 72 hours. After completion of the reaction was established by TLC (40 h), quenching with solid NaHCO3, filtration and chromatographic purification (silica gel, EtOAc), sarcodictyin analog 540 was obtained (5.1 mg, 95% yield). Rf=0.37 (silica gel, EtOAc); $[\alpha]_{D25}$ −28.9 (c=0.35, CHCl3); FT-IR (neat) nmax 3348, 2962, 1737, 1704, 1638, 1233, 1155 cm$^{-1}$.

Synthesis of Phenylthioglycoside 1200 as illustrated in FIG. 23. To a solution of NaH (60% in mineral oil, 0.408 g, 10.2 mmol, 1.2 equivalents) in DMF (20 mL) at 0° C. was added a solution of 1100 (2.55 g, 8.67 mmol, 1.0 equivalent; Nicolaou et al. *Tetrahedron* 1997, 53, 8751–8778; Lindle, T. *Angew. Chem. Int. Ed.* 1998, 110, 806–808) in DMF (30.0 mL), and the reaction mixture was stirred for 30 min at 0° C., after which PMB-Cl (1.6 mL, 11.0 mmol, 1.1 equivalents) was added. The reaction was then stirred at room temperature for 2 h and quenched by addition of saturated NH4Cl (10 mL), extracted with ether (3×50 mL), dried over MgSO4 and concentrated. The crude product was purified by flash chromatography (silica gel, 20% EtOAC in hexanes) to afford acetonide 1200 (3.26 g, 93%). Rf=0.64 (silica, EtOAc-hexane,1:2); $[\alpha]_D$ +40.4 (c 1.0, CHCl3); FT-IR (neat) nmax 2986, 2934, 1612, 1514, 1379, 1243, 1074, 833, 745 cm$^{-1}$.

Synthesis of Phenylthioglycoside Diol 1300 as illustrated in FIG. 23. To a solution of acetonide 1200 (3.26 g, 8.11 mmol, 1.0 equivalent) in MeOH (100 mL) was added ethylene glycol (10 mL). The solution was then chilled to 0° C., TsOH.H2O (150 mg, 0.80 mmol, 0.1 equivalents) was added and the reaction was warmed to 25° C. and stirred for 5 hours. After the reaction was complete (TLC analysis), Et3N (1.0 mL) was added followed by saturated NaHCO3 solution (30.0 mL). The reaction mixture was then extracted with ethyl acetate (3×200 mL), and the combined organic extracts were washed with brine and dried over Na2SO4. After concentration, the product was purified by flash chromatography (silica gel, EtOAc in hexanes, 3:2) to afford diol 1300 (2.47 g, 84%). Rf=0.54 (silica gel, EtOAc-hexane, 2:1); $[\alpha]_D$ −25.9 (c 1.0, CHCl3); FT-IR (neat) nmax 3369, 2908, 1613, 1514, 1249, 1079, 822 cm$^{-1}$.

Synthesis of Phenylthioglycoside bis-TBS Ether 1400 as illustrated in FIG. 23. To a solution of diol 1300 (1.26 g, 3.48 mmol, 1.0 equivalent) in CH2Cl2 (25 mL) at 0° C. was added Et3N (4.7 mL, 33.5 mmol, 9.6 equivalents) followed by TBS-OTf (3.1 mL, 13.5 mmol, 3.9 equivalents), and the reaction mixture was stirred at the same temperature for 2 hours. After complete (TLC analysis), the reaction was quenced by addition of water (5 mL) and extracted with CH2Cl2 (2×50 mL). The combined extracts were washed with brine, dried over Na2SO4 and concentrated. The crude residue was purified by flash chromatography (silica gel, Et2O in hexanes, 1:30) to afford silyl ether 1400 (2.00 g, 97%). Rf=0.60 (silica gel, EtOAc-hexane, 1:5); $[\alpha]_D$ −40.42 (c 1.0, CHCl3); FT-IR (neat) nmax 2930, 2856, 1612, 1514, 1472, 1253, 1109, 840 cm$^{-1}$.

Synthesis of Bis-TBS ether Acetal 1500 as illustrated in FIG. 23. To a solution of 1400 (1.66 g, 2.81mmol) in wet acetone (93% acetone, 7% water) (40 mL) at 0° C. was added N-bromosuccinimide (3.3 equivalents, 1.65 g, 9.27 mmol) followed by pyridine (11 equivalents, 30.9 mmol, 2.5 mL). The resulting solution was stirred for 4 h at 0° C. and quenched by addition of saturated Na2SO3 solution. The reaction mixture was extracted with ether (3×5 mL), and the organic extracts were washed with brine and dried over Na2SO4 before concentrating. The crude residue was purified by flash chromatography (silica gel, 10% EtOAC in hexanes) to afford 1500 (1.12 g, 80% as a ca. 2:1 mixture of the two anomers). Rf=0.37, 0.46 (silica gel, Et2O-hexane, 1:1); FT-IR (neat) 3456, 2930, 2857, 1513, 1469, 1253, 1096, 1034, 836 cm$^{-1}$.

Synthesis of Trichloroacetimidate 900 as illustrated in FIG. 23. To a solution of the anomeric mixture 1500 (0.218 g, 437 mmol) and CCl3CN (0.220 mL, 2.20 mmol, 5.0 equivalents) in CH'2Cl2 (5.0 mL) at 0° C. was added NaH (0.002 g, 41.7 mmol, 0.1 equivalents) and the reaction mixture was stirred at room temperature for 3.5 h (TLC analysis), after which it was concentrated and the residue was purified by flash chromatography (silica gel, 33% EtOAc in hexanes with 2% Et3N) to produce 900 (0.261 g, 93%). Rf=0.76 (silica gel, Et2O-hexane,1:3); [α]$_D$ −69.7 (c 1.0, CHCl3); FT-IR (neat) nmax 3348, 2930, 2857, 1670, 1514, 1252, 1113, 1006, 837 cm$^{-1}$.

Synthesis of enynone 1600 as illustrated in FIG. 24. A solution of LiHDMS (1.0 M in THF, 0.150 mL, 0.150 mmol, 2.0 equivalents) was added dropwise to a solution of 35 (77.5 mg, 0.0742 mmol, 1.0 equivalent) in THF (4.0 mL) at −30° C. and the reaction was stirred for 10 min at −30° C. After the reaction was complete as indicated by TLC analysis, saturated NH4Cl solution (5 mL) was added and the resulting bi-phasic mixture was extracted with ether (3×30 mL). The combined extracts were washed with brine, dried over over Na2SO4, and concentrated to give a crude residue which was was purified by short column chromatography (silica gel, 10% EtOAc in hexanes). The purified mixture of isomers was then used immediately for the next step. To a solution of this mixture in CH2Cl2 (4.0 mL) at 0+ C. was added NaHCO3 (62.3 mg, 0.742 mmol, 10.0 equivalents) and pyridine (60 mL, 0.742 mmol, 10.0 equivalents), and the resulting solution was chilled to 0° C. and stirred for 10 min. Dess Martin reagent (63.0 mg, 0.149 mmol, 2.0 equivalents) was added, and the reaction was stirred for an additional 15 min at 0° C. After the reaction was complete as indicated by TLC analysis, it was quenched by addition of saturated Na2S2O3 (2 mL). The mixture was extracted with CH2Cl2 (3×30 mL), and the combined extracts were dried over Na2SO4 and concentrated to provide a crude residue which was purified by flash chromatography (silica gel, 5% EtOAc in hexanes) to afford 1600 (72.0 mg, 93% for two steps). Rf=0.80 (silica, Et2O-hexane, 1:3); [α]$_D$ −11.5 (c 0.46, CHCl3); FT-IR (neat) nmax 2954, 2878, 1663, 1512, 1462, 1250, 1115, 1037, 1004, 834, 777, 741 cm$^{-1}$.

Synthesis of enynone alcohol 1700 as illustrated in FIG. 23. To a solution of PMB-ether 1600 (202 mg, 0.194 mmol, 1.0 equivalent) in CH2Cl2 (7.0 mL) and water (0.35 mL) at 0° C. was added DDQ (98.0 mg, 0.432 mmol, 2.3 equivalents) and the resulting solution was allowed to warm to 25° C. and stirred for 20 min. Once complete by TLC analysis, the reaction was quenched by addition of saturated Na2S2O3 solution (2.0 mL) and saturated NaHCO3 solution (2.0 mL). The reaction mixture was then extracted with CH2Cl2 (3×40 mL) and the combined extractes were dried over Na2SO4 and concentrated to afford a crude residue which was purified by flash chromatography (silica gel, 10% EtOAc in hexanes) to provide alcohol 1700 (163 mg, 91%). Rf=0.6 (silica gel, EtOAc-hexane, 1:5); [α]$_D$ −0.176 (c 1.6, CHCl3); FT-IR (neat) nmax 2955, 2929, 2203, 1663, 1462, 1366, 1252, 1214, 1118, 1076, 1004, 835, 740 cm$^{-1}$.

Synthesis of enynone Acetate 1800 as illustrated in FIG. 24. To a solution of alcohol 1700 (163 mg, 0.177 mmol, 1.0 equivalent) in CH2Cl2 (5.0 mL) at 0° C. was added Et3N (400 ml, 2.86 mmol, 16.1 equivalents), 4-DMAP (10.0 mg, 0.0818 mmol, 0.46 equivalents), and Ac2O (0.2 mL, 2.12 mmol, 12.0 equivalents) and the reaction was warmed to 25° C. and stirred for 1 hour. After completion was established by TLC analysis, the reaction was quenced by addition of saturated NaHCO3 solution (2.0 mL). The reaction mixture was then extracted with CH2Cl2 (3×40 mL) and the combined extracts were dried over Na2SO4 and concentrated to give a crude residue which was purified by flash chromatography (silica gel, 10% EtOAc in hexanes) to afford acetate 1800 (162 mg, 95%). Rf=0.57 (silica, Et2O-hexane, 1:5); [α]$_D$ −0.34 (c 1.4, CHCl3); FT-IR (neat) nmax 2956, 1746, 1661, 1461, 1371, 1237, 1119, 1004 cm$^{-1}$.

Synthesis of enynone diol 1900 as illustrated in FIG. 24. To a solution of silyl ether 1800 (161 mg, 0.167 mmol, 1.0 equivalent) in THF (4.2 mL) at 0° C. was added Et3N.3HF (0.60 mL, 3.68 mmol, 22.0 equivalents), and the reaction mixture was warmed to 25° C. and stirred for 4 hours. After completion (TLC analysis), the reaction was quenched by addition of saturated NaHCO3 solution (2.0 mL) at 0° C. The bi-phasic mixture was then extracted with ether (3×40 mL) and the combined extractes were washed with brine, dried over Na2SO4 and concentrated to produce a crude residue which was purified by flash chromatography (silica gel, 50% EtOAc in hexanes) to afford diol 1900 (100 mg, 81%). Rf=0.40 (silica gel, Et2O-hexane, 3:1); [α]$_D$ −53.5 (c 0.85, CHCl3); FT-IR (neat) nmax 3410, 2929, 2856, 1744, 1652, 1370, 1254, 1123, 1063, 1037, 837, 777 cm$^{-1}$.

Synthesis of tricyclic Core Compound 2200 as illustrated in FIG. 24. A heterogeneous mixture of eneynone 1900 (103 mg, 0.140 mmol, 1.0 equivalent) and Lindlar catalyst (148 mg, 0.069 mmol, 0.5 equivalents) was treated with hydrogen (1 atm), and the reaction was stirred at 25° C. for 20 min. The reaction mixture was then filtered through a celite pad eluting with ether and concentrated to give a crude residue which was used without further purification. This residue was dissolved in MeOH (4.0 mL), PPTS (7.0 mg, 0.028 mmol, 0.2 equivalents) was added and the reaction was stirred at 25° C. for 20 min. Once complete (TLC monitoring), the reaction was quenced by addition of saturated NaHCO3 solution (2.0 mL). The reaction mixture was then extracted with ether (3×20 mL) and the combined extractes were washed with brine, dried over Na2SO4 and concentrated to provide a crude residue which was purified by flash chromatography (silica gel, 50% EtOAc in hexanes) to afford methylketal 2200 (80.1 mg, 76%) Rf=0.74 (silica gel, Et2O-hexane, 3:1); [α]$_D$ −38.61 (c 0.65, CHCl3); FT-IR (neat) nmax 3448, 2929, 2856, 1748, 1254, 1144, 1038, 837, 775 cm$^{-1}$.

Eleutherobin bis-TBS Ether 2300 as illustrated in FIG. 24. To a solution of alcohol 2200 (64 mg, 0.0871 mmol, 1.0 equivalent) in CH2Cl2 (0.4 mL) was added Et3N (0.177 mL, 1.27 mmol, 15.0 equivalents) and 4-DMAP (21 mg, 0.0017 mmol, 0.02 equivalents). The solution was then chilled to 0° C. and a 0.2 M CH2Cl2 solution of mixed anhydride 2400 was added (4.2 mL, 0.84 mmol, 9.6 equivalents; as above in example 2). The reaction mixture was then warmed to 25° C. and stirred for 18 hours. After completion was established (TLC analysis), the reaction was quenced by addition of saturated NaHCO3 solution and extracted with CH2Cl2 (3×20 mL). The combined organic extracts were dried over Na2SO4 and concentrated to afford a crude residue which was purified by flash chromatography (silica gel, 67% EtOAc in hexanes) to produce urocanic ester 2300 (73.0 mg, 97%). Rf=0.35 (silica gel, EtOAc-hexane, 1:3); $[\alpha]_D$ −61.3 (c 0.6, CHCl3); FT-IR (neat) nmax 2929, 2856, 2362, 2338, 1746, 1707, 1639, 1468, 1367, 1296, 1253, 1150, 1062, 1038, 1001, 886, 837, 775 cm$^{-1}$.

Synthesis of eleutherobin (4) as illustrated in FIG. 24. To a solution of disilyl ether 2300 (15.5 mg, 0.017 mmol, 1.0 equivalent) in THF (4.0 mL) at 0° C. was added AcOH (1.0 M in THF, 0.070 mL, 0.070 mmol, 4.1 equivalents) and TBAF (1.0 M in THF, 0.30 mL, 0.30 mmol, 17.6 equivalents). The reaction mixture was warmed to 25° C. and stirred for 2.5 hours, after which water (1.0 mL) and saturated NaHCO3 solution (1.0 mL) were added and the mixture was extracted with CH2Cl2 (3×20 mL). The combined extracts were dried over Na2SO4 and concentrated to provide a crude residue which was purified by flash chromatography (silica gel, 2% MEOH in CH2Cl2 with 1% Et3N) to afford eleutherobin 4 (11.0 mg, 96%) Rf=0.22 (silica gel, MeOH— CH2Cl2, 1:20); $[\alpha]_D$ −67 (c 0.15, MEOH); FT-IR (neat) nmax 3388, 2933, 2851, 1735, 1708, 1637, 1367, 1247, 1162, 1039, 998 cm$^{-1}$.

Synthesis of β-Glycoside 2500 as illustrated in FIG. 25. A solution of alcohol 7000 (20.0 mg, 0.0355 mmol, 1.0 equivalent) and imidate 9000 (62.1 mg, 0.0966 mmol, 2.7 equivalents) in 2:1 dioxane:toluene (6.0 mL) was chilled to 0° C., TMSOTf (0.05 M in ether, 40 ml, 0.002 mmol, 0.05 equivalents) was added and the reaction was stirred at 0° C. for 10 min after which Et3N (20 ml) was added followed by NaHCO3 (3 mL). The reaction mixture was then extracted with ether (3×20 mL), and the combined extractes were washed with brine and dried over Na2SO4 and concentrated to give a crude residue which was purified by flash chromatography (silica gel, 3% EtOAc in hexanes) to afford 2500 (27.9 mg, 75%). Rf=0.56 (silica gel, EtOAc-hexane, 1:5); $[\alpha]_D$ −27.7 (c 1.0, CHCl3); FT-IR (neat) nmax 2954, 1676, 1612, 1512, 1461, 1364, 1250, 1114, 1038, 835, 740 cm$^{-1}$.

Synthesis of α-Anomer of Eleutherobin (2700) as illustrated in FIG. 25. The α-anomer of eleutherobin was constructed by following the same reaction sequence depicted in FIG. 24 from compound 2600. Rf=0.1 (silica gel, MeOH—CH2Cl2, 1:20).

Bis-Acetoxy Eleutherobin (2800) and Methyl-Ketal Precursors of Eleuthosides A and B (2900+3000) as illustrated in FIG. 27. To a solution of natural eleutherobin (4) (10.0 mg, 0.015 mmol, 1.0 equivalent), Et3N (6.0 mL, 0.043 mmol, 3.0 equivalents), and 4-DMAP (0.40 mg, 0.0033 mmol, 0.2 equivalents) in CH2Cl2 (0.60 mL) at 0° C. was added Ac2O (1.0 M in CH2Cl2, 0.017 mL, 0.017 mmol, 1.1 equivalents) and the reaction was stirred at the same temperature for 1 hour. The reaction mixture was then quenched by addition of saturated NaHCO3 solution (0.50 mL) and extracted with CH2Cl2 (5×20 mL). The combined organic extracts were dried over Na2SO4 and concentrated to provide a crude residue which was was purified by flash chromatography (silica gel, 2% MeOH in CH2Cl2) to afford triacetate 2800 (1.8 mg, 16%) along with an inseperable mixture of eleuthosides 2900 and 3000 (7.8 mg, 73%) as well as recovered 1 (0.5 mg, 5%). 2800. Rf=0.44 (silica gel, MeOH— CH'2Cl2,1:20); $[\alpha]_D$ −67.3 (c 1.2, CHCl3); FT-IR (neat) nmax 2962, 1746, 1740, 1644, 1634, 1372, 1226, 1156, 1068, 759, 668, 617 cm$^{-1}$.

Synthesis of eleuthosides A and B (5+6) as illustrated in FIG. 27. To a solution of 2700 and 2800 mixture (7.8 mg, 0.011 mmol, 1.0 equivalent) in CH'2Cl2 (2.0 mL) and H2O (0.20 mL) at 25° C. was added CSA (5.2 mg, 0.022 mmol, 2.0 equivalents) and the reaction was stirred at the same temperature for 48 hours. Once complete (TLC monitoring), the reaction was quenched by addition of saturated NaHCO3 solution (0.50 mL) and extracted with CH2Cl2 (5×20 mL). The combined organic extracts were dried over Na2SO4 and concentrated to provide a crude residue which was purified by flash chromatography (silica gel, 3% MeOH in CH2Cl2) to afford an inseparable mixture of eleuthoside A (5) and B (6) (5.3 mg, 80%). Data for mixture of 5 and 6. Mixture of 5 and 6 Rf=0.32 (silica, MeOH—CH2Cl2, 1:20); FT-IR (neat) nmax 3734, 3628, 2962, 2928, 2866, 1734, 1700, 1684, 1652, 1646, 1636, 1558, 1456, 1374, 1252, 1160, 1065, 1037, 986, 884, 874 cm$^{-1}$.

Synthesis of regioisomeric Eleutherobin (3100) and Deaceto-Eleutherobin (3200). To a solution of disilyl ether 2300 (5.4 mg, 6.1 mmol) in THF (350 mL) was added TBAF (1.0 M in THF, 20 mL, 20 mmol, 3.3 equivalents) and the reaction mixture was stirred for 6 h at ambient temperature. After completion (TLC analysis), the crude residue was immediately purified by column chromatography (gradually increasing the eluting solvent from 2E10% MeOH in CH2Cl2) to afford eleutherobin 4 (22%), migration product 3100 (60%) and triol 3200 (8%). 3100. Rf=0.28 (silica, x2, MeOH— CH'2Cl2, 1:20); FT-IR (neat) nmax 3355, 2964, 2925, 1704, 1638, 1260, 1070, 800 cm$^{-1}$.

Selected Data for key compounds as shown in FIGS. 20–21

Compound 550. Isolated yield after preparative TLC purification 2.8 mg (79% overall from 24). Rf=0.68 (silica gel, EtOAc); $[\alpha]_{D25}$ −21.5 (c=0.20, CHCl3); Rf=0.15 (silica gel, EtOAc-hexane, 1:3); FT-IR (neat) max 2961, 1711, 1637, 1451, 1271, 1154, 1068, 1037, 980, 715 cm$^{-1}$.

Compound 560. Isolated yield after preparative TLC purification 2.4 mg (64% overall from 24). Rf=0.56 (silica gel, EtOAc-hexane, 4:1); $[\alpha]_{D25}$ −43.8 (c=0.5, CHCl3); FT-IR (neat) max 2962, 2104, 1703, 1639, 1450, 1270, 1156 cm$^{-1}$.

Compound 570. Isolated yield after preparative TLC purification 1.5 mg (41% overall from 24). Rf=0.52 (silica gel, EtOAc); FT-IR (neat) max 3333, 2961, 1709, 1639, 1543, 1445, 1315, 1220, 1160, 1048 cm$^{-1}$.

Compound 580. Isolated yield after preparative TLC purification 3.9 mg (71% overall from 24). Rf=0.32 (silica gel, 3% MeOH in CH2Cl2).

Compound 590. Isolated yield after preparative TLC purification 2.2 mg (59% overall from 24).

Compound 620. Isolated yield after preparative TLC purification 2.3 mg (64% overall from 24). Rf=0.41 (silica gel, EtOAc).

Compound 630. Isolated yield after preparative TLC purification 0.7 mg (20% overall from 24). Rf=0.42 (silica gel, EtOAc).

Compound 640. Isolated yield after preparative TLC purification 1.9 mg (55% overall from 24). Rf=0.43 (silica gel, EtOAc).

Compound 650. Isolated yield after preparative TLC purification 0.5 mg (14% overall from 24). Rf=0.43 (silica gel, EtOAc).

Compound 660. Isolated yield after preparative TLC purification 1.8 mg (46% overall from 24). Rf=0.43 (silica gel, EtOAc).

Compound 670. Isolated yield after preparative TLC purification 2.0 mg (58% overall from 24). Rf=0.40 (silica gel, EtOAc).

Compound 680. Isolated yield after preparative TLC purification 2.0 mg (61% overall from 24). Rf=0.44 (silica gel, EtOAc).

Compound 690. Isolated yield after preparative TLC purification 2.1 mg (54% overall from 24). Rf=0.43 (silica gel, EtOAc).

Compound 700. Isolated yield after preparative TLC purification 2.3 mg (69% overall from 24). Rf=0.40 (silica gel, EtOAc).

Compound 710. Isolated yield after preparative TLC purification 0.7 mg (42% overall from 24). Rf=0.62 (silica gel, EtOAc).

Compound 730. Isolated yield after preparative TLC purification 2.0 mg (61% overall from 24). Rf=0.39 (silica gel, EtOAc).

Compound 740. Isolated yield after preparative TLC purification 1.9 mg (56% overall from 24). Rf=0.38 (silica gel, 3% MeOH in CH2Cl2).

Compound 750. Isolated yield after preparative TLC purification 1.6 mg (55% overall from 24). Rf=0.40 (silica gel, EtOAc).

Compound 760. Isolated yield after preparative TLC purification 2.9 mg (62% overall from 24). Rf=0.40 (silica gel, EtOAc).

Compound 770. Isolated yield after preparative TLC purification 1.1 mg (56% overall from 24). Rf=0.51 (silica gel, EtOAc).

Compound 790. Isolated yield after preparative TLC purification 1.3 mg (33% overall from 24). Rf=0.40 (silica gel, EtOAc).

Compound 800. Isolated yield after preparative TLC purification 1.0 mg (26% overall from 24). Rf=0.38 (silica gel, EtOAc).

Compound 810. Isolated yield after preparative TLC purification 1.3 mg (34% overall from 24). Rf=0.43 (silica gel, EtOAc).

Compound 820. Isolated yield after preparative TLC purification 1.1 mg (28% overall from 24). Rf=0.45 (silica gel, EtOAc).

Compound 830. Isolated yield after preparative TLC purification 1.1 mg (28% overall from 24). Rf=0.43 (silica gel, EtOAc).

Compound 840. Isolated yield after preparative TLC purification 1.2 mg (32% overall from 24). Rf=0.39 (silica gel, EtOAc).

Compound 850. Isolated yield after preparative TLC purification 2.2 mg (69% overall from 24) Rf=0.32 (silica gel, 3% MeOH in CH2Cl2); $[\alpha]_{D25}$ −1.9 (c=0.21, EtOH); FT-IR (neat) max 2960, 1712, 1637, 1435, 1385, 1299, 1269, 1245, 1155, 1050 cm$^{-1}$.

Compound 860. Isolated yield after preparative TLC purification 2.0 mg (50% overall from 24). Rf=0.43 (silica gel, EtOAc).

Compound 870. Isolated yield after preparative TLC purification 0.8 mg (46% overall from 24). Rf=0.74 (silica gel, EtOAc).

Compound 880. Isolated yield after preparative TLC purification 2.1 mg (54% overall from 24). Rf=0.42 (silica gel, EtOAc).

Compound 890. Isolated yield after preparative TLC purification 1.8 mg (45% overall from 24). Rf=0.43 (silica gel, EtOAc).

Compound 900. Isolated yield after preparative TLC purification 1.3 mg (32% overall from 24). Rf=0.40 (silica gel, EtOAc).

Compound 910. Isolated yield after preparative TLC purification 1.0 mg (25% overall from 24). Rf=0.42 (silica gel, EtOAc).

Compound 920. Isolated yield after preparative TLC purification 1.7 mg (40% overall from 24). Rf=0.38 (silica gel, EtOAc)

Compound 930. Isolated yield after preparative TLC purification 1.0 mg (23% overall from 24). Rf=0.41 (silica gel, EtOAc).

Compound 940. Isolated yield after preparative TLC purification 0.5 mg (17% overall from 24). Rf=0.74 (silica gel, EtOAc-hexanes, 1:3).

Compound 950. Isolated yield after preparative TLC purification 0.5 mg (20% overall from 24). Rf=0.11 (silica gel, EtOAc-hexanes, 1:3).

Compound 960. Isolated yield after preparative TLC purification 1.7 mg (62% overall from 24). Rf=0.46 (silica gel, EtOAc-hexanes, 1:3).

Compound 970.Isolated yield after preparative TLC purification 2.2 mg (68% overall from 24). Rf=0.31 (silica gel, EtOAc-hexanes, 1:1).

Compound 980. Isolated yield after preparative TLC purification 1.6 mg (51% overall from 24). Rf=0.28 (silica gel, EtOAc-hexanes, 1:2); Rf=0.31 (silica gel, EtOAc-hexanes, 1:3).

Compound 990: Isolated yield after preparative TLC purification 2.2 mg (68% overall from 24). Rf=0.50 (silica gel, EtOAc-hexanes, 1:3).

Compound 1000. Isolated yield after preparative TLC purification 1.5 mg (40% overall from 24). Rf=0.38 (silica gel, EtOAc-hexanes, 1:3).

Compound 1010. Isolated yield after preparative TLC purification 0.7 mg (28% overall from 24). Rf=0.52 (silica gel, EtOAc-hexanes, 1:1).

Compound 1020. Isolated yield after preparative TLC purification 0.5 mg (20% overall from 24). Rf=0.32 (silica gel, EtOAc-hexanes, 1:1).

Compound 1030. Isolated yield after preparative TLC purification 1.5 mg (42% overall from 24). Rf=0.35 (silica gel, EtoAc-hexanes, 1:1).

Compound 1040. Isolated yield after preparative TLC purification 0.5 mg (17% overall from 24). Rf=0.51 (silica gel, EtOAc-hexanes, 1:1).

Compound 1050. Isolated yield after preparative TLC purification 1.9 mg (60% overall from 24). Rf=0.31 (silica gel, EtOAc-hexanes, 1:1).

Compound 1060. Isolated yield after preparative TLC purification 2.2 mg (57% overall from 24). Rf=0.31 (silica gel, EtOAc-hexanes, 1:1).

Compound 1070. Isolated yield after preparative TLC purification 1.8 mg (68% overall from 24). Rf=0.39 (silica gel, EtOAc-hexanes, 1:4); $[\alpha]_D$ 25 −2.1 (c=0.10, CHCl3); FT-IR (neat) max 2960, 1739, 1719, 1436, 1370, 1236, 1049 cm$^{-1}$.

Compound 1080. Isolated yield after preparative TLC purification 2.6 mg (79% overall from 24). Rf=0.28 (silica gel, EtOAc-hexanes 1:4).

Compound 1090. Isolated yield after preparative TLC purification 1.7 mg (61% overall from 24). Rf=0.44 (silica gel, EtOAc-hexanes, 1:4).

Data for -Anomer of 1600; +38.0 (c 0.40, CHCl3); FT-IR (neat) max 2955, 2879, 2205, 1736, 1653, 1613, 1513, 1461, 1366, 1250, 1094, 1037, 1004, 835, 777, 740 cm$^{-1}$.

Data for -Anomer of 1700: $[\alpha]_D$ +36.6 (c 0.80, CHCl3); FT-IR (neat) max 3471, 2955, 2879, 2206, 1653, 1600, 1461, 1255, 1159, 1114, 1091, 1027, 1004, 834, 777, 740 cm$^{-1}$.

Data for -Anomer of 1800: $[\alpha]_D$ +56.7 (c 0.76, CHCl3); FT-IR (neat) max 2956, 2878, 2206, 1757, 1659, 1465, 1368, 1231, 1116, 1004, 836, 778, 740 cm$^{-1}$.

Data for -Anomer of 1900: $[\alpha]_d$ +42.8 (c 0.46, CHCl3); FT-IR (neat) max 3440, 2957, 2930, 2856, 2205, 1739, 1652, 1468, 1368, 1254, 1230, 1168, 1091, 1057, 1037, 836, 778 cm$^{-1}$.

Data for -Anomer of 2200; [α]$_D$ +47.1 (c 0.95, CHCl3); FT-IR (neat) max 3472, 2957, 2930, 2856, 1747, 1469, 1366, 1254, 1233, 1096, 1056, 1038, 837, 777 cm$^{-1}$.

Data for -Anomer of 23: [α]$_D$ +23.1 (c 1.1, CHCl3); FT-IR (neat) max 2956, 2929, 2856, 1748, 1705, 1639, 1439, 1468, 1367, 1253, 1154, 1095, 1037, 836, 776 cm$^{-1}$.

2111: A solution of 3 N NaOH (0.15 equivalents) was slowly added to a solution of S-(+)-Carvone (1.0 equivalent, 0.7 M) in MeOH at 0° C., and 35% hydrogen peroxide solution (1.3 equivalents) was added dropwise over 3 hours. The reaction mixture was quenched by addition of saturated Na$_2$SO$_3$ solution and extracted with CH$_2$Cl$_2$. The extracts were dried over Na$_2$SO$_4$ and concentrated to afford the epoxide (92%).

3111: A solution of 2111 (1.0 equivalent, 1.3 M) and PtO$_2$ (0.5%) in was treated with H$_2$ at room temperature for 6 hours. The reaction mixture was then filtered throuh a celite pad and concentrated. The crude product was purified by flash chromotagraphy (silica, 5% EtOAc in hexane) to afford 3111 (95%).

4111: A solution of LDA was generated by addition of 1.6 M BuLi in hexanes (1.1 equivalents) to a solution of diisopropyl amine (1.2 equivalents) in THF at −78° C. The solution was then warmed to 0° C. and stirred for 30 min afterwhich a solution of 3111 (1.0 equivalent, 1.0 M) in THF was added dropwise via cannula at −78° C. over 1.5 hours. The resulting solution was then stirred for 30 min. A solution of formaldehyde was prepared by cracking paraformaldehyde (10.0 equivalents) at 140° C. and bubbling the resulting gas through THF at −78° C. over 45 min. This formadehye solution was then added to the enolate solution via cannula over 1 hour at −78° C. The reaction was quenched by addition of saturated NH$_4$Cl solution, allowed to warm to room temperature, and extracted with ether. The extracts were dried over Na$_2$SO$_4$ and concentrated. The crude product was purified by flash chromatography (silica, 10% EtOAc in hexane) to afford 4111 (63%).

5111: To a solution of 4111 (1.0 equivalent, 0.25 M), triethylamine (6.0 equivalents), and DMAP (0.05 equivalents) in CH$_2$Cl$_2$ at 0° C. was added t-butyldimethylsilyl chloride (3.0 equivalents). The reaction mixture was stirred at room temperature for 12 h and quenched via addition of water. The organic layer was seperated, dried over Na$_2$SO$_4$ and concentrated. The crude product was purified by flash chromatography (silica, 3% EtOAc in hexane) to afford 5111 (84%).

6111: To a solution of 5111 (1.0 equivalent, 0.2 M) in THF at −78° C. was added 1.0 M L-Selectride in THF (1.2 equivalents) via cannula over 1.5 hours. The reaction mixture was stirred an additional 30 min and quenched by addition of saturated NH$_4$Cl solution and allowed to warm to 0° C. Excess 35% hydrogen peroxide solution was then added and the mixture was stirred at 0° C. for 1 hour. The reaction mixture was extracted with EtOAc, and the extrats were dried over Na$_2$SO$_4$ and concentrated. The crude product was purified by flash chromatography (silica, 5% EtOAc in hexane) to afford 6111 (100%).

7111: To a solution of 6111 (1.0 equivalent, 0.4 M) and triethyl amine (2.5 equivalents) in CH$_2$Cl$_2$ at 0° C. was added methanesulfonyl chloride (1.2 equivalents) dropwise over 1 hour. The reaction mixture was stirred at 0° C. for 2 hours, quenched by addition of brine, and extracted with EtOAc. The combined extracts were dried over Na$_2$SO$_4$ and concentrated. The crude product was purified by flash chromotagraphy (silica, 10% EtOAc in hexane) to afford 7111 (91%).

8111: A 0.4 M solution of NaC$_{10}$H$_8$ was prepared by addition of Na metal (5.0 equivalents) to napthalene (5.0 equivalents) in THF and allowing the mixture to stir for 2 hours. A solution of 7111 (1.0 equivalent, 0.2 M) in THF was then added dropwise via cannula at 0° C. The reaction mixture was stirred for 30 min and quenched by addition of saturated NH$_4$Cl solution. the reaction was then poured into brine and extracted with EtOAc. The extracts were dried over Na$_2$SO$_4$ and concentrated. The crude product was purified by flash chromatography (silica, 10% EtO$_2$ in hexane followed by 10% EtOAc in hexane) to afford 8111 (96%).

9111: A solution of 8111 (1.0 equivalent, 0.1 M), triethyl orthoacetate (40.0 equivalents), and propionic acid (0.1 equivalents) was heated at 170° C. for 4 days. The excess triethylorthoacetate was removed by vacuum distillation, and the residue which remained was purified by flash chromotography (silica, 3% EtOAc in hexane) to give the ester 9111 (74%).

10111: A 1.0 M CH$_2$Cl$_2$ solution of diisobutylaluminumnum hydride (1.0 equivalent) was gradually added to a solution of ethyl ester 9111 (1.0 equivalent, 0.2 M) in CH$_2$Cl$_2$ at −78° C., and the reaction mixture was stirred for 30 min. The reaction mixture was quenched by addition of saturated NH$_4$Cl solution and stirred for 2 h at room temperature. The organic layer was separated, dried over Na$_2$SO$_4$, and concentrated. The residue was purified by flash chromatography (silica, 5% EtOAc in hexane) to give the aldehyde 10111 (92%).

11111. To a solution of ethyl vinyl ether (1.0 equivalent, 0.4 M) in THF at −78° C. was added 1.7 M tert-BuLi in hexanes (1.8 equivalents), and the solution was warmed to 0° C. as it changed from yellow to colorless. The solution was then cooled to −78° C. and a solution of 10111 (1.0 equivalent) in THF was added dropwise afterwhich the reaction mixture was stiired for an additional 30 min at −78° C. The reaction was quenched by addition of saturated NH$_4$Cl solution and extracted with ether. The extracts were dried over MgSO$_4$ and concentrated. The crude product was then dissolved up in ether and treated with concentrated H$_2$SO$_4$ while shaking vigorously. The ether solution was washed with water and saturated NaHCO$_3$ solution, dried over MgSO$_4$, and concentrated. The residue was purified by flash chromatography (silica, 10% to 15% Et$_2$O in hexane) to give 11111 (98%).

12111. To a solution of 11111 (1.0 equivalent, 0.1 M) in THF at −78° C. was added 0.5 M ethynyl magnesium bromide (4.5 equivalents) and the reaction mixture was stirred at −78° C. for 12 h while slowly warming to −10° C. The reaction mixture was quenched by addition of saturated NH$_4$Cl solution and extracted with ether. The extracts were dried over MgSo$_4$ and concentrated, and the residue was purified by flash chromatography (silica, 10% to 25% Et$_2$O in hexane) the desired 12111 (56%).

13111. To a solution of 12111 (1.0 equivalent, 0.1 M) in THF at 0° C. was added 1 M TBAF (2.0 equivalents) and the reaction mixture was allowed to warm to 25° C. The reaction was quenched by addition of saturated NH$_4$Cl and extracted with ether. The extracts were concentrated and the residue was purified by filtration through silica gel to give 13111 (100%).

14111. To a solution of 13111 (1.0 equivalent, 0.1 M) in CH$_2$Cl$_2$ was added 2,6-lutidine (6.0 equivalents) and the solution was chilled to 0° C. A portion of trialklylsilyltriflate (3.0 equivalents) was then added and the reaction mixture was allowed to warm to 25° C. The reaction was quenched by addition of saturated NH$_4$Cl and extracted with CH$_2$Cl$_2$. The extracts were dried over MgSO$_4$ and concentrated. The residue was purified by filtration through silica (25% Et$_2$O in hexane) to give 14111 (100%).

15111. To a solution of 14111 (1.0 equivalent, 0.1 M) in MeOH was added a catalytic amount of PPTS (0.1 equivalents). The reaction was worked up by addition of saturated NaHCO$_3$ and extracted with ether. The extracts were dried over MgSO$_4$ and concentrated. The residue was purified by filtration through silica gel to give 15111 (98%).

16111. To a solution of alcohol 15111 (1.0 equivalent, 0.1 M) and activated 4 Å molecular sieves in CH$_2$Cl$_2$ was added NMO (1.5 equivalents) and the reaction mixture was stirred for 10 min. TPAP (0.05 equivalents) was then added to the reaction mixture, and it was stirred at room temperature. The reaction mixture was then flitered through silica gel and washed with CH$_2$Cl$_2$. After concentration aldehyde 15111 (98%) was obtained.

17111. A solution of aldehyde 16111 (1.0 equivalent, 0.2 M), ethyl cyano acetate (40.0 equivalents), and α-alanine (4.0 equivalents) in EtOH was stirred at 50° C. for 72 hours. The reaction mixture was then concentrated and purified by filtration through silica gel (10% Et$_2$O in hexanes) to give 17111 (95%).

18111. To a solution of cyanoester 17111 (1.0 equivalent, 0.6 M) in hexanes at −78° C. was added 1 M DIBAL in toluene (10.0 equivalents). The reaction mixture was stirred for 6 hours at −78° C. and then slowly warmed to −10° C. for 2 hours. The reaction mixture was then diluted with ethyl acetate, quenched by addition of saturated NH$_4$Cl solution, and extracted with ethyl aceate. The extracts were concentrated and purified by flash chromatography (silica, 10% Et$_2$O in hexanes) to give 18111 (67%).

19111: To a solution of alcohol 18111 (1.0 equivalent, 0.2 M) in CH$_2$Cl$_2$ was added base (3.0 equivalents), and trialkylsilylchloride (3.0 equivalents) and the resulting solution was stirred at 25° C. The reaction was quenched by addition of aqueous saturated ammonium chloride solution and concentrated. The residue was purified by flash chromatography (silica, 2% EtOAc in hexane) to give TIPS ether 19111.

20111: A 1.0 M THF solution of lithium bis (trimethylsilyl)amide (1.5 equivalents) was added dropwise to a solution of aldehyde 19111 (1.0 equivalent, 0.1 M) in THF at 25° C. After 10 min the reaction mixture was quenched by the addition of aqueous saturated ammonium chloride solution, extracted with ether, dried over Na$_2$SO$_4$, and concentrated.

21111: Compound 20111 was dissolved in CH$_2$Cl$_2$ and NaHCO$_3$ was added to the solution at 0° C. After 10 min Dess-Martin periodinate was added to the reaction mixture at the same temperature, and the the reaction mixture was then warmed to 25° C. After 4 h the reaction mixture was diluted with ether and a queous saturated sodium bicarbonate solution was added to the mixture, and then sodium thiosulfate pentahydrate was added. The resulting solution was extracted with ether, and the extracts were dried over Na$_2$SO$_4$ and concentrated. The crude products was purified via flash chromotography (silica, 1% EtOAc in hexane) to give the protected alcohol of 21111 (85%).

22111: To a solution of 21111 in THF at 25° C. was added Et$_3$N.3HF (5:1, THF/reagent giving 0.1 M). After stirring the reaction mixture was concentrated and purified by flash chromotagraphy.

23111: To a small flask was added Lindlar's catalyst (0.5 equivalents) under argon. A solution of 22111 (1.0 equivalent) in toluene was then added to the the catalyst, and the reaction mixture was trreated with with H$_2$ at room temperature. After 20 min the reaction mixture was filtered through celite and concentrated to 23111.

24111: To a solution of 23111 (1.0 equivalent) in MeOH was added PPTS (1 equivalent). The reaction mixture was then concentrated and the residue was purified by flash chromatography (silica, 50% Et$_2$O in hexanes with 1% Et$_3$N) to give 24111 (77%).

32111: Compound 28111 (1.0 equivalent) was dissolved in CH$_2$Cl$_2$ and NaHCO$_3$ (10 equivalents) was added to the solution at 0° C. After 10 min Dess-Martin periodinane (2.5 equivalents) was added to the reaction mixture at the same temperature, and the the reaction mixture was then warmed to 25° C. After 1 hour the reaction mixture was diluted with ether and aqueous saturated sodium bicarbonate solution was added to the mixture, and then sodium thiosulfate pentahydrate was added. The resulting solution was extracted with ether, and the extracts were dried over Na$_2$SO$_4$ and concentrated. The crude products was purified via flash chromatography (silica, 10/10/1=EtOAc/CH$_2$Cl$_2$/MeOH) to give the aldehyde 32111 (100%)

33111: To a solution of 32111 (1.0 equivalent) and 2-methyl-2-butene 2.0 M in THF, 70 equivalents) in t-BuOH/H$_2$O (5/1) was added NaH$_2$PO$_4$ (3.0 equivalents) and NaClO$_2$ (6.0 equivalents) at 0° C. The reaction mixture was stirred for 2 hours, then to it was added the solution of CH$_2$N$_2$ (excess) in ether. It was concentrated and the residue was purified by flash chromatography chromatography (silica, 10/10/1=EtOAc/CH$_2$Cl$_2$/MeOH) to give the ester 34111 (71%).

34111: To a solution of 41111 (1.0 equivalent, 0.3 M) in was added Piv-Cl (2.0 equivalents) and triethylamine (2.0 equivalents). The reaction was stirred overnight at room temperature. The solution was then filtered through celite, concentrated, and dissolved in CH$_2$Cl$_2$ to produce a 0.2 M stock solution.

77111: To a solution of NaH (1.2 equivalents, 0.51M) in DMF was added 76111 (1.0 equivalent, 0.30 M) in DMF at 0° C. and the reaction mixture was stirred at 0° C. for eo min afterwhich PMBCl (1.3 equivalents) was added. The reaction was then stirred at room temperature for 2 h and then quenched by addition of saturated NH$_4$Cl, extracted with ether, dried over MgSO$_4$, and concentrated. The crude product was purified by flash chromatography (silica, 20% EtOAC in hexanes) to give 77111 (93%).

78111: To a solution 77111 (1.0 equivalent, 0.07 M) in MeOH and ethyleneglycol (MeOH:ethyleneglycol=10:1) was added CSA (0.1 equivalents) at room temperature and stirred at room temperature for 2 h and then quenched by addition of saturated NaHCO$_3$, extracted with ethyl acetate, dried over MgSO$_4$, and concentrated. The crude product was purified by flash chromatography (silica, 60% EtOAC in hexanes) to give 78111 (84%).

79111: To a solution of 78111 (1.0 equivalent, 0.14 M) and triethylamine (10.0 equivalents) in CH$_2$Cl$_2$ at 0° C. was added TBDMSOTf (4 equivalents) and the reaction was stirred at 0° C. for 2 h and then quenched by addition of saturated NaHCO$_3$, extracted with ethyl acetate, dried over MgSO$_4$, and concentrated. The crude product was purified by flash chromatography (silica, 3% Et$_2$O and 1% triethylamine in hexanes) to give 79111 (93%).

80111: To a solution of 79111 (1.0 equivalent, 0.07 M) in wet acetone (93% acetone, 7% water) at 0° C. was added N-bromosuccinamide (3.3 equivalents) and pyridine (11.0 equivalents). The resulting solution was stirred for 4 h at 0° C. and quenched by addition of saturated Na$_2$SO$_3$ solution. The reaction mixture was extracted with ether, and the extracts were washed with brine and dried over Na$_2$SO$_4$ before concentrating. The crude residue was product was purified by flash chromatography (silica, 10% EtOAC in hexanes) to give 80111 (80%).

81111: To a solution of 80111 (1.0 equivalent, 0.09 M) and CCl$_3$CN (5.0 equivalents) in CH$_2$Cl$_2$ at 0° C. was added NaH (0.1 equivalents) and the reaction was stirred at room temperature for 3.5 h afterwhich it was concentrated and the residue was purified by flash chromatography (silica, 33% EtOAc in hexanes with 2% Et$_3$N) to give 81111 (93%).

87111: Synthesised from 82111 as 81111 from 76111.

89111: To a solution of alcohol 88111 (1.0 equivalent, 0.1 M) in DMF was added imidazole (6.0 equivalents) and TBDMSCl (2.4 equivalents). The reaction mixture was then stirred at room temperature, quenched, concentrated, and purified by flash chromatography.

90111: To a solution of alcohol 89111 (1.0 equivalent, 0.1 M) in CH$_2$Cl$_2$ was added triethylamine (3.0 equivalents), 4-DMAP (0.3 equivalents), and anhydride (e.g. Ac$_2$O) (2.0 equivalents). The reaction mixture was then stirred at room temperature, quenched, concentrated, and purified by flash chromatography.

91111: To a solution of 90111 (1.0 equivalent, 0.1 M) in wet acetone (93% acetone, 7% water) at 0° C. was added N-bromosuccinamide (3.3 equivalents) and pyridine (11.0 equivalents). The resulting solution was stirred at room temperature, quenched, concentrated, and purified by flash chromatography.

92111: To a solution of 91111 (1.0 equivalent, 0.1 M) and CCl$_3$CN (5.0 equivalents) in CH$_2$Cl$_2$ at 0° C. was added NaH (0.1 equivalents). The reaction mixture was then stirred at room temperature, concentrated, and purified by flash chromatography.

94111: To a solution of alcohol 93111 (1.0 equivalent, 0.1 M) in DMF was added imidazole (6.0 equivalents) and TBDMSCl (2.4 equivalents). The reaction mixture was then stirred at room temperature, quenched, concentrated, and purified by flash chromatography.

95111: To a solution of NaH (1.2 equivalents, 0.5 M) in THF was added 94111 (1.0 equivalent, 0.3 M) in THF at 0° C. and the reaction mixture was stirred at 0° C. for eo min afterwhich PMBCl (1.3 equivalents) was added. The reaction mixture was then stirred at room temperature, quenched, concentrated, and purified by flash chromatography.

96111: To a solution of alcohol 95111 (1.0 equivalent, 0.1 M) in DMSO was added potassium t-butoxide (0.3 equivalents). The reaction mixture was then stirred at room temperature, quenched, concentrated, and purified by flash chromatography to give C-1 vinyl ether. To a solution of the resulting vinyl ether (1.0 equivalent, 0.1 M) in THF and water (THF:water=20:1) was added HgCl$_2$ (0.3 equivalents). The reaction mixture was then stirred at 70° C., quenched, concentrated, and purified by flash chromatography.

97111: To a solution of 96111 (1.0 equivalent, 0.1 M) and CCl$_3$CN (5.0 equivalents) in CH$_2$Cl$_2$ at 0° C. was added NaH (0.1 equivalents). The reaction mixture was then stirred at room temperature, concentrated, and purified by flash chromatography.

PROCEDURE A: To a solution of alcohol (e.g. 24111) (1.0 equivalent) in CH$_2$Cl$_2$ was added DCC (1.8 equivalents), 4-DMAP (0.5 equivalents), and side chain containing the carboxylic acid functionality (1.5 equivalents). The reaction mixture was then stirred at room temperature, quenched, concentrated, and purified by flash chromatography.

PROCEDURE B: To a solution of alcohol (e.g. 24111) (1.0 equivalent) in CH$_2$Cl$_2$ was added triethylamine (10.0 equivalents), 4-DMAP (2.0 equivalents), and the mixed anhydride of the side chain (5.0 equivalents). The reaction mixture was then stirred at room temperature, quenched, concentrated, and purified by flash chromatography.

PROCEDURE C: To a solution of ether (e.g. 27111) (1.0 equivalent) in THF (0.1 M) was added TBAF (4.0 equivalents). The reaction mixture was then stirred at room temperature for 2 hours, quenched with H$_2$O, extacted with CH$_2$Cl$_2$, concentrated, and purified by flash chromatography.

PROCEDURE D: A solution of 27111 (1.0 equivalent) in THF:EtOH (20:1, 0.1 M) was added to liquid NH$_3$ (0.05 M) followed by addition of Na metal (10 equivalents) and the reaction was stirred for 20 min at −78° C. The reaction mixture was then quenched with solid NH$_4$Cl, diluted with ether, filtered and concentrated, and purified by flash chromatography.

PROCEDURE E: To a solution of 27111 (1.0 equivalent) in CH$_2$Cl$_2$:water (18:1, 0.01 M) was added DDQ (2.0 equivalents) and the reaction was stirred at room temperature for 30 min. The reaction mixture was then quenched with saturated NaHCO$_3$ solution, extructed with CH$_2$Cl$_2$, dried over sodium surfate, filtered, concentrated and purified by flash chromatography.

PROCEDURE F: To a solution of 28111 (1.0 equivalent, 0.1 M) in THF at 25° C. was added 3,4-dihydro-2H-pyran (10.0 equivalents) and CSA (1.0 equivalent). The reaction mixture was stirred at room temperature, quenched, concentrated, and purified by flash chromatography.

PROCEDURE G: To a solution of alcohol 28111 (1.0 equivalent, 0.01 M) in CH$_2$Cl$_2$ was added triethylamine (3.0 equivalents), 4-DMAP (0.3 equivalents), and anhydride (e.g. Ac$_2$O) (2.0 equivalents). The reaction mixture was then stirred at room temperature, quenched, concentrated, and purified by flash chromatography.

PROCEDURE H: To a solution of 28111 (1.0 equivalent, 0.1 M) in CH$_2$Cl$_2$ was added triethylamine (3.0 equivalents) and chloride (e.g. BzCl) (2.0 equivalents). The reaction mixture was stirred at room temperature, quenched, concentrated, and purified by flash chromatography.

PROCEDURE I: To a solution of 28111 (1.0 equivalent, 0.1 M) in DMF at 0° C. was added NaH (1.3 equivalents) and the reaction mixture was stirred for 30 min. To this mixture was added iodide (e.g. MeI) at 0° C. and resulting mixture was stirred at room temperature, quenched, concentrated, and purified by flash chromatography.

Procedure J: To a solution of acid 33111 (1.0 equivalent) in THF (0.1 M) was added the solution of CH$_2$N$_2$ (excess) in ether. The reaction was monitored by TLC. After disapearance of the starting material the reaction mixture was concentrated and the residue was purified by flash chromatography (silica, 10/10/1=EtOAc/CH$_2$Cl$_2$/MeOH) to give the ester 34111 in high yield.

Procedure K: To a solution of acid 33111 (1.0 equivalent) in CH$_2$Cl$_2$ (0.1 M) was added alcohol R$^5$OH (2.0 equivalents), DMAP (0.5 equivalents) and DCC (1.5 equivalents). The reaction was monitored by TLC. After disapearance of the starting material the reaction mixture was concentrated washed with water, extructed with CH$_2$Cl$_2$, concentrated and the residue was purified by flash chromatography to give the ester 34111 in high yield.

Procedure L: To a solution of 26111 (1.0 equivalent) in CHCl$_3$ (0.1M) at ambient temperature was added alcohol R$^6$OH (2.0 equivalents) followed by a catalytic amount of CSA (0.1 equivalents) and the progress of the reaction was monitored by TLC. After the reaction was completed saturated NaHCO$_3$ was added and the organic layer was extracted with ether, dried with Na$_2$SO$_4$, concentrated and purified by flash chromatography to produce acetal 36111 in high yield.

Procedure M: To a solution of 26111 (1.0 equivalent) in Et$_2$O (0.1M) at −20° C. was added BF3.Et$_2$O (1.0 equivalent) followed by thiol R⁶SH (1.2 equivalents) and the progress of the reaction was monitored by TLC. After the reaction was completed saturated NaHCO₃ was added and the organic layer was extracted with ether, dried with Na₂SO₄, concentrated and purified by flash chromatography to produce thio-acetal 36111 in high yield.

Procedure N: To a solution of alcohol 28111 (1.0 equivalent) in CH₂Cl₂ (0.1M) at 0° C. was added DAST (1.2 equivalents) and the solution was allowed to warm to room temperature. The progress of the reaction was monitored by TLC. After the reaction was completed saturated NaHCO₃ was added and the organic layer was extracted with ether, dried with Na₂SO₄, concentrated and purified by flash chromatography to produce fluorinated compound 37111 in high yield.

Procedure O: To a solution of 28111 (1.0 equivalent, 0.4 M) and triethyl amine (2.5 equivalents) in CH₂Cl₂ at 0° C. was added methanesulfonyl chloride (1.2 equivalents) dropwise over 1 hour. The reaction mixture was stirred at 0° C. for 2 hours, quenched by addition of brine, and extracted with EtOAc. The combined extracts were dried over Na₂SO₄ and concentrated. The crude product was purified by flash chromotagraphy (silica, 10% EtOAc in hexane) to afford the corespondind mesylate (91%). To a solution of the mesylate (1.0 equivalent) in DMF (0.1M) at ambient temperature was added predried CsF (1.2 equivalents) and the solution was warmed to 50° C. The progress of the reaction was monitored by TLC. After the reaction was completed saturated NaHCO₃ was added and the organic layer was extracted with ether, dried with Na₂SO₄, concentrated and purified by flash chromatography to produce fluorinated compound 37111 in high yield.

Procedure P: To a solution of ester (1.0 equivalent, 0.4 M)) in THF/Water (3:4) was added NaOH (1.1 equivalents), and the reaction mixture was stirred at room temperature for 12 hours. The solution was then concentrated down and dried under high vacuum for 12 h to give the acid salt.

Procedure Q: To a solution of alhedyde (1.0 equivalent, 0.2 M) in benzene was added Ph₃P=CHCO₂Me (1.5 equivalents) and the reaction mixture was heated to 80° C. Upon completetion the reaction mixture was concentrated and the residue was purified by flash chromatography.

Procedure R: To a solution of ester (1.0 equivalent, 0.2 M) in CH₂Cl₂ at −78° C. was added 1.0 M DIBAL in CH₂Cl₂ (1.0 equivalent). The reaction was quenched by addition of saturated NH₄Cl solution, extracted with ether, concentrated, and purified by flash chromatography.

What is claimed is:

1. A compound represented by the following structure:

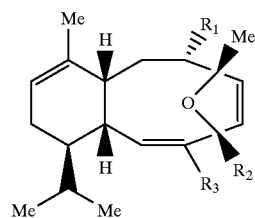

wherein:

R₁ is a radical selected from the group consisting of —OH, OAc, and radicals represented by the following structures:

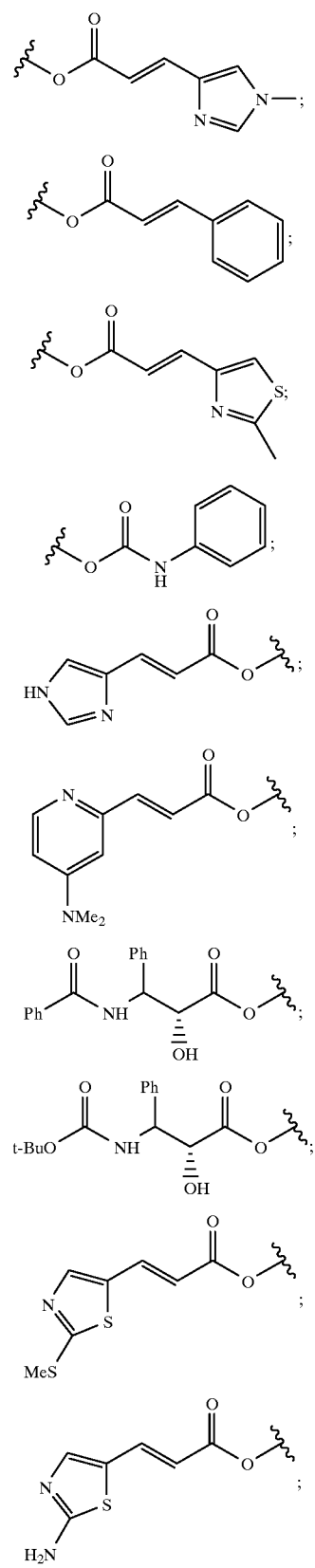

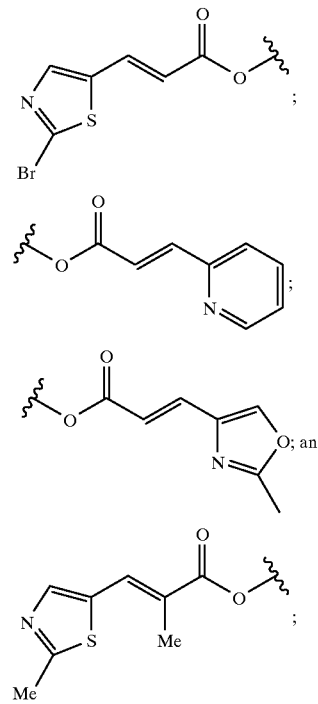

R₂ is a radical selected from the group consisting of —OH, —O(C₁–C₆ alkyl), —OCH₂CF₃, —O-isopropyl, —O-tert-butyl, —O-benzyl, —OCH₂CH=CH₂, —OCH₂CCH, —O(CH₂)₂—OH, —NHMe, —NMe₂, —NHEt, —NEt₂, —NH-n-propyl, —N-(propyl)₂, —NH-iso-propyl, —N-butyl₂, —NH-benzyl, —N-benzyl₂, —SH, —SMe, —SEt, —S-n-propyl, —S-iso-propyl, —S-n-butyl, —S-benzyl, and —S-phenyl;

R₃ is a radical selected from the group consisting of —CH₂OC(O)CH₃, —CH₂OC(O)-phenyl, —CH₂OC(O)O—CH₃, —CH₂OC(O)NH-phenyl, —CH₂—OH, —CH(O), —CH₂—O-tri-isopropylsilyl, —CH₂O—Ac, —CH₂—F, —CH₂N₃, —CH₂NAc, —CH₂NBz, —C(O)—CH₂CF₃, —C(O)—CH₂CH=CH₂, —C(O)—O—CH₂CH₂Cl, —C(O)O(CH₂)₂CH₂Cl, —C(O)O(CH₂)₂CH(CH₃)₂, —C(O)CH₂Ph, —C(O)CH₂-phenyl-OMe, —CH₂—O-tetrahydropyran, —CH₂—O—C(O)CHCl₂, —CH₂—O—C(O)—CCl₃, —CH₂—O—C(O)CHBr₂, —CH₂—O—C(O)—CF₃, —CH₂—O—C(O)CHPh₂, EtC(O)—O—CH₂—, CH₂=CHC(O)—O—CH₂—, HC≡CC(O)—O—CH₂—, n-propyl-C(O)—O—CH₂—, i-PrC(O)—O—CH₂—, cyclopropyl-C(O)—O—CH₂—, n-BuC(O)—O—CH₂—, i-BuC(O)—O—CH₂—, t-BuC(O)—O—CH₂—, cyclo-C₆H₁₁C(O)—O—CH₂—, phenyl-O—CH₂—, 2-furyl—C(O)—O—CH₂—, PhCH=CHC(O)—O—CH₂13, 2-thiophene-C(O)—O—CH₂—, (C₁-C₆ alkyl)-O—CH₂—, i-propyl-O—CH₂—, allyl-O—CH₂—, benzyl-O—CH₂—, AcOCH₂CH₂—O—CH₂—, —COOH, —COO—(C₁-C₆ alkyl), —COO-i-propyl, —COO-t-butyl, —COO-benzyl, —COOCH₂CH=CH₂, —COO-CH₂C≡CH, —COO-cyclo-C₆H₁₁, —CONHBn, —CONH(C₁-C₆ alkyl), —CONH-propyl, —COO—C₈H₁₇,

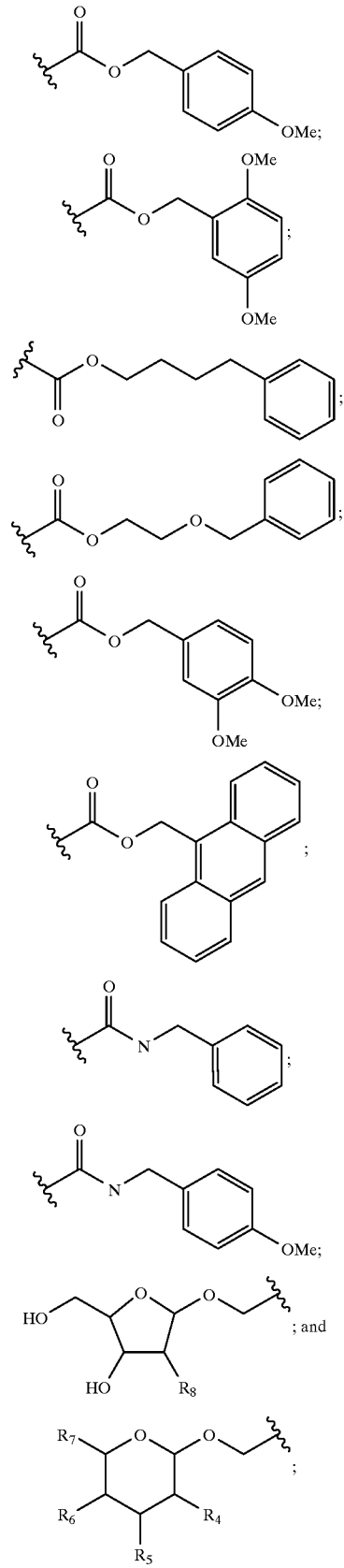

wherein

R₄ is a radical selected from the group consisting of —OH, —OAc, 2-Cl—AcO—, CCl₃C(O)O—, 2-Br—AcO—, CF₃C(O)O—, 2-phenyl-AcO—, ($C_1$-$C_6$ alkyl)-C(O)O—, CH₂=CHC(O)O—, HC≡—CC(O)O—, i-propyl-C(O)O—, cyclo-propyl-C(O)O—, i-butyl-C(O)O—, t-butyl-C(O)O—, cyclo-C₆H₁₁C(O)O—, phenyl-O—, 2-furyl—C(O)O—, PhCH=CHC(O)O—, and 2-thiophene-C(O)O—;

R₅ is a radical selected from the group consisting of —OAc and —OH;

R₆ is a radical selected from the group consisting of —OAc and —OH;

R⁷ is a radical selected from the group consisting of —H, and -methyl;

R₈ is a radical selected from the group consisting of —OAc, 2-Cl—AcO—, CCl₃C(O)O—, 2-Br—AcO—, CF₃C(O)O—, 2-phenyl-AcO—, ($C_1$-$C_6$ alkyl)-C(O)O—, CH₂=CHC(O)O—, HC≡CC(O)O—, i-propyl-C(O)O—, cyclo-propyl-C(O)O—, i-butyl-C(O)O—, t-butyl-C(O)O—, cyclo-C₆H₁₁C(O)O—, phenyl-O—, 2-furyl-C(O)O—, PhCH=CHC(O)O—, and 2-thiophene-C(O)O—, and the following provisos pertain:

a. if R₁ is

[structure]

and R₂ is —OH, then R₃ cannot be simultaneously —CO₂-methyl or —CO₂-ethyl;

b. if R₁ is

[structure]

and R₂ is —O-methyl, then R₃ cannot be

[structure]

wherein R₄ is —OAc, R₅ is hydroxy, R₆ is hydroxy, and R₇ is hydrogen;

c. if R₁ is

[structure]

and R₂ is —OH, then R₃ cannot be

[structure]

wherein R₄ is —OAc, R₅ is hydroxy, R₆ is —OAc, and R₇ is hydrogen; and d. if R₁ is

[structure]

and R₂ is —OH, then R₃ cannot be

[structure]

wherein R₄ and R₅ are —OAc, R₆ is —OH, and R₇ is hydrogen.

2. A compound as described in claim 1 wherein:

R₁ is

[structure]

;

R₂ is a radical selected from the group consisting of —O—Me, —O—Et, and —O—CH₂CF₃; and R₃ is is a radical selected from the group consisting of —C(O)—O—Me, —C(O)—O—Et, —C(O)—O-n-propyl, —C(O)—O—CH₂CH=CH₂, —C(O)—O—(CH₂)₂CH₂Cl, and —C(O)—NH-benzyl.

3. A first advanced intermediate represented by the following structure:

[structure]

wherein:

R₁ is a radical selected from the group consisting of —O-paramethoxybenzyl, —O-triethylsilyl, and radicals represented by the following structures:

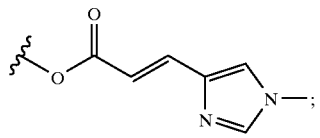

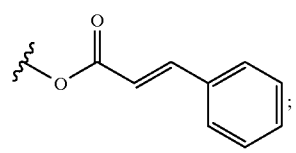

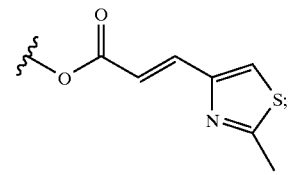

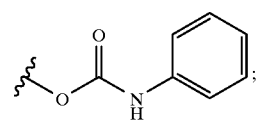

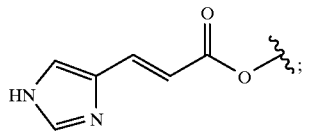

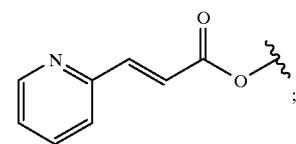

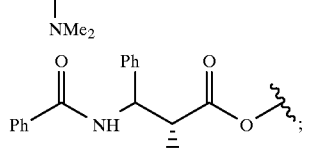

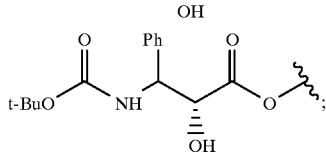

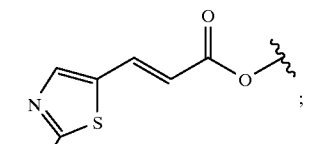

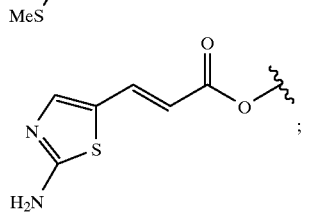

-continued

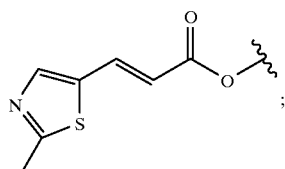

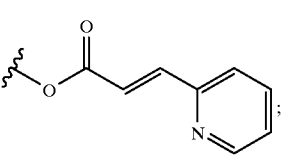

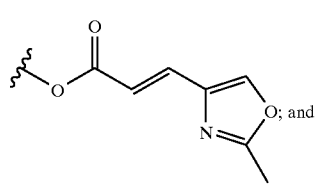

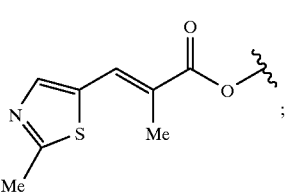

R₃ is a radical selected from the group consisting of —CH₂OC(O)CH₃, —CH₂OC(O)-phenyl, —CH₂OC(O)O—CH₃, —CH₂OC(O)NH-phenyl, —CH₂—OH, —CH(O), —CH₂—O-tri-isopropylsilyl, —CH₂O—Ac, —CH₂—F, —CH₂N₃, —CH₂NAc, —CH₂NBz, —C(O)—CH₂CF₃, —C(O)—CH₂CH=CH₂, —C(O)—O—CH₂CH₂Cl, —C(O)O(CH₂)₂CH₂Cl, —C(O)O(CH₂)₂CH(CH₃)₂, —C(O)CH₂Ph, —C(O)CH₂-phenyl-OMe, —CH₂—O-tetrahydropyran, —CH₂—O—C(O)CHCl₂, —CH₂—O—C(O)—CCl₃, —CH₂—O—C(O)CHBr₂, —CH₂—O—C(O)—CF₃, —CH₂—O—C(O)CHPh₂, EtC(O)—O—CH₂—, CH₂=CHC(O)—O—CH₂—, HC≡CC(O)—O—CH₂—, n-propyl-C(O)—O—CH₂—, i-PrC(O)—O—CH₂—, cyclopropyl-C(O)—O—CH₂—, n-BuC(O)—O—CH₂—, i-BuC(O)—O—CH₂—, t-BuC(O)—O—CH₂—, cyclo-C₆H₁₁C(O)—O—CH₂—, phenyl-O—CH₂—, 2-furyl-C(O)—O—CH₂—, PhCH=CHC(O)—O—CH₂—, 2-thiophene-C(O)—O—CH₂—, (C₁-C₆ alkyl)-O—CH₂—, i-propyl-O—CH₂—, allyl-O—CH₂—, benzyl-O—CH₂—, AcOCH₂CH₂—O—CH₂—, —COOH, —COO—(C₁-C₆ alkyl), —COO-i-propyl, —COO-t-butyl, —COO-benzyl, —COOCH₂CH=CH₂, —COO—CH₂C≡CH, —COO-cyclo-C₆H₁₁, —CONHBn, —CONH(C₁-C₆ alkyl), —CONH-propyl, —COO—C₈H₁₇,

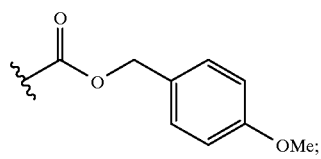

-continued

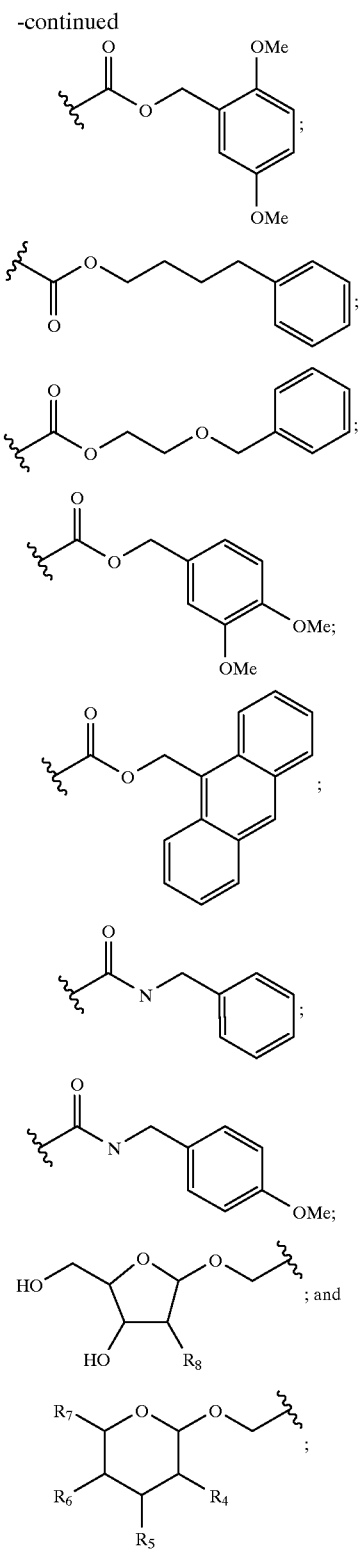

wherein:

R$_4$ is a radical selected from the group consisting of —OH, —OAc, 2—Cl—AcO—, CCl$_3$C(O)O—, 2-Br—AcO—, CF$_3$C(O)O—, 2-phenyl-AcO—, (C$_1$-C$_6$ alkyl)-C(O)O—, CH$_2$=CHC(O)O—, HC≡CC(O)O—, i-propyl-C(O)O—, cyclo-propyl-C(O)O—, i-butyl-C(O)O—, t-butyl-C(O)O—, cyclo-C$_6$H$_{11}$C(O)O—, phenyl-O—, 2-furyl-C(O)O—, PhCH=CHC(O)O—, and 2-thiophene-C(O)O—;

R$_5$ is a radical selected from the group consisting of —OAc and —OH;

R$_6$ is a radical selected from the group consisting of —OAc and —OH;

R$_7$ is a radical selected from the group consisting of —H, and -methyl; and

R$_8$ is a radical selected from the group consisting of —OAc, 2—Cl—AcO—, CCl$_3$C(O)O—, 2-Br—AcO—, CF$_3$C(O)O—, 2-phenyl-AcO—, (C$_1$-C$_6$ alkyl)-C(O)O—, CH$_2$=CHC(O)O—, HC≡CC(O)O—, i-propyl-C(O)O—, cyclo-propyl-C(O)O—, i-butyl-C(O)O—, t-butyl-C(O)O—, cyclo-C$_6$H$_{11}$C(O)O—, phenyl-O—, 2-furyl-C(O)O—, PhCH=CHC(O)O—, and 2-thiophene-C(O)O—.

4. A second advanced intermediate represented by the following structure:

wherein

R$_1$ is a radical selected from the group consisting of —O-paramethoxybenzyl, —O-triethylsilyl, and radicals represented by the following structures:

-continued

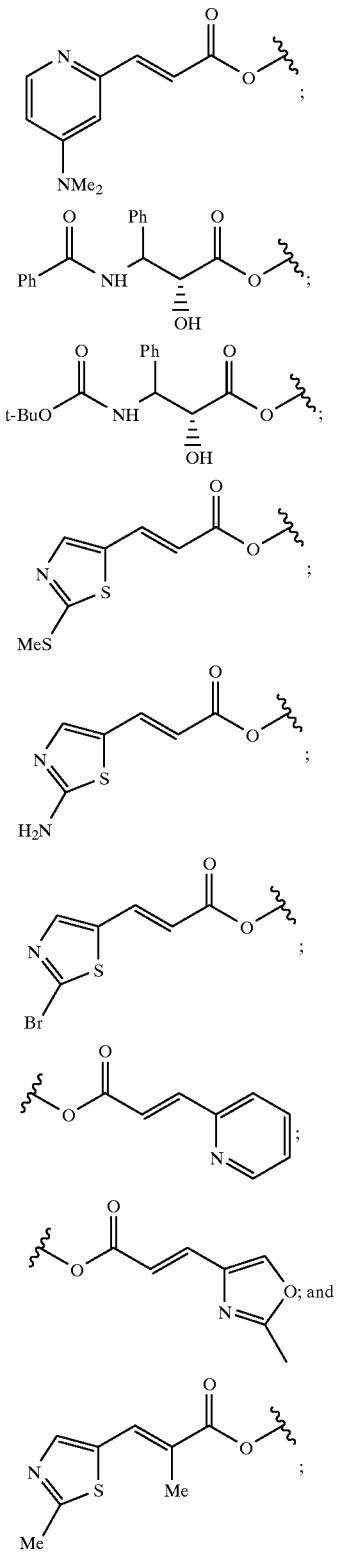

$R_3$ is a radical selected from the group consisting of —CH$_2$OC(C)CH$_3$, —CH$_2$OC(O)-phenyl, —CH$_2$OC(O)O—CH$_3$, —CH$_2$C(O)NH-phenyl, —CH$_2$—OH, —CH(O), —CH$_2$—O-tri-isopropylsilyl, —CH$_2$O—Ac, —CH$_2$—F, —CH$_2$N$_3$, —CH$_2$NAc, —CH$_2$NBz, —C(O)—CH$_2$CF$_3$, —C(O)—CH$_2$CH═CH$_2$, —C(O)—O—CH$_2$CH$_2$Cl, —C(O)O(CH$_2$)$_2$CH$_2$Cl, —C(O)O(CH$_2$)$_2$CH(CH$_3$)$_2$, —C(O)CH$_2$Ph, —C(O)CH$_2$-phenyl-OMe, —CH$_2$—O-tetrahydropyran, —CH$_2$—O—C(O)CHCl$_2$, —CH$_2$—O—C(O)—CCl$_3$, —CH$_2$-O—C(O)CHBr$_2$, —CH$_2$—O—C(O)—CF$_3$, —CH$_2$—O—C(O)CHPh$_2$, EtC(O)—O—CH$_2$—, CH$_2$═CHC(O)—O—CH$_2$—, HC≡—CC(O)—O—CH$_2$—, n-propyl-C(O)—O—CH$_2$—, i-PrC(O)—O—CH$_2$—, cyclopropyl-C(O)—O—CH$_2$—, n-BuC(O)—O—CH$_2$—, i-BuC(O)—O—CH$_2$—, t-BuC(O)—O—CH$_2$—, cyclo-C$_6$H$_{11}$C(O)—O—CH$_2$—, phenyl-O—CH$_2$—, 2-furyl-C(O)—O—CH$_2$—, PhCH═CHC(O)—O—CH$_2$—, 2-thiophene-C(O)—O—CH$_2$—, (C$_1$-C$_6$ alkyl)-O—CH$_2$—, i-propyl-O—CH$_2$—, allyl-O—CH$_2$—, benzyl-O—CH$_2$—, AcOCH$_2$CH$_2$—O—CH$_2$—, —COOH, —COO—(C$_1$-C$_6$ alkyl), —COO-i-propyl, —COO-t-butyl, —COO-benzyl, —COOCH$_2$CH═CH$_2$, —COO—CH$_2$C≡—CH, —COO-cyclo-C$_6$H$_{11}$, —CONHBn, —CONH(C$_1$-C$_6$ alkyl), —CONH-propyl, —COO—C$_8$H$_{17}$,

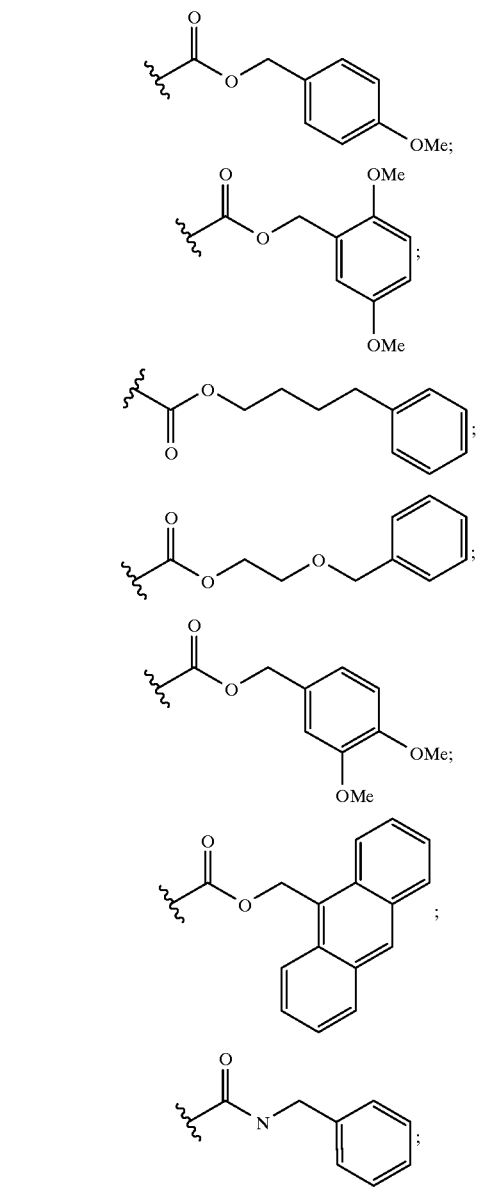

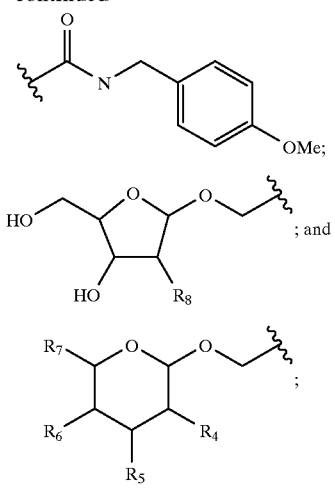

wherein

R$_4$ is a radical selected from the group consisting of —OH, —OAc, 2—Cl—AcO—, CCl$_3$C(O)O—, 2-Br—AcO—, CF$_3$C(O)O—, 2-phenyl-AcO—, (C$_1$-C$_6$ alkyl)-C(O)O—, CH$_2$=CHC(O)O—, HC≡CC(O)O—, i-propyl-C(O)O—, cyclo-propyl-C(O)O—, i-butyl-C(O)O—, t-butyl-C(O)O—, cyclo-C$_6$H$_{11}$C(O)O—, phenyl-O, 2-furyl-C(O)O—, PhCH=CHC(O)O—, and 2-thiophene-C(O)O—;

R$_5$ is a radical selected from the group consisting of —OAc and —OH;

R$_6$ is a radical selected from the group consisting of —OAc and —OH;

R$_7$ is a radical selected from the group consisting of —H, and -methyl; and

R$_8$ is a radical selected from the group consisting of —OAc, 2—Cl—Aco—, CCl$_3$C(O)O—, 2-Br—AcO—, CF$_3$C(O)O—, 2-phenyl-AcO—, (C$_1$-C$_6$ alkyl)-C(O)O—, CH$_2$=CHC(O)O—, HC≡—CC(O)O—, i-propyl-C(O)O—, cyclo-propyl-C(O)O—, i-butyl-C(O)O—, t-butyl-C(O)O—, cyclo-C$_6$H$_6$H$_{11}$C(O)O—, phenyl-O—, 2-furyl-C(O)O—, PhCH=CHC(O)O—, and 2-thiophene-C(O)O—.

5. A method for cyclizing the first advanced intermediate of claim 3 to the second advanced intermediate of claim 4 the method comprising the step of:

cyclizing the first intermediate to produce the second advanced intermediate.

6. A method for cyclizing the compound of claim 4 to a compound represented by structure (I):

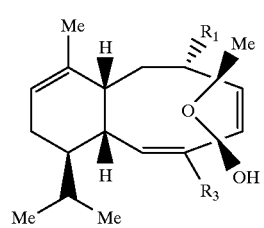

(I)

wherein:

R$_1$ is a radical selected from the group consisting of —O-paramethoxybenzyl, —O-triethylsilyl, and radicals represented by the following structures:

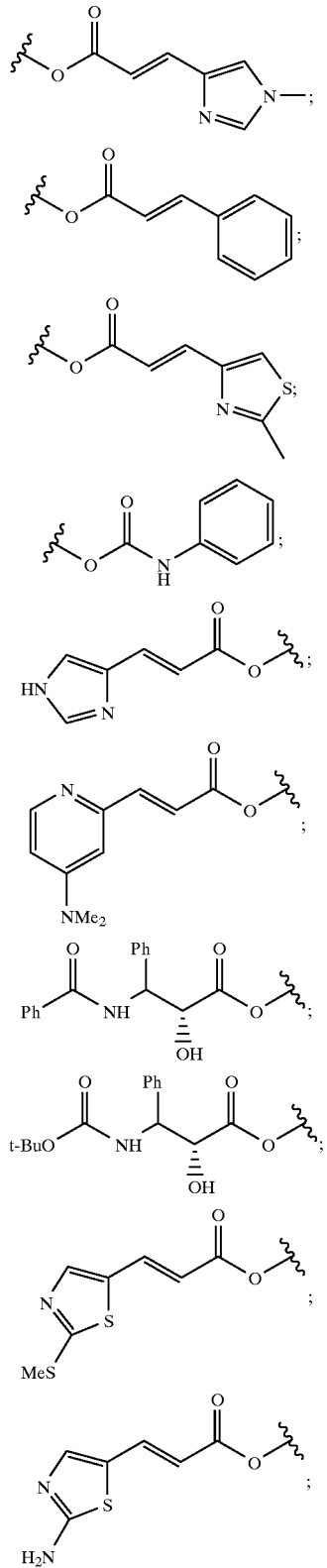

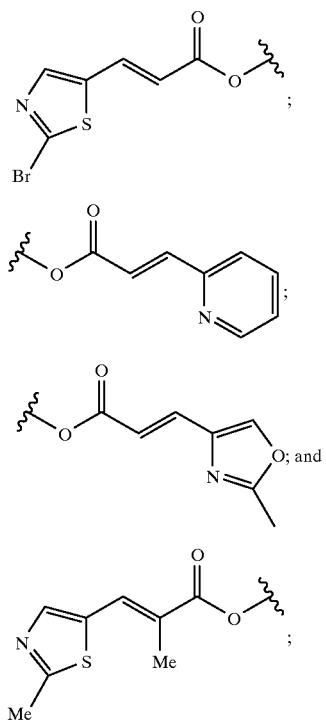

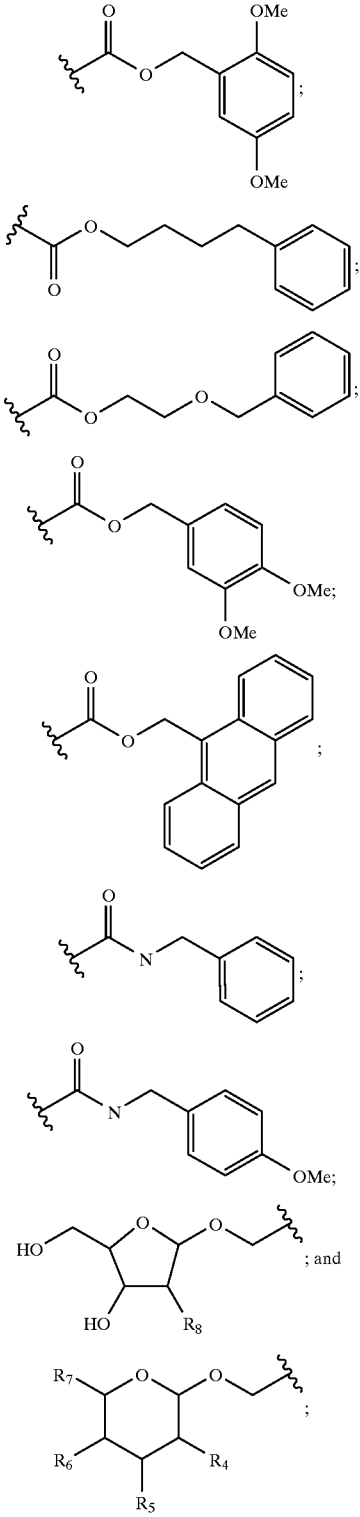

R$_3$ is a radical selected from the group consisting of —CH$_2$OC(O)CH$_3$, —CH$_2$OC(O)-phenyl, —CH$_2$OC(O)O—CH$_3$, —CH$_2$OC(O)NH-phenyl, —CH$_2$—OH, —CH(O), —CH$_2$—O-tri-isopropylsilyl, —CH$_2$O—Ac, —CH$_2$—F, —CH$_2$N$_3$, —CH$_2$NAc, —CH$_2$NBz, —C(O)—CH$_2$CF$_3$, —C(O)—CH$_2$CH=CH$_2$, —C(O)— O—CH$_2$CH$_2$Cl, —C(O)O(CH$_2$)$_2$CH$_2$Cl, —C(O)O(CH$_2$)$_2$CH(CH$_3$)$_2$, —C(O)CH$_2$Ph, —C(O)CH$_2$-phenyl-OMe, —CH$_2$—O-tetrahydropyran, —CH$_2$—O—C(O)CHCl$_2$, —CH$_2$—O—C(O)—CCl$_3$, —CH$_2$—O—C(O)CHBr$_2$, —CH$_2$—O—C(O)—CF$_3$, —CH$_2$—O—C(O)CHPh$_2$, EtC(O)—O—CH$_2$—, CH$_2$=CHC(O)—O—CH$_2$—, HC≡CC(O)—O—CH$_2$—, n-propyl-C(O)—O—CH$_2$—, i-PrC(O)—O—CH$_2$—, cyclopropyl-C(O)—O—CH$_2$—, n-BuC(O)—O—CH$_2$—, i-BuC(O)—O—CH$_2$—, t-BuC(O)—O—CH$_2$—, cyclo-C$_6$H$_{11}$C(O)—O—CH$_2$—, phenyl-O—CH$_2$—, 2-furyl-C(O)—O—CH$_2$—, PhCH=CHC(O)—O—CH$_2$13, 2-thiophene-C(O)—O—CH$_2$—, (C$_1$-C$_6$ alkyl)-O—CH$_2$—, i-propyl-O—CH$_2$—, allyl-O—CH$_2$—, benzyl-O—CH$_2$—, AcOCH$_2$CH$_2$—O—CH$_2$—, —COOH, —COO—(C$_1$-C$_6$ alkyl), —COO-i-propyl, —COO-t-butyl, —COO-benzyl, —COOCH$_2$CH=CH$_2$, —COO—CH$_2$C≡CH, —COO-cyclo-C$_6$H$_{11}$, —CONHBn, —CONH(C$_1$-C$_6$ alkyl), —CONH-propyl, —COO—C$_6$H$_{17}$,

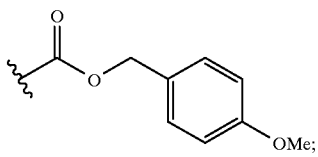

wherein:

R$_4$ is a radical selected from the group consisting of —OH, —OAc, 2—Cl—AcO—, CCl$_3$C(O)O—, 2-Br—AcO—, CF$_3$C(O)O—, 2-phenyl-AcO—, (C$_1$-C$_6$ alkyl)-C(O)O—, CH$_2$=CHC(O)O—, HC≡—CC(O)O—, i-propyl-C(O)O—, cyclo-propyl-C(O)O—, i-butyl-C(O)O—, t-butyl-C(O)O—, cyclo- $C_6H_{11}C(O)O-$, phenyl-O—, 2-furyl-C(O)O—, PhCH=CHC(O)O—, and 2-thiophene-C(O)O—;

$R_5$ is a radical selected from the group consisting of —OAc and —OH;

$R_6$ is a radical selected from the group consisting of —OAc and —OH;

$R_7$ is a radical selected from the group consisting of —H, and -methyl;

$R_8$ is a radical selected from the group consisting of —OAc, 2-Cl—AcO—, $CCl_3C(O)O-$, 2-Br—AcO—, $CF_3C(O)O-$, 2-phenyl-AcO—, $(C_1-C_6\text{ alkyl})$-C(O)O—, $CH_2=CHC(O)O-$, HC≡—CC(O)O—, i-propyl-C(O)O—, cyclo-propyl-C(O)O—, i-butyl-C(O)O—, t-butyl-C(O)O—, cyclo-$C_6H_{11}C(O)O-$, phenyl-O—, 2-furyl-C(O)O—, PhCH=CHC(O)O—, and 2-thiophene-C(O)O—;

the method comprising the following step:
cyclizing the compound of claim 4 to produce the compound of structure (I).

7. A method for promoting tubulin assembly, the method comprising the step of contacting tubulin with a compound described in claim 1 for promoting tubulin assembly.

8. A method for stabilizing a plurality of microtubules, the method comprising the step of contacting tubulin with a compound described in claim 1 for stabilizing the plurality of microtubules.

* * * * *